United States Patent
Savidge et al.

(10) Patent No.: US 7,329,799 B2
(45) Date of Patent: Feb. 12, 2008

(54) MATERIALS AND METHODS FOR THE MODULATION OF CYCLIN-DEPENDENT KINASE INHIBITOR-LIKE POLYPEPTIDES IN MAIZE

(75) Inventors: Beth Savidge, Davis, CA (US); Wei Zheng, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 370 days.

(21) Appl. No.: 10/890,629

(22) Filed: Jul. 14, 2004

(65) Prior Publication Data

US 2005/0048624 A1 Mar. 3, 2005

Related U.S. Application Data

(60) Provisional application No. 60/486,935, filed on Jul. 14, 2003.

(51) Int. Cl.
- C12N 15/29 (2006.01)
- C12N 15/82 (2006.01)
- C12N 5/04 (2006.01)
- A01H 5/00 (2006.01)
- A01H 5/10 (2006.01)

(52) U.S. Cl. ............ 800/298; 800/320.1; 536/23.1; 536/23.6; 435/320.1; 435/419; 426/531

(58) Field of Classification Search ........... 536/23.1, 536/23.6, 24.1; 435/410, 320.1, 419; 800/298; 426/531

See application file for complete search history.

(56) References Cited

U.S. PATENT DOCUMENTS

| | | |
|---|---|---|
| 6,465,718 B1 | 10/2002 | Inze et al. |
| 6,476,212 B1 | 11/2002 | Lalgudi et al. |
| 6,710,227 B1 | 3/2004 | Inze et al. |
| 2002/0006663 A1 | 1/2002 | Scadden et al. |
| 2004/0003433 A1 | 1/2004 | Gordon-Kamm et al. |
| 2004/0214272 A1* | 10/2004 | La Rosa et al. ............ 435/69.1 |
| 2006/0123505 A1* | 6/2006 | Kikuchi et al. ............ 800/278 |

FOREIGN PATENT DOCUMENTS

| | | |
|---|---|---|
| WO | WO 97/26327 | 7/1997 |
| WO | WO 99/14331 | 3/1999 |
| WO | WO 99/64599 | 12/1999 |
| WO | WO 00/60087 | 10/2000 |
| WO | WO 00/69883 | 11/2000 |
| WO | WO 01/85946 | 11/2001 |
| WO | WO 02/28893 | 4/2002 |
| WO | WO 02/053589 | 7/2002 |
| WO | WO 02/081623 | 10/2002 |

OTHER PUBLICATIONS

Zhou et al (2003, Plant Journal 35(4):476-489).*
Zhou et al (2003, Planta 216(4):604-613).*
Bowie et al, Science 247:1306-1310, 1990.*
McConnell et al, Nature 411 (6838):709-713, 2001.*
Zhou et al (2002, Planta 215(2):248-257).*
De Veylder et al., "Functional Analysis of Cyclin-Dependent Kinase Inhibitors of Arabidopsis", The Plant Cell, 13:1653-1667 (2001).
Jasinski et al., "The CDK Inhibitor NtKIS1a is Involved in Plant Development, Endoreduplication and Restores Normal Development of Cyclin D3; 1-overexpressing Plants", Journal of Cell Science, 115:973-982 (2002).
Schnittger et al., "Misexpression of the Cyclin-Dependent Kinase Inhibitor IC1/KRP1 in Single-Celled Arabidopsis Trichomes Reduces Endoreduplication and Cell Size and Induces Cell Death", The Plant Cell, 15:303-315 (2003).
Wang et al., "ICK1, a Cyclin-Dependent Protein Kinase Inhibitor From Arabidopsis thaliana Interacts With Both Cdc2a and CycD3, and its Expression is induced by Abscisic Acid", The Plant Journal, 15(4):501-510 (1998).
Wang et al., "A Plant Cyclin-Dependent Kinase Inhibitor Gene", Nature, 386:451-452 (1997).
Zhou et al., "Effects of Co-expressing the Plant CDK Inhibitor ICK1 and D-type Cyclin Genes on Plant Growth, Cell Size and Ploidy in Arabidopsis thaliana", Planta, 216:604-613 (2003).
Zhou et al., "The Plant Cyclin-Dependent Kinase Inhibitor ICK1 has Distinct Functional Domains for in vivo Kinase Inhibition, Protein Instability and Nuclear Localization", The Plant Journal, 35:476-489 (2003).

* cited by examiner

*Primary Examiner*—Stuart F. Baum
(74) *Attorney, Agent, or Firm*—Sonnenschein Nath & Rosenthal LLP

(57) ABSTRACT

Isolated or purified nucleic acid molecules encoding polypeptides having cyclin-dependent kinase (CDK) inhibitor-like activity; vectors; host cells; polypeptides having CDK inhibitor-like activity; nucleic acid constructs for suppression of CDK inhibitor-like activity; methods of suppressing and up-regulating the expression of one or more CDK inhibitor-like genes in a maize cell, tissue, organ, or plant; a maize cell, tissue, organ, or plant in which the expression of a CDK inhibitor-like gene has been suppressed or up-regulated in accordance with such methods; and a seed (and the oil and meal thereof) obtained from a plant in which the expression of one or more CDK inhibitor-like genes has been suppressed or up-regulated.

9 Claims, 5 Drawing Sheets

FIG. 1

Construction of F1-4 RNAi intermediate construct

A. Primer regions and directions

B. Assembling procedures

Construction of F5-8 RNAi intermediate construct

A. Primer regions and directions

B. Assembling procedures

Step 1: Construction of F5-8 sense and connection of ZmDnaK intron to F5-8 sense

Step 2: Cloning of antisense connections of F5-F8 to ZmDnaK intron

MATERIALS AND METHODS FOR THE MODULATION OF CYCLIN-DEPENDENT KINASE INHIBITOR-LIKE POLYPEPTIDES IN MAIZE

This application claims the benefit of U.S. Provisional Application Ser. No. 60/486,935, filed Jul. 14, 2003, which is incorporated herein by reference in its entirety.

TECHNICAL FIELD OF THE INVENTION

The present invention relates to isolated or purified nucleic acid molecules encoding polypeptides having cyclin-dependent kinase (CDK) inhibitor-like activity, complementary and antisense nucleic acid molecules, vectors, host cells, polypeptides having CDK inhibitor-like activity and materials and methods for suppressing and up-regulating the expression of one or more CDK inhibitor-like genes in maize.

BACKGROUND OF THE INVENTION

The activation/inactivation of CDK by cyclins drives the transition between the different phases of the cell cycle. CDK activity is also regulated by CDK inhibitors known as KRPs (Kip-related proteins, wherein "Kip" is short for "kinase inhibitor proteins"). Other CDK inhibitors from plants and animal systems are known as CKI, ICK, Cip, and Ink (De Veylder, 2001, *Plant Cell*, 13:1653-1667) and KIS (Jasinski et al., *J. Cell. Sci.*, 115:973-982 (2002)). CDK inhibitors have been identified in plants, including *Arabidopsis* and tobacco. The CDK inhibitors of plants have approximately 35 amino acids at the carboxy terminus homologous to the amino-terminal cyclin/CDK-binding domain of animal CDK inhibitors of the $p21^{Cip1}/p27^{Kip1}/p57^{Kip2}$ types. Outside of the carboxy-terminal region, the plant CDK inhibitors identified thus far are structurally different.

BRIEF SUMMARY OF THE INVENTION

Suppression of the expression of a CDK inhibitor-like gene can result in increased cellular proliferation and/or increased mitotic index. Suppression of the expression of a CDK inhibitor-like gene can also result in increased oil and increased yield.

The present invention provides isolated or purified nucleic acid molecules encoding CDK inhibitor-like polypeptides from maize. In one embodiment, the molecule comprises (i) the nucleotide sequence of SEQ ID NO: 1 [ZmKRP1; "Zm" indicates *Zea mays*; "KRP" indicates Kip related protein; the number is the designation given to a particular gene], (ii) a nucleotide sequence encoding the amino acid sequence of SEQ ID NO: 2 [ZmKRP1], (iii) a nucleotide sequence that encodes an amino acid sequence that is at least about 70% identical to the amino acid sequence of SEQ ID NO: 2 [ZmKRP 1] and has CDK inhibitor-like activity, or (iv) a fragment of any of (i)-(iii), wherein the fragment comprises at least about 35 contiguous nucleotides.

In another embodiment, the molecule comprises (i) the nucleotide sequence of SEQ ID NO: 3 [ZmKRP2], (ii) a nucleotide sequence encoding the amino acid sequence of SEQ ID NO: 4 [ZmKRP2], (iii) a nucleotide sequence that encodes an amino acid sequence that is at least about 70% identical to the amino acid sequence of SEQ ID NO: 4 [ZmKRP2] and has CDK inhibitor-like activity, or (iv) a fragment of any of (i)-(iii), wherein the fragment comprises at least about 35 contiguous nucleotides.

In yet another embodiment, the molecule consists essentially of (i) the nucleotide sequence of SEQ ID NO: 7 [ZmKRP4], (ii) a nucleotide sequence encoding the amino acid sequence of SEQ ID NO: 8 [ZmKRP4], or (iii) a nucleotide sequence that encodes an amino acid sequence that is at least about 70% identical to the amino acid sequence of SEQ ID NO: 8 [ZmKRP4] and has CDK inhibitor-like activity.

In still yet another embodiment, the molecule comprises (i) the nucleotide sequence of SEQ ID NO: 9 [ZmKRP5], (ii) a nucleotide sequence encoding the amino acid sequence of SEQ ID NO: 10 [ZmKRP5], (iii) a nucleotide sequence that encodes an amino acid sequence that is at least about 70% identical to the amino acid sequence of SEQ ID NO: 10 [ZmKRP5] and has CDK inhibitor-like activity, or (iv) a fragment of any of (i)-(iii), wherein the fragment comprises at least about 120 contiguous nucleotides.

In a further embodiment, the molecule consists essentially of (i) the nucleotide sequence of SEQ ID NO: 11 [ZmKRP6], (ii) a nucleotide sequence encoding the amino acid sequence of SEQ ID NO: 12 [ZmKRP6], (iii) a nucleotide sequence that encodes an amino acid sequence that is at least about 70% identical to the amino acid sequence of SEQ ID NO: 12 [ZmKRP6] and has CDK inhibitor-like activity, or (iv) a fragment of any of (i)-(iii), wherein the fragment comprises at least about 390 contiguous nucleotides.

In view of the above, the present invention further provides vectors comprising the above-described nucleic acid molecules. Host cells comprising the isolated or purified nucleic acid molecules, optionally in the form of vectors, are also provided.

Also in view of the above, the present invention provides isolated or purified polypeptides encoded by the above-described nucleic acid molecules. Isolated or purified nucleic acid molecules, optionally in the form of a vector, comprising or consisting essentially of complementary and antisense sequences to some of the above-described molecules, SEQ ID NOS: 13, 15, and 17, and nucleotide sequences encoding the amino acid sequences of SEQ ID NOS: 6, 14, 16, and 18 are also provided. When the sequence is SEQ ID NO: 1, encodes SEQ ID NO: 2, is SEQ ID NO: 3, or encodes SEQ ID NO: 4, the complementary or antisense sequence comprises at least 35 contiguous nucleotides.

Further provided are nucleic acid constructs comprising at least one transcribable nucleotide sequence, the expression of which results in the suppression of an endogenous nucleotide sequence selected from the group consisting of:

SEQ ID NO: 1 [ZmKRP1], a nucleotide sequence encoding the amino acid sequence of SEQ ID NO: 2 [ZmKRP1], SEQ ID NO: 3 [ZmKRP2], and a nucleotide sequence encoding the amino acid sequence of SEQ ID NO: 4 [ZmKRP2], alone or in further combination with at least one other nucleotide sequence, the expression of which results in the suppression of an endogenous nucleotide sequence selected from the group consisting of SEQ ID NO: 5 [ZmKRP3], a nucleotide sequence encoding the amino acid sequence of SEQ ID NO: 6 [ZmKRP3], SEQ ID NO: 7 [ZmKRP4], a nucleotide sequence encoding the amino acid sequence of SEQ ID NO: 8 [ZmKRP4], SEQ ID NO: 9 [ZmKRP5], a nucleotide sequence encoding the amino acid sequence of SEQ ID NO: 10 [ZmKRP5], SEQ ID NO: 11[ZmKRP6], a nucleotide sequence encoding the amino acid sequence of SEQ ID NO: 12 [ZmKRP6], SEQ ID NO:

13 [ZmKRP7], a nucleotide sequence encoding the amino acid sequence of SEQ ID NO: 14 [ZmKRP7], SEQ ID NO: 15 [ZmKRP8], a nucleotide sequence encoding the amino acid sequence of SEQ ID NO: 16 [ZmKRP8], SEQ ID NO: 17 [ZmKRP9], and a nucleotide sequence encoding the amino acid sequence of SEQ ID NO: 18 [ZmKRP9], wherein, when the nucleic acid construct comprises two or more transcribable nucleotide sequences, the nucleotide sequences can be present in any order on the nucleic acid construct and can be polycistronic, wherein each transcribable nucleotide sequence comprises at least about 100 contiguous nucleotides, and wherein the expression of each transcribable nucleotide sequence optionally induces gene suppression.

In another embodiment, the nucleic acid construct comprises at least one transcribable nucleotide sequence, the expression of which results in the suppression of an endogenous nucleic acid sequence selected from SEQ ID NO: 7 [ZmKRP4] and/or SEQ ID NO: 17 [ZmKRP9], either one or both of the transcribable nucleotide sequence in further combination with at least one other transcribable nucleotide sequence, the expression of which results in the suppression of an endogenous nucleotide sequence selected from the group consisting of:

(i) SEQ ID NO: 1 [ZmKRP1] or a nucleotide sequence encoding the amino acid sequence of SEQ ID NO: 2 [ZmKRP1], (ii) SEQ ID NO: 3 [ZmKRP2] or a nucleotide sequence encoding the amino acid sequence of SEQ ID NO: 4 [ZmKRP2], (iii) SEQ ID NO: 5 [ZmKRP3] or a nucleotide sequence encoding the amino acid sequence of SEQ ID NO: 6 [ZmKRP3], provided that the transcribable nucleotide sequence does not entirely correspond to nucleotides 175-342 of SEQ ID NO: 5, (iv) SEQ ID NO: 9 [ZmKRP5] or a nucleotide sequence encoding the amino acid sequence of SEQ ID NO: 10 [ZmKRP5], provided that the transcribable nucleotide sequence does not entirely correspond to nucleotides 450-570 of SEQ ID NO: 9, (v) SEQ ID NO: 11 [ZmKRP6] or a nucleotide sequence encoding the amino acid sequence of SEQ ID NO: 12 [ZmKRP6], provided that the transcribable nucleotide sequence does not entirely correspond to nucleotides 380-765 of SEQ ID NO: 11, (vi) SEQ ID NO: 13 [ZmKRP7] or a nucleotide sequence encoding the amino acid sequence of SEQ ID NO: 14 [ZmKRP7], provided that the transcribable nucleotide sequence does not entirely correspond to nucleotides 335-718 of SEQ ID NO: 13, and (vii) SEQ ID NO: 15 [ZmKRP8] or a nucleotide sequence encoding the amino acid sequence of SEQ ID NO: 16 [ZmKRP8], provided that the transcribable nucleotide sequence does not entirely correspond to nucleotides 350-405 or 420-698 of SEQ ID NO: 15, wherein the transcribable nucleotide sequences can be present in any order on the nucleic acid construct and can be polycistronic, wherein each transcribable nucleotide sequence comprises at least about 100 contiguous nucleotides, and wherein the expression of each transcribable nucleotide sequence optionally induces gene suppression.

In yet another embodiment, the nucleic acid construct comprises at least one transcribable nucleotide sequence, the expression of which results in the suppression of an endogenous nucleotide sequence selected from the group consisting of:

(i) SEQ ID NO: 1 [ZmKRP1] or a nucleotide sequence encoding the amino acid sequence of SEQ ID NO: 2 [ZmKRP1], (ii) SEQ ID NO: 3 [ZmKRP2] or a nucleotide sequence encoding the amino acid sequence of SEQ ID NO: 4 [ZmKRP2], (iii) SEQ ID NO: 5 [ZmKRP3] or a nucleotide sequence encoding the amino acid sequence of SEQ ID NO: 6 [ZmKRP3], provided that the transcribable nucleotide sequence does not entirely correspond to nucleotides 175-342 of SEQ ID NO: 5, (iv) SEQ ID NO: 9 [ZmKRP5] or a nucleotide sequence encoding the amino acid sequence of SEQ ID NO: 10 [ZmKRP5], provided that the transcribable nucleotide sequence does not entirely correspond to nucleotides 450-570 of SEQ ID NO: 9, (v) SEQ ID NO: 11 [ZmKRP6] or a nucleotide sequence encoding the amino acid sequence of SEQ ID NO: 12 [ZmKRP6], provided that the transcribable nucleotide sequence of SEQ ID NO: 11 does not entirely correspond to nucleotides 380-765 of SEQ ID NO: 11, (vi) SEQ ID NO: 13 [ZmKRP7] or a nucleotide sequence encoding the amino acid sequence of SEQ ID NO: 14 [ZmKRP7], provided that the transcribable nucleotide sequence does not entirely correspond to nucleotides 335-718 of SEQ ID NO: 13, (vii) SEQ ID NO: 15 [ZmKRP8] or a nucleotide sequence encoding the amino acid sequence of SEQ ID NO: 16 [ZmKRP8], provided that the transcribable nucleotide sequence does not entirely correspond to nucleotides 350-405 or 420-698 of SEQ ID NO: 15, and (viii) SEQ ID NO: 17 [ZmKRP9] or a nucleotide sequence encoding the amino acid sequence of SEQ ID NO: 18 [ZmKRP9], provided that the transcribable nucleotide sequence does not entirely correspond to nucleotides 1-183 of SEQ ID NO: 17, wherein the transcribable nucleotide sequences can be present in any order on the nucleic acid construct and can be polycistronic, wherein each transcribable nucleotide sequence comprises at least about 100 contiguous nucleotides, and wherein the expression of each transcribable nucleotide sequence optionally induces gene suppression.

A method of suppressing the expression of one or more CDK inhibitor-like genes in a maize cell, a maize tissue, a maize organ, or a maize plant is also provided. The method comprises contacting said maize cell, maize tissue, maize organ or maize plant with a nucleic acid construct described above.

In this regard, also provided are a maize cell, a maize tissue, a maize organ, or a maize plant in which the expression of a CDK inhibitor-like gene has been suppressed in accordance with such a method. A seed obtained from a plant in which the expression of one or more CDK inhibitor-like genes has been suppressed is also provided.

BRIEF DESCRIPTION OF THE FIGURES

FIG. 1 is the amino acid sequence alignment of the polypeptides of the present invention with published sequences of CDK inhibitors of *Arabidopsis*. The sequences of *Arabidopsis* are as indicated in Example 1. The sequences represented are: AtICK1 (or AtKRP1) (SEQ ID NO:60); AtICK2 (or AtKRP2) (SEQ ID NO:61); AtKRP3 (SEQ ID NO:62); AtKRP4 (SEQ ID NO:63); AtKRP5 (SEQ ID NO:64); AtKRP6 (SEQ ID NO:65); AtKRP7 (SEQ ID NO:66); ZmKRP1 (SEQ ID NO:2); ZmKRP2 (SEQ ID NO:4); ZmKRP3 (SEQ ID NO:6); ZmKRP4 (SEQ ID NO:8); ZmKRP5 (SEQ ID NO:10); ZmKRP6 (SEQ ID NO:12); ZmKRP7 (SEQ ID NO:14); ZmKRP8 (SEQ ID NO:16); and ZmKRP9 (SEQ ID NO:18).

BRIEF DESCRIPTION OF THE SEQUENCES

Figure 2:
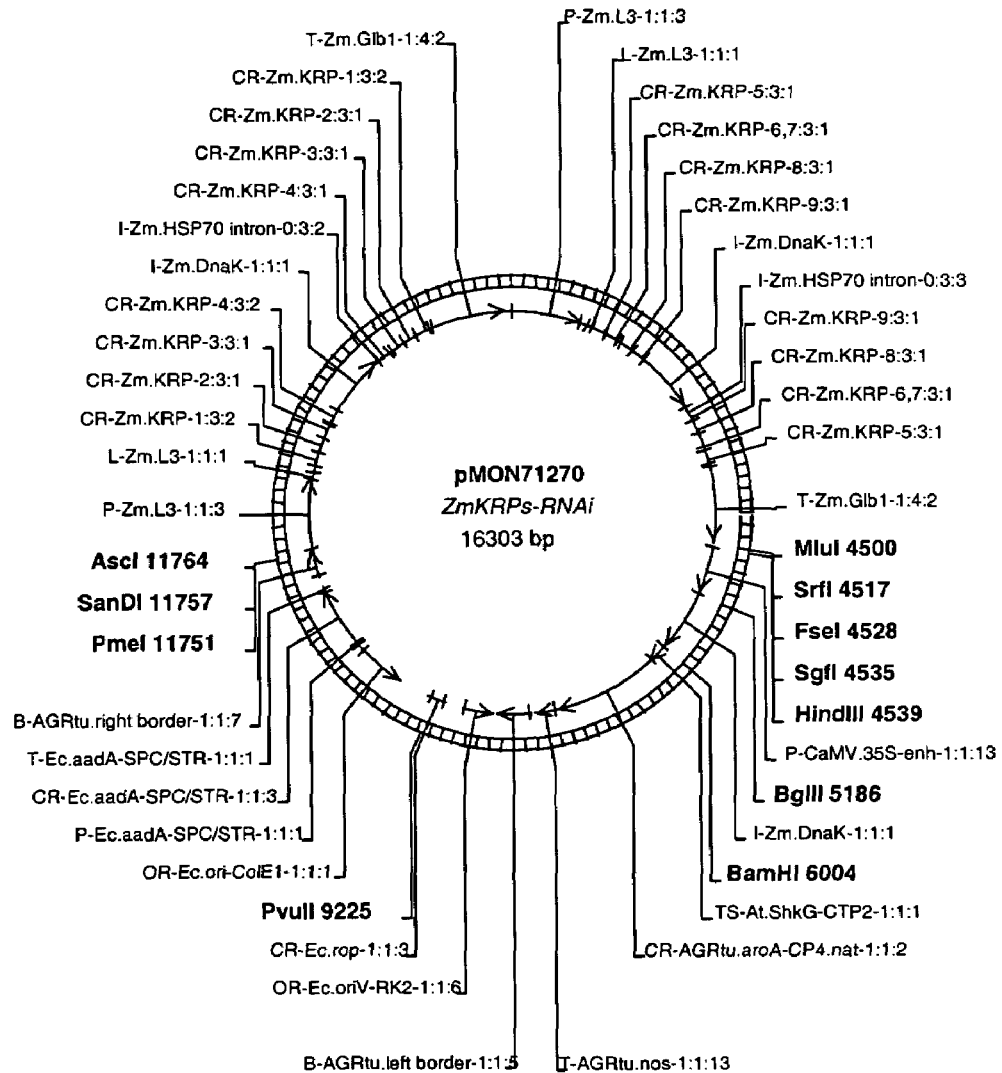
FIG. 2 is the construct map of pMON71270.

SEQ ID NO: 1 is the nucleotide sequence of ZmKRP1.
SEQ ID NO: 2 is the amino acid sequence of ZmKRP1.
SEQ ID NO: 3 is the nucleotide sequence of ZmKRP2.
SEQ ID NO: 4 is the amino acid sequence of ZmKRP2.
SEQ ID NO: 5 is the nucleotide sequence of ZmKRP3.
SEQ ID NO: 6 is the amino acid sequence of ZmKRP3.
SEQ ID NO: 7 is the nucleotide sequence of ZmKRP4.
SEQ ID NO: 8 is the amino acid sequence of ZmKRP4.
SEQ ID NO: 9 is the nucleotide sequence of ZmKRP5.
SEQ ID NO: 10 is the amino acid sequence of ZmKRP5.
SEQ ID NO: 11 is the nucleotide sequence of ZmKRP6.
SEQ ID NO: 12 is the amino acid sequence of ZmKRP6.
SEQ ID NO: 13 is the nucleotide sequence of ZmKRP7.
SEQ ID NO: 14 is the amino acid sequence of ZmKRP7.
SEQ ID NO: 15 is the nucleotide sequence of ZmKRP8.
SEQ ID NO: 16 is the amino acid sequence of ZmKRP8.
SEQ ID NO: 17 is the nucleotide sequence of ZmKRP9.
SEQ ID NO: 18 is the amino acid sequence of ZmKRP9.
SEQ ID NO: 19 is the nucleotide sequence of 200 base pairs (bp) from the 3' end of ZmKRP1 (F1).
SEQ ID NO: 20 is the nucleotide sequence of 200 bp from near the 3' end of ZmKRP2 (F2).
SEQ ID NO: 21 is the nucleotide sequence of 200 bp from the 3' end of ZmKRP3 (F3).
SEQ ID NO: 22 is the nucleotide sequence of 200 bp from the 3' end of ZmKRP4 (F4).
SEQ ID NO: 23 is the nucleotide sequence of 200 bp from the 3' end of ZmKRP5 (F5).
SEQ ID NO: 24 is the nucleotide sequence of 200 bp from close to the 3' end of ZmKRP6 and ZmKRP7 (F6).
SEQ ID NO: 25 is the nucleotide sequence of 200 bp from near the 3' end of ZmKRP8 (F7).
SEQ ID NO: 26 is the nucleotide sequence of 183 bp from the 3' end of ZmKRP8 (F8).
SEQ ID NO: 27 is the nucleotide sequence of the ZmDnaK intron fragment.
SEQ ID NO: 28 is the nucleotide sequence of the primer P1-StuI.
SEQ ID NO: 29 is the nucleotide sequence of the primer P1-2R.
SEQ ID NO: 30 is the nucleotide sequence of the primer P2-3.
SEQ ID NO: 31 is the nucleotide sequence of the primer P4-Bgl.
SEQ ID NO: 32 is the nucleotide sequence of the primer P3-4.
SEQ ID NO: 33 is the nucleotide sequence of the primer P5-Bam.
SEQ ID NO: 34 is the nucleotide sequence of the primer P5-Bgl.
SEQ ID NO: 35 is the nucleotide sequence of the primer P1-SseBam.
SEQ ID NO: 36 is the nucleotide sequence of the primer Pi-Bgl.
SEQ ID NO: 37 is the nucleotide sequence of the primer Pi-Bam.
SEQ ID NO: 38 is the nucleotide sequence of the primer P5-Nco.
SEQ ID NO: 39 is the nucleotide sequence of the primer P5-6.
SEQ ID NO: 40 is the nucleotide sequence of the primer P6-7.
SEQ ID NO: 41 is the nucleotide sequence of the primer P8-Bgl.
SEQ ID NO: 42 is the nucleotide sequence of the primer P7-8.
SEQ ID NO: 43 is the nucleotide sequence of the primer P8-i.
SEQ ID NO: 44 is the nucleotide sequence of the 5' untranslated region (UTR) of ZmKRP1.
SEQ ID NO: 45 is the nucleotide sequence of the 3' UTR of ZmKRP1.
SEQ ID NO: 46 is the nucleotide sequence of the 5' UTR of ZmKRP2.
SEQ ID NO: 47 is the nucleotide sequence of the 3' UTR of ZmKRP2.
SEQ ID NO: 48 is the nucleotide sequence of the 3' UTR of ZmKRP3.
SEQ ID NO: 49 is the nucleotide sequence of the 5' UTR of ZmKRP4.
SEQ ID NO: 50 is the nucleotide sequence of the 3' UTR of ZmKRP4.
SEQ ID NO: 51 is the nucleotide sequence of the 5' UTR of ZmKRP5.
SEQ ID NO: 52 is the nucleotide sequence of the 3' UTR of ZmKRP5.
SEQ ID NO: 53 is the nucleotide sequence of the 5' UTR of ZmKRP6.
SEQ ID NO: 54 is the nucleotide sequence of the 3' UTR of ZmKRP6.
SEQ ID NO: 55 is the nucleotide sequence of the 5' UTR of ZmKRP7.
SEQ ID NO: 56 is the nucleotide sequence of the 3' UTR of ZmKRP7.
SEQ ID NO: 57 is the nucleotide sequence of the 5' UTR of ZmKRP8.
SEQ ID NO: 58 is the nucleotide sequence of the 3' UTR of ZmKRP9.
SEQ ID NO: 59 is a conserved sequence from the C-terminal region of certain polypeptides.

DETAILED DESCRIPTION OF THE INVENTION

Suppression of the expression of a CDK inhibitor-like gene can result in increased cellular proliferation and/or increased mitotic index. For example, increasing cellular proliferation may result in an increased embryo size and an increase in the amount of oil.

Suppression of the expression of a CDK inhibitor-like gene can also result in increased yield. Many agronomic traits can affect "yield". For example, these could include, without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. For example, these could also include, without limitation, efficiency of germination (including germination in stressed conditions), growth rate (including growth rate in stressed conditions), ear number, seed number per ear, seed size, composition of seed (starch, oil, protein), characteristics of seed fill. "Yield" can be measured in may ways, these might include test weight, seed weight, seed number per plant, seed weight, seed number per unit area (i.e., seeds, or weight of seeds, per acre), bushels per acre, tonnes per acre, tons per acre, kilo per hectare. In an embodiment, a plant of the present invention might exhibit an enhanced trait that is a component of yield. An enhanced trait is a trait, or phenotype of a plant, that is changed in a way that could be viewed as an agronomic improvement when compared to a non-transgenic plant of the same, or very similar, genotype.

The present invention provides, among other things, isolated or purified nucleic acid molecules encoding polypeptides of maize having CDK inhibitor-like activity. By "CDK-inhibitor like activity" is meant the ability to reduce CDK activity in a histone H1 kinase assay (see, Example 14). Preferably, CDK activity is reduced by at least about 10%, more preferably at least about 20%, even more preferably at least about 30%, still even more preferably at least about 40%, 50%, 60%, 70%, or 80%, and most preferably at least about 90% or more. By "isolated" is meant having been removed from its natural environment. If a nucleic acid, isolated means the separation of a nucleic acid from other nucleic acid molecules and the substantial separation from other cellular material and either culture medium, if produced by recombinant techniques, or chemical precursors, if synthesized. By "purified" is meant having been increased in purity, wherein "purity" is a relative term, and is not to be construed as absolute purity. "Nucleic acid molecules" is intended to encompass a polymer of DNA (e.g., cDNA or genomic DNA) or RNA (e.g., mRNA), i.e., a polynucleotide, which can be single-stranded or double-stranded, which can comprise chimeric DNA/RNA oligonucleotides, and which can contain non-natural or altered nucleotides.

In one embodiment, an isolated or purified nucleic acid molecule comprising (i) the nucleotide sequence of SEQ ID NO: 1 [ZmKRP1], (ii) a nucleotide sequence encoding the amino acid sequence of SEQ ID NO: 2 [ZmKRP1], (iii) a nucleotide sequence that encodes an amino acid sequence that is at least about 70% (or 75%, 80%, 85%, 90%, 95%, or 99%) identical to the amino acid sequence of SEQ ID NO: 2 [ZmKRP1] and has CDK inhibitor-like activity, or (iv) a fragment of any of (i)-(iii), wherein the fragment comprises at least about 35 (or 40, 45, 50, 55, 60, 65, 70, 75, 80, 85, 90, 95, 100, or more) contiguous nucleotides, is provided.

In another embodiment, an isolated or purified nucleic acid molecule comprising (i) the nucleotide sequence of SEQ ID NO: 3 [ZmKRP2], (ii) a nucleotide sequence encoding the amino acid sequence of SEQ ID NO: 4 [ZmKRP2], (iii) a nucleotide sequence that encodes an amino acid sequence that is at least about 70% (or 75%, 80%, 85%, 90%, 95%, or 99%) identical to the amino acid sequence of SEQ ID NO: 4 [ZmKRP2] and has CDK inhibitor-like activity, or (iv) a fragment of any of (i)-(iii), wherein the fragment comprises at least about 35 (or 40, 45, 50, 55, 60, 65, 70, 75, 80, 85, 90, 95, 100, or more) contiguous nucleotides, is provided.

In yet another embodiment, the present invention provides an isolated or purified nucleic acid molecule consisting essentially of (i) the nucleotide sequence of SEQ ID NO: 7 [ZmKRP4], (ii) a nucleotide sequence encoding the amino acid sequence of SEQ ID NO: 8 [ZmKRP4], or (iii) a nucleotide sequence that encodes an amino acid sequence that is at least about 70% (or 75%, 80%, 85%, 90%, 95%, or 99%) identical to the amino acid sequence of SEQ ID NO: 8 [ZmKRP4] and has CDK inhibitor-like activity.

In still yet another embodiment, the present invention provides an isolated or purified nucleic acid molecule comprising (i) the nucleotide sequence of SEQ ID NO: 9 [ZmKRP5], (ii) a nucleotide sequence encoding the amino acid sequence of SEQ ID NO: 10 [ZmKRP5], (iii) a nucleotide sequence that encodes an amino acid sequence that is at least about 70% (or 75%, 80%, 85%, 90%, 95%, or 99%) identical to the amino acid sequence of SEQ ID NO: 10 [ZmKRP5] and has CDK inhibitor-like activity, or (iv) a fragment of any of (i)-(iii), wherein the fragment comprises at least about 120 (or 125, 130, 135, 140, 145, 150, 155, 160, 165, 170, 175, 180, 185, 190, 195, 200, or more) contiguous nucleotides.

An isolated or purified nucleic acid molecule comprising (i) the nucleotide sequence of SEQ ID NO: 11 [ZmKRP6], (ii) a nucleotide sequence encoding the amino acid sequence of SEQ ID NO: 12 [ZmKRP6], (iii) a nucleotide sequence that encodes an amino acid sequence that is at least about 70% (or 75%, 80%, 85%, 90%, 95%, or 99%) identical to the amino acid sequence of SEQ ID NO: 12 [ZmKRP6] and has CDK inhibitor-like activity, and (iv) a fragment of any of (i)-(iv), wherein the fragment comprises at least about 390 (or 400, 405, 410, 415, 420, 425, 430, 435, 440, 445, 450, 455, 460, 465, 470, 475, 480, 485, 490, 495, 500, or more) contiguous nucleotides, are also provided.

Such nucleic acid molecules can be amplified using cDNA, mRNA or genomic DNA as a template and appropriate oligonucleotide primers according to standard PCR amplification techniques. Alternatively, they can be synthesized using standard synthetic techniques, such as an automated DNA synthesizer.

The above isolated or purified nucleic acid molecules are characterized, in part, in terms of "percentage of sequence identity." In this regard, a given nucleic acid molecule can be compared to an above-described nucleic acid molecule (i.e., the reference sequence) by optimally aligning the nucleic acid sequences over a comparison window, wherein the portion of the polynucleotide sequence in the comparison window may comprise additions or deletions (i.e., gaps) as compared to the reference sequence, which does not comprise additions or deletions, for optimal alignment of the two sequences. The percentage of sequence identity is calculated by determining the number of positions at which the identical nucleic acid base occurs in both sequences, i.e., the number of matched positions, dividing the number of matched positions by the total number of positions in the window of comparison, and multiplying the result by 100 to yield the percentage of sequence identity. Optimal alignment of sequences for comparison can be conducted by computerized implementations of known algorithms. Sequence alignments and percent identity calculations can be performed by the Clustal Algorithm (Higgins et al., CABIOS, 5 (2):151-153 (1989)), using default parameters of the Megalign program of the LASARGENE bioinformatics computing suite (DNASTAR Inc., Madison, Wis.), hereinafter referred to as "Clustal W Algorithm." Other computerized implementations include GAP, BESTFIT, FASTA, and TFASTA in the GCG Wisconsin Package (Accelrys, San Diego, Calif.), or BlastN and BlastX available from the National Center for Biotechnology Information, Bethesda, Md.). In addition, alignment can be performed by inspection. Sequences are typically compared using BESTFIT or BlastN with default parameters. A preferred method of determining identity is Clustal W Algorithm, in accordance with the parameters set forth in Example 1.

One of ordinary skill in the art will appreciate, however, that two polynucleotide sequences can be substantially different at the nucleic acid level, yet encode substantially similar, if not identical, amino acid sequences, due to the degeneracy of the genetic code. The present invention is intended to encompass such polynucleotide sequences. In this regard, it should be noted that fragments of the above-described nucleic acid molecules can be used as probes to identify other polynucleotide sequences.

An isolated or purified nucleic acid molecule comprising or consisting essentially of the complementary or antisense sequence (or fragment thereof, such as one comprising at least about 35 contiguous nucleotides) to an above-described isolated or purified nucleic acid molecule, as well as to SEQ ID NOS: 13, 15, and 17, and nucleotide sequences encoding the amino acid sequences of SEQ ID NOS: 6, 14, 16, and 18 are also provided. The isolated or purified nucleic acid molecule is optionally in the form of a vector.

If desired, an above-described isolated or purified nucleic acid molecule can be operably linked to a promoter. Promoters include, but are not limited to, promoters that function in bacteria, bacteriophage, plastids or plant cells, including promoters that are preferentially expressed in the male reproductive tissue. Any suitable promoter can be used as herein described below. Examples of such promoters include, but are not limited to, the SILKY1 promoter of maize (Ambrose et al., *Molec. Cell*, 5(3):569-579 (2000)), the NTM19 promoter of tobacco (Oldenhof et al., *Plant Molec. Biol.*, 31:213-225 (1996); U.S. Pat. No. 6,407,314; and WO 97/30166), the NPG1 promoter of tobacco (see, e.g., U.S. Application Publication 2003/0061635), the PCA55 promoter of maize (see, e.g., WO 92/13957), the AP3 promoter of *Arabidopsis* (Zhou et al., *Planta*, 215:248-257 (2002)), and the Bgp1 promoter of Brassica (Zhou et al. (2002), infra). Other examples include an anther-preferred promoter, such as that from LAT52 (Twell et al., *Molec. Gen. Genet.*, 217(2-3):240-245 (1989); and Twell et al., *Genes Dev.*, 5(3):496-507 (1991)) or RA8 of rice (Jeon et al., *Plant Mol. Biol.*, 39(1):35-44 (1999)), a pollen-preferred promoter, such as that from maize Zm13 (Guerrero et al., *Molec. Gen. Genet.*, 224:161-168 (1993)) or rice PSI (Zou et al., *Amer. J. Bot.*, 81(5):552-561 (1994)), and a microspore-preferred promoter, such as that from apg (anther-preferred; Twell et al., *Sex. Plant. Repro.*, 6:217-224 (1993)). In some instances, a promoter that is preferentially expressed in the male reproductive tissue of maize can be desirable (see, e.g., Example 5).

If desired, an above-described isolated or purified nucleic acid molecule can be operably linked to a promoter. Promoters of the instant invention generally include, but are not limited to, promoters that function in bacteria, bacteriophage, or plant cells. Useful promoters for bacterial expression are the lacZ, Sp6, T7, T5, or *E. coli* glg C promoters. Useful promoters for plants cells include the globulin promoter (see, for example, Belanger and Kriz, *Genet.*, 129:863-872 (1991)), gamma zein Z27 promoter (see, for example, Lopes et al., *Mol. Gen. Genet.*, 247:603-613 (1995)), L3 oleosin promoter (U.S. Pat. No. 6,433,252), barley PER1 promoter (Stacey et al., *Plant Mol. Biol.*, 31:1205-1216 (1996), embryo preferred promoters such as P-Zm.CEP1, P-Zm-.CPC214, P-Zm.CPC214tr1, P-Zm.CPC214tr2 or P-Os-.CPC214 (U.S. Provisional Application No. 60/531,483), incorporated herein by reference, USP promoters (U.S. Application Publication No. 2003/229918), incorporated herein by reference, 7Sα promoter, 7Sα' promoter (see, e.g., Beachy et al., *EMBO J.*, 4:3047 (1985) or Schuler et al., *Nucleic Acid Res.*, 10(24):8225-8244 (1982)), CaMV 35S promoter (Odell et al., *Nature*, 313:810 (1985)), the CaMV 19S (Lawton et al., *Plant Mol Biol.*, 9:31F (1987)), nos (Ebert et al., *PNAS U.S.A.*, 84:5745 (1987)), Adh (Walker et al., *PNAS U.S.A.*, 84:6624 (1987)), sucrose synthase (Yang et al., *PNAS U.S.A.* 87:4144 (1990)), tubulin, actin (Wang et al., *Mol. Cell. Biol.*, 12:3399 (1992)), cab (Sullivan et al., *Mol. Gen. Genet.*, 215:431 (1989)), PEPCase promoter (Hudspeth et al., *Plant Mol. Biol.*, 12:579 (1989)), or those associated with the R gene complex (Chandler et al., *The Plant Cell*, 1: 1175 (1989)). The Figwort Mosaic Virus (FMV) promoter (Richins et al., *Nucleic Acids Res.*, 20:8451 (1987)), arcelin, tomato E8, patatin, ubiquitin, mannopine synthase (mas), soybean seed protein glycinin (Gly), and soybean vegetative storage protein (vsp) promoters are other examples of useful promoters.

In one preferred embodiment the promoter used is highly expressed in the germ and/or aleurone tissue. Preferred promoters known to function in maize, and in other plants, include the promoters for oleosins (for example, the L3 promoter, U.S. Pat. No. 6,433,252), the globulin promoter (see, for example, Belanger and Kriz, *Genet.*, 129:863-872, 1991), the barley peroxiredoxin promoter (Perl, Stacy et al., *Plant Mol. Biol.*, 31:1205-1216, Accession #X9655 1), embryo preferred promoters such as P-Zm.CEP1 P-Zm-.CPC214, P-Zm.CPC214tr1, P-Zm.CPC214tr2, or P-Os-.CPC214 (U.S. Provisional Application No. 60/531,483), incorporated herein by reference, or the MIP synthase promoter of maize (WO 01/40440 A2).

Examples of promoters highly expressed in the endosperm include promoters from genes encoding zeins, which are a group of storage proteins found in maize endosperm. Genomic clones for zein genes have been isolated (Pedersen et al., *Cell*, 29: 1015-1026 (1982) and Russell et al., *Transgenic Res.*, 6(2): 157-168 (1997)) and the promoters from these clones, including the 15 kD, 16 kD, 19 kD, 22 kD, and 27 kD genes, can be used. Other preferred promoters, known to function in maize, and in other plants, include the promoters for the following genes: waxy (granule bound starch synthase), Brittle and Shrunken 2 (ADP glucose pyrophosphorylase), Shrunken 1 (sucrose synthase), branching enzymes I and II, starch synthases, debranching enzymes, oleosins, glutelins, sucrose synthases (Yang et al., *PNAS U.S.A.*, 87:4144-4148 (1990)), Betl1 (basal endosperm transfer layer) and globulin 1. Other promoters useful in the practice of the invention that are known by one of skill in the art are also contemplated by the invention.

Moreover, transcription enhancers or duplications of enhancers can be used to increase expression from a particular promoter. Examples of such enhancers include, but are not limited to the Adh intron1 (Callis et al., *Genes Develop.*, 1:1183 (1987)), a rice actin intron (McElroy et al., *Mol. Gen. Genet.*, 231(1):150-160 (1991)) (U.S. Pat. No. 5,641,876), sucrose synthase intron (Vasil et al., *Plant Physiol.*, 91:5175(1989)), a maize HSP70 intron (Rochester et al., *EMBO J.*, 5:451-458 (1986)) a TMV omega element (Gallie et al., *The Plant Cell*, 1:301 (1999)) the CaMV 35S enhancer or an octopine synthase enhancer (Last et al., U.S. Pat. No. 5,290,924). As the DNA sequence between the transcription initiation site and the start of the coding sequence, i.e., the untranslated leader sequence, can influence gene expression, one may also wish to employ a particular leader sequence. Any leader sequence available to one of skill in the art may be employed. Preferred leader sequences direct optimum levels of expression of the attached gene, for example, by increasing or maintaining mRNA stability and/or by preventing inappropriate initiation of translation (Joshi, *Nucl. Acid Res.*, 15:6643 (1987)). The choice of such sequences is at the discretion of those of skill in the art. Sequences that are derived from genes that are highly expressed in higher plants, and in soybean, corn, rice, and canola in particular, are contemplated.

An inducible promoter can be turned on or off by an exogenously added agent so that expression of an operably linked nucleic acid is also turned on or off. For example, a bacterial promoter, such as the $P_{tac}$, promoter can be induced to varying levels of gene expression depending on the level of isothiopropylgalactoside added to the transformed bacterial cells. In plants, inducible promoters can be used in those instances where the expression of a given gene is desired after a host plant has reached maturity. Such inducible promoters include heat shock promoters, stress response promoters, and chemically inducible promoters.

Expression cassettes of the invention will also include a sequence near the 3' end of the cassette that acts as a signal to terminate transcription from a heterologous nucleic acid and that directs polyadenylation of the resultant mRNA. These are commonly referred to as 3' untranslated regions or 3' UTRs. Some 3' elements that can act as transcription termination signals include those from the nopaline synthase gene of *Agrobacterium tumefaciens* (Bevan et al., *Nucl. Acid Res.*, 11:369 (1983)), a napin 3' untranslated region (Kridl et al., *Seed Sci Res.*, 1:209-219 (1991)), a globulin 3' untranslated region (Belanger and Kriz, *Genetics*, 129:863-872 (1991)), or one from a zein gene, such as Z27 (Lopes et al., *Mol Gen Genet.*, 247:603-613 (1995)). Other 3' elements known by one of skill in the art also can be used in the vectors of the invention.

The present invention further provides a vector comprising an above-described isolated or purified nucleic acid molecule. A nucleic acid molecule as described above can be cloned into any suitable vector and can be used to transform or transfect any suitable host. The selection of vectors and methods to construct them are commonly known to persons of ordinary skill in the art and are described in general technical references (see, in general, "Recombinant DNA Part D," *Methods in Enzymology*, Vol. 153, Wu and Grossman, eds., Academic Press (1987)). Desirably, the vector comprises regulatory sequences, such as transcription and translation initiation and termination codons, which are specific to the type of host (e.g., bacterium, fungus, or plant) into which the vector is to be introduced, as appropriate and taking into consideration whether the vector is DNA or RNA.

Constructs of vectors, which are circular or linear, can be prepared to contain an entire nucleic acid sequence as described above or a portion thereof ligated to a replication system functional in a prokaryotic or eukaryotic host cell. Replication systems can be derived from ColE1, 2 mµ plasmid, λphage, f1 filamentous phage, *Agrobacterium* species (e.g., *Ag. tumefaciens* and *Ag. rhizogenes*), and the like.

In addition to the replication system and the inserted nucleic acid, the construct can include one or more marker genes, which allow for selection of transformed or transfected hosts. Marker genes include biocide resistance, e.g., resistance to antibiotics, heavy metals, herbicides; etc., complementation in an auxotrophic host to provide prototrophy, and the like.

Suitable vectors include those designed for propagation or expression or both. A preferred cloning vector is selected from the group consisting of the pUC series, the pBluescript series (Stratagene, LaJolla, Calif.), the pET series (Novagen, Madison, Wis.), the pGEX series (Pharmacia Biotech, Uppsala, Sweden), and the pEX series (Clonetech, Palo Alto, Calif.). Bacteriophage vectors, such as λGT10, λGT11, λZapII (Stratagene), λ EMBL4, and λ NM1149, also can be used. Examples of plant expression vectors include pBI101, pBI101.2, pBI101.3, pBI121, and pBIN19 (Clonetech, Palo Alto, Calif.). Examples of yeast expression vectors include pYES2.1, pYES2, and other pYES derivatives (Invitrogen, Carlsbad, Calif.).

A plant expression vector can comprise a native or nonnative promoter operably linked to an above-described nucleic acid molecule. The selection of promoters, e.g., strong, weak, inducible, tissue-specific (i.e., specifically or preferentially expressed in a tissue), organ-specific (i.e., specifically or preferentially expressed in an organ) and developmental-specific (i.e., specifically or preferentially expressed during a particular stage(s) of development), is within the skill in the art. Similarly, the combining of a nucleic acid molecule as described above with a promoter is also within the skill in the art (see, e.g. Sambrook et al., *Molecular Cloning: A Laboratory Manual*, 2nd ed., Cold Spring Harbor Laboratory, Cold Spring Harbor Laboratory Press, Cold Spring Harbor, N.Y. (1989)).

If it is desired to up-regulate the expression of a CDK inhibitor-like gene, i.e., to increase the expression of a CDK inhibitor-like gene by any means, such as by about two-fold, ten-fold, 100-fold, or more at the mRNA level or protein level, it is preferred to do so by introducing a gene encoding a CDK inhibitor-like polypeptide as provided herein. The gene is preferably introduced by way of a vector. It is preferred that a lot of inhibitor is expressed in the tissue of interest. Multiple extra copies of the gene can be introduced into the plant cell, plant tissue, plant organ, or plant or a vector comprising a strong promoter, such as promoter, which is preferentially or specifically expressed in male reproductive tissue, is introduced into the plant cell, plant tissue, plant organ, or plant such that the gene is expressed at a higher rate, thereby generating more mRNA, which, in turn, is translated into more of the encoded protein.

As used herein "suppression" or "suppressing" means any of the well-known methods for suppressing a transcript or a protein from a gene including post-transcriptional gene suppression and transcriptional suppression. Post-transcriptional gene suppression is mediated by transcribed RNA having homology to a gene targeted for suppression. The RNA transcribed from the suppressing transgene preferably has a double stranded component to effect what is called RNA interference (RNAi). Transcriptional suppression is mediated by a transcribed double-stranded RNA having homology to promoter DNA sequence to effect what is called promoter trans-suppression.

More particularly, post-transcriptional gene suppression by double-stranded RNA can result from plant transformation with anti-sense DNA constructs as disclosed by Shewmaker et al. (U.S. Pat. Nos. 5,107,065 and 5,759,829), from plant transformation with a sense-oriented DNA construct as disclosed by Jorgensen et al. (U.S. Pat. Nos. 5,283,184 and 5,231,020), or with an RNAi construct as disclosed by Redenbaugh et al. (Safety Assessment of Genetically Engineered Flavr Savr™ Tomato, CRC Press, Inc., 1992), by Goldbach et al. (EP 0426195 A1, 1991), by Sijen et al. (*The Plant Cell*, 8:2277-2294, 1996), by Waterhouse et al. (WO 99/53050), by Graham et al. (WO 99/49029), by Lowe et al. (U.S. Application Publication No. 2003/0175965 A1), by Fillatti (U.S. patent application Ser. No. 10/465,800), by Plaetinck et al. (U.S. Application Publication No. 2003/0061626 A1), by Liu et al. (U.S. Pat. No. 6,326,193), by Agrawal et al. (WO 94/01550), by Werner et al. (WO 98/05770), by Oeller (U.S. Application Publication No. 2002/0048814 A1), by Gutterson et al. (U.S. Application Publication No. 2003/0018993 A1), and by Glassman et al.

(U.S. Application Publication No. 2003/0036197 A1). All of the above-described patents, applications, and international publications disclosing materials and methods for post-transcriptional gene suppression in plants are incorporated herein by reference.

Transcriptional suppression such as promoter trans-suppression can be effected by expressing a DNA construct comprising a promoter operably linked to inverted repeats of promoter DNA for a target gene. Constructs useful for such gene suppression mediated by promoter trans-suppression are disclosed by Mette et al., *The EMBO Journal*,18(1):241-148, 1999 and Mette et al., *The EMBO Journal*, 19(19): 5194-5201, 2000, both of which are incorporated herein by reference.

A preferred method of post-transcriptional gene suppression in plants employs either sense-oriented or antisense-oriented, transcribed RNA which is stabilized, e.g., with a terminal hairpin structure. A preferred DNA construct for effecting post-transcriptional gene suppression is transcribed to a segment of antisense oriented RNA having homology to a gene targeted for suppression, where the antisense RNA segment is followed-at the 3' end by a contiguous, complementary, shorter segment of RNA in the sense orientation. The use of self-stabilized antisense RNA oligonucleotides in plants is disclosed in WO 94/01550 (Agrawal et al.). See also WO 98/05770 (Werner et al.) where the antisense RNA is stabilized by hairpin forming repeats of poly(CG) nucleotides. See also U.S. Application Publication No. 2002/0048814 A1 (Oeller) where sense or antisense RNA is stabilized by a poly(T)-poly(A) tail. See also U.S. Application Publication No. 2003/0018993 A1 (Gutterson et al.) where sense or antisense RNA is stabilized by an inverted repeat of a subsequence of an NOS gene. See also U.S. Application Publication No. 2003/0036197 A1 (Glassman et al.) where RNA having homology to a target is stabilized by 2 complementary RNA regions. All of the above-described patents, applications, and international publications disclosing materials and methods for employing stabilized RNA and its use in gene suppression in plants are incorporated herein by reference.

Transcriptional suppression such as promoter trans-suppression can be effected by expressing a DNA construct comprising a promoter operably linked to inverted repeats of promoter DNA for a target gene. Constructs useful for such gene suppression mediated by promoter trans-suppression are disclosed by Mette et al., *The EMBO Journal*, 18(1):241-148, 1999 and Mette et al., *The EMBO Journal*, 19(19): 5194-5201, 2000, both of which are incorporated herein by reference.

Still yet another method is the use of a dominant negative mutant. For example, a dominant negative mutant of a polypeptide having CDK inhibitor-like activity as described herein can be generated by completely or partially deleting the C-terminal coding sequence, in particular all or part of the C-terminal coding sequence that is highly conserved among the polypeptides described herein. The resulting mutant can be operably linked to a promoter, such as an embryo-specific promoter from maize, for example, and cloned into a vector for introduction into a corn plant or part thereof. See, e.g., Jasinski et al., *Plant Physiol.*, 130:1871-1882 (2002)).

Ribozymes also have been reported to have use as a means to inhibit expression of endogenous plant genes (see, e.g., Merlo et al., *Plant Cell*, 10(10): 1603-1622 (1998)). It is possible to design ribozymes that specifically pair with virtually any target RNA and cleave the phosphodiester backbone at a specific location, thereby functionally inactivating the target RNA. In carrying out this cleavage, the ribozyme is not itself altered and is, thus, capable-of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature*, 334:585-591 (1988). Preferably, the ribozyme comprises at least about 20 continuous nucleotides complementary to the target sequence on each side of the active site of the ribozyme.

Alternatively, reverse genetics systems, which are well-known in the art, can be used to generate and isolate suppressed or null mutants. One such system, the Trait Utility System for Corn, i.e., TUSC, is based on successful systems from other organisms (Ballinger et al., *PNAS U.S.A.*, 86:9402-9406 (1989); Kaiser et al., *PNAS U.S.A.* 87:1686-1690 (1990); and Rushforth et al., *Mol. Cell. Biol.*, 13:902-910 (1993)). The central feature of the system is to identify Mu transposon insertions within a DNA sequence of interest in anticipation that at least some of these insertion alleles will be mutants. To develop the system in corn, DNA was collected from a large population of Mutator transposon stocks that were then self-pollinated to produce F2 seed. To find Mu transposon insertions within a specified DNA sequence, the collection of DNA samples is screened via PCR using a gene-specific primer and a primer that anneals to the inverted repeats of Mu transposons. A PCR product is expected only when the template DNA comes from a plant that contains a Mu transposon insertion within the target gene. Once such a DNA sample is identified, F2 seed from the corresponding plant is screened for a transposon insertion allele. Transposon insertion mutations of the an1 gene have been obtained via the TUSC procedure (Bensen et al., *Plant Cell*, 7:75-84 (1995)). This system is applicable to other plant species, at times modified as necessary in accordance with knowledge and skill in the art.

T-DNA insertional mutagenesis can be used to generate insertional mutations in one of the above-mentioned genes so as to affect adversely the expression of a given gene. T-DNA tagged lines of plants can be screened using PCR. For example, a primer can be designed for one end of the T-DNA and another primer can be designed for the gene of interest and both primers can be used in PCR. If no PCR product is obtained, then there is no insertion in the gene of interest. In contrast, if a PCR product is obtained, then there is an insertion in the gene of interest. Insertional mutations, however, often generate null alleles, which can be lethal. Alternatively, if there is more than one gene that encodes for a given enzyme, a mutation in one of the genes may not result in decreased expression of the enzyme encoded by the gene.

Another alternative method to decrease expression of a given gene is to use a compound that inhibits expression of one of the above-mentioned genes or that. inhibits the activity of the protein encoded by one of the above-mentioned genes. In this regard, x-ray or gamma radiation can be used as can chemical mutagens, such as ethyl methyl sulfonate (EMS) or dimethyl butyric acid (DMB).

In addition to the above, gene replacement technology can be used to increase or decrease expression of a given gene. Gene replacement technology is based upon homologous recombination (see, Schnable et al., *Curr. Opinions Plant Biol.*, 1:123 (1998)). The nucleic acid of the enzyme of interest can be manipulated by mutagenesis (e.g., insertions, deletions, duplications, or replacements) to either increase or decrease enzymatic function. The altered sequence can be introduced into the genome to replace the existing, e.g., wild-type, gene via homologous recombination (Puchta and Hohn, *Trends Plant Sci.*, 1:340 (1996); Kempin et al., *Nature*, 389:802 (1997)).

The activity of a given CDK inhibitor-like polypeptide can be measured in vitro. For example, the ability of a given CDK inhibitor-like polypeptide to prevent phosphorylation of H1 histones by CDK can be measured (see, e.g., Example 14).

Whether or not a given CDK inhibitor-like polypeptide affects the expression of other genes can be determined using a transgenic plant, for example. As microarray chip technology becomes established and available (DeRisi et al., *Science*, 278:680-686 (1997)), the effect of a given genetic alteration on the expression of all identified genes of maize can be determined using microarray chips. Metabolic radiotracer studies can be performed to measure the generation of different product pools in vivo. In such studies, radioactively labeled precursors are provided to intact tissues and the radioactive label is monitored as the precursor is metabolized. By comparing wild-type plants and plants that have reduced activities of one of the CDK inhibitor-like polypeptide genes, the effect of the reduction in a given CDK inhibitor-like polypeptide can be determined.

In view of the above, the present invention provides a host cell comprising an above-described isolated or purified nucleic acid molecule, optionally in the form of a vector. Suitable hosts include bacteria, yeast and plant cells, including *E. coli, B. subtilis, A. tumefaciens, S. cerevisiae,* and *N. crassa. E. coli* hosts include TB-1, TG-2, DH5α, XL-Blue MRF' (Stratagene, Austin, Tex.), SA2821, Y1090, and TG02. Plant cells include maize cells.

Also in view of the above, the present invention provides an isolated or purified polypeptide encoded by an above-described isolated or purified nucleic acid molecule. The polypeptide preferably comprises an amino end and a carboxyl end. The polypeptide can comprise D-amino acids, L-amino acids, or a mixture of D- and L-amino acids. The D-form of the amino acids, however, is particularly preferred, since a protein comprised of D-amino acids is expected to have a greater retention of its biological activity in vivo, given that the D-amino acids are not recognized by naturally occurring proteases.

Alterations of the native amino acid sequence to produce variant polypeptides can be done by a variety of means known to those ordinarily skilled in the art. For instance, amino acid substitutions can be conveniently introduced into the polypeptides at the time of synthesis. Alternatively, site-specific mutations can be introduced by ligating into an expression vector a synthesized oligonucleotide comprising the modified site. Alternately, oligonucleotide-directed, site-specific mutagenesis procedures can be used, such as disclosed in Walder et al., *Gene*, 42:133 (1986); Bauer et al., *Gene*, 37:73 (1985); and U.S. Pat. Nos. 4,518,584 and 4,737,462.

It is within the skill of the ordinary artisan to select synthetic and naturally-occurring amino acids that effect conservative or neutral substitutions for any particular naturally-occurring amino acids. The ordinarily skilled artisan desirably will consider the context in which any particular amino acid substitution is made, in addition to considering the hydrophobicity or polarity of the side-chain, the general size of the side chain and the pK value of side-chains with acidic or basic character under physiological conditions. For example, lysine, arginine, and histidine are often suitably substituted for each other, and more often arginine and histidine. As is known in the art, this is because all three amino acids have basic side chains, whereas the pK value for the side-chains of lysine and arginine are much closer to each other (about 10 and 12) than to histidine (about 6). Similarly, glycine, alanine, valine, leucine, and isoleucine are often suitably substituted for each other, with the proviso that glycine is frequently not suitably substituted for the other members of the group. This is because each of these amino acids is relatively hydrophobic when incorporated into a polypeptide, but glycine's lack of an α-carbon allows the phi and psi angles of rotation (around the α-carbon) so much conformational freedom that glycinyl residues can trigger changes in conformation or secondary structure that do not often occur when the other amino acids are substituted for each other. Other groups of amino acids frequently suitably substituted for each other include, but are not limited to, the group consisting of glutamic and aspartic acids; the group consisting of phenylalanine, tyrosine, and tryptophan; and the group consisting of serine, threonine, and optionally, tyrosine. Additionally, the ordinarily skilled artisan can readily group synthetic amino acids with naturally-occurring amino acids.

If desired, the polypeptides can be modified, for instance, by glycosylation, amidation, carboxylation, or phosphorylation, or by the creation of acid addition salts, amides, esters, in particular C-terminal esters, and N-acyl derivatives of the polypeptides of the invention. The polypeptides also can be modified to create protein derivatives by forming covalent or noncovalent complexes with other moieties in accordance with methods known in the art. Covalently-bound complexes can be prepared by linking the chemical moieties to functional groups on the side chains of amino acids comprising the polypeptides, or at the N- or C-terminus. Desirably, such modifications and conjugations do not adversely affect the activity of the polypeptides (and variants thereof). While such modifications and conjugations can have greater or lesser activity, the activity desirably is not negated and is characteristic of the unaltered polypeptide.

The polypeptides (and fragments, variants, and fusion proteins) can be prepared by any of a number of conventional techniques. The polypeptide can be isolated or purified from a naturally occurring source or from a recombinant source. For instance, in the case of recombinant proteins, a DNA fragment encoding a desired protein can be subcloned into an appropriate vector using well-known molecular genetic techniques (see, e.g., Maniatis et al., *Molecular Cloning: A Laboratory Manual*, 2nd ed. (Cold Spring Harbor Laboratory, 1989) and other references cited herein under "EXAMPLES"). The fragment can be transcribed and the protein subsequently translated in vitro. Commercially available kits also can be employed (e.g., such as manufactured by Clontech, Palo Alto, Calif.; Amersham Life Sciences, Inc., Arlington Heights, Ill.; InVitrogen, San Diego, Calif., and the like). The polymerase chain reaction optionally can be employed in the manipulation of nucleic acids.

Such polypeptides also can be synthesized using an automated peptide synthesizer in accordance with methods known in the art. Alternately, the polypeptide (and fragments, variants, and fusion proteins) can be synthesized using standard peptide synthesizing techniques well-known to those of ordinary skill in the art (e.g., as summarized in Bodanszky, *Principles of Peptide Synthesis*, (Springer-Verlag, Heidelberg: 1984)). In particular, the polypeptide can be synthesized using the procedure of solid-phase synthesis (see, e.g., Merrifield, *J. Am. Chem. Soc.*, 85:2149-54 (1963); Barany et al., *Int. J. Peptide Protein Res.*, 30:705-739 (1987); and U.S. Pat. No. 5,424,398). If desired, this can be done using an automated peptide synthesizer. Removal of the t-butyloxycarbonyl (t-BOC) or 9-fluorenylmethyloxycarbonyl (Fmoc) amino acid blocking groups and separation of the protein from the resin can be accomplished by, for example, acid treatment at reduced temperature. The polypeptide-containing mixture then can be extracted, for instance, with diethyl ether, to remove non-peptidic organic compounds, and the synthesized protein can be extracted from the resin powder (e.g., with about 25% w/v acetic acid). Following the synthesis of the polypeptide, further purification (e.g., using HPLC) optionally can be done in order to eliminate any incomplete proteins, polypeptides, peptides, or free amino acids. Amino acid and/or HPLC analysis can be performed on the synthesized polypeptide to validate its identity. For other applications according to the invention, it may be preferable to produce the polypeptide as part of a larger fusion protein, either by chemical conjugation, or through genetic means, such as are known to those ordinarily skilled in the art. In this regard, the present invention also provides a fusion protein comprising the isolated or purified polypeptide (or fragment thereof) or variant thereof and one or more other polypeptides/protein(s) having any desired properties or effector functions.

The nucleic acid molecules, vectors, and polypeptides can be used in agricultural methods and various screening assays (see, e.g., WO 02/28893 and U.S. Pat. No. 6,215,048). For example, a nucleic acid molecule can be used to express, e.g., via a vector, a CDK inhibitor-like polypeptide in a host cell, to detect mRNA encoding a CDK inhibitor-like polypeptide in a biological sample, to detect a genetic alteration in a gene encoding a CDK inhibitor-like polypeptide, such as via a Southern blot, to suppress a CDK inhibitor-like polypeptide, or to up-regulate a CDK inhibitor-like polypeptide so as to render a plant male-sterile or a dwarf, or to inhibit the formation of certain organs, for example. The polypeptides can be used to compensate for deficiencies in CDK inhibitor-like polypeptides or for the presence of mutated CDK inhibitor-like polypeptides having reduced or no activity in a maize plant, or to treat excessive levels of substrates, whether direct or indirect, for CDK inhibitor-like polypeptides in a maize plant. Alternatively, the polypeptides can be used to screen agents for the ability to modulate their activity.

In view of the above, the present invention provides various nucleic acid constructs, which can be used to suppress a CDK inhibitor-like polypeptide. In one embodiment, the nucleic acid construct comprises at least one transcribable nucleotide sequence, the expression of which results in the suppression of an endogenous nucleotide sequence selected from the group consisting of:

SEQ ID NO: 1 [ZmKRP1], a nucleotide sequence encoding the amino acid sequence of SEQ ID NO: 2 [ZmKRP1], SEQ ID NO: 3 [ZmKRP2], and a nucleotide sequence encoding the amino acid sequence of SEQ ID NO: 4 [ZmKRP2], alone or in further combination with at least one other transcribable nucleotide sequence, the expression of which results in the suppression of an endogenous nucleotide sequence selected from the group consisting of SEQ ID NO: 5 [ZmKRP3], a nucleotide sequence encoding the amino acid sequence of SEQ ID NO: 6 [ZmKRP3], SEQ ID NO: 7 [ZmKRP4], a nucleotide sequence encoding the amino acid sequence of SEQ ID NO: 8 [ZmKRP4], SEQ ID NO: 9 [ZmKRP5], a nucleotide sequence encoding. the amino acid sequence of SEQ ID NO: 10 [ZmKRP5], SEQ ID NO: 11 [ZmKRP6], a nucleotide sequence encoding the amino acid sequence of SEQ ID NO: 12 [ZmKRP6], SEQ ID NO: 13 [ZmKRP7], a nucleotide sequence encoding the amino acid sequence of SEQ ID NO: 14 [ZmKRP7], SEQ ID NO: 15 [ZmKRP8], a nucleotide sequence encoding the amino acid sequence of SEQ ID NO: 16 [ZmKRP8], SEQ ID NO: 17 [ZmKRP9], and a nucleotide sequence encoding the amino acid sequence of SEQ ID NO: 18 [ZmKRP9], wherein, when the nucleic acid construct comprises two or more transcribable nucleotide sequences, the nucleotide sequences can be present in any order on the nucleic acid construct and can be polycistronic, wherein each transcribable nucleotide sequence comprises at least about 100 (or 125, 150, 175, 200, 225, 250, 275, 300, 325, 375, 400, 425, 450, 500, 750, 1,000, 1,500, 2,000, or more) contiguous nucleotides, and wherein the expression of each transcribable nucleotide sequence optionally induces gene suppression. By "optionally" is meant that each transcribable nucleotide sequence, independent of any and all other nucleotide sequences present on the construct, either induces gene suppression or does not induce gene suppression.

Alternatively, the nucleic acid construct comprises transcribable nucleotide sequences, the expression of which results in the suppression of endogenous nucleotide sequences:

(i) SEQ ID NO: 1 [ZmKRP1] or a nucleotide sequence encoding the amino acid sequence of SEQ ID NO: 2 [ZmKRP1], (ii) SEQ ID NO: 3 [ZmKRP2] or a nucleotide sequence encoding the amino acid sequence of SEQ ID NO: 4 [ZmKRP2], (iii) SEQ ID NO: 5 [ZmKRP3] or a nucleotide sequence encoding the amino acid sequence of SEQ ID NO: 6 [ZmKRP3], (iv) SEQ ID NO: 7 [ZmKRP4] or a nucleotide sequence encoding the amino acid sequence of SEQ ID NO: 8 [ZmKRP4], (v) SEQ ID NO: 9 [ZmKRP5] or a nucleotide sequence encoding the amino acid sequence of SEQ ID NO: 10 [ZmKRP5], (vi) SEQ ID NO: 11 [ZmKRP6] or a nucleotide sequence encoding the amino acid sequence of SEQ ID NO: 12 [ZmKRP6], (vii) SEQ ID NO: 13 [ZmKRP7] or a nucleotide sequence encoding the amino acid sequence of SEQ ID NO: 14 [ZmKRP7], (viii) SEQ ID NO: 15 [ZmKRP8] or a nucleotide sequence encoding the amino acid sequence of SEQ ID NO: 16 [ZmKRP8], and (ix) SEQ ID NO: 17 [ZmKRP9] or a nucleotide sequence encoding the amino acid sequence of SEQ ID NO: 18 [ZmKRP9].

In another embodiment, the nucleic acid construct comprises at least one transcribable nucleotide sequence, the expression of which results in the suppression of an endogenous nucleotide sequence of SEQ ID NO: 7 [ZmKRP4] and/or SEQ ID NO: 17 [ZmKRP9], either one or both in further combination with at least one other transcribable nucleotide sequence, the expression of which results in the suppression of an endogenous nucleotide sequence selected from the group consisting of:

(i) SEQ ID NO: 1 [ZmKRP1] or a nucleotide sequence encoding the amino acid sequence of SEQ ID NO: 2 [ZmKRP2], (ii) SEQ ID NO: 3 [ZmKRP2] or a nucleotide sequence encoding the amino acid sequence of SEQ ID NO: 4 [ZmKRP2], (iii) SEQ ID NO: 5 [ZmKRP3] or a nucleotide sequence encoding the amino acid sequence of SEQ ID NO: 6

[ZmKRP3], provided that the transcribable nucleotide sequence does not entirely correspond to nucleotides 175-342 of SEQ ID NO: 5, (iv) SEQ ID NO: 9 [ZmKRP5] or a nucleotide sequence encoding the amino acid sequence of SEQ ID NO: 10 [ZmKRP5], provided that the transcribable nucleotide sequence does not entirely correspond to nucleotides 450-570 of SEQ ID NO: 9, (v) SEQ ID NO: 11 [ZmKRP6] or a nucleotide sequence encoding the amino acid sequence of SEQ ID NO: 12 [ZmKRP6], provided that the transcribable nucleotide sequence does not entirely correspond to nucleotides 380-765 of SEQ ID NO: 11, (vi) SEQ ID NO: 13 [ZmKRP7] or a nucleotide sequence. encoding the amino acid sequence of SEQ ID NO: 14 [ZmKRP7], provided that the transcribable nucleotide sequence does not entirely correspond to nucleotides 335-718 of SEQ ID NO: 13, and (vii) SEQ ID NO: 15 [ZmKRP8] or a nucleotide sequence encoding the amino acid sequence of SEQ ID NO: 16 [ZmKRP8], provided that the transcribable nucleotide sequence does not entirely correspond to nucleotides 350-405 or 420-698 of SEQ ID NO: 15, wherein the transcribable nucleotide sequences can be present in any order on the nucleic acid construct and can be polycistronic, wherein each transcribable nucleotide sequence comprises at least about 100 (or 125, 150, 175, 200, 225, 250, 275, 300, 325, 350, 375, 400, 425, 450, 475, 500, 750, 1,000, 1,500, 2,000, or more) contiguous nucleotides, and wherein the expression of each transcribable nucleotide sequence optionally induces gene suppression. As used herein, gene suppression refers to the reduction of gene expression through various techniques, including, but not limited to, sense suppression, antisense, dsRNA, and ribozyme technologies.

In yet another embodiment, the nucleic acid construct comprises at least one transcribable nucleotide sequence, the expression of which results in the suppression of an endogenous nucleotide sequence selected from the group consisting of:

(i) SEQ ID NO: 1 [ZmKRP1] or a nucleotide sequence encoding the amino acid sequence of SEQ ID NO: 2 [ZmKRP1], (ii) SEQ ID NO: 3 [ZmKRP2] or a nucleotide sequence encoding the amino acid sequence of SEQ ID NO: 4 [ZmKRP2], (iii) SEQ ID NO: 5 [ZmKRP3] or a nucleotide sequence encoding the amino acid sequence of SEQ ID NO: 6 [ZmKRP3], provided that the transcribable nucleotide sequence does not entirely correspond to nucleotides 175-342 of SEQ ID NO: 5, (iv) SEQ ID NO: 9 [ZmKRP5] or a nucleotide sequence encoding the amino acid sequence of SEQ ID NO: 10 [ZmKRP5], provided that the transcribable nucleotide sequence does not entirely correspond to nucleotides 450-570 of SEQ ID NO: 9, (v) SEQ ID NO: 11 [ZmKRP6] or a nucleotide sequence encoding the amino acid sequence of SEQ ID NO: 12 [ZmKRP6], provided that the transcribable nucleotide sequence of SEQ ID NO: 11 does not entirely correspond to nucleotides 380-765 of SEQ ID NO: 11, (vi) SEQ ID NO: 13 [ZmKRP7] or a nucleotide sequence encoding the amino acid sequence of SEQ ID NO: 14 [ZmKRP7], provided that the transcribable nucleotide sequence does not entirely correspond to nucleotides 335-718 of SEQ ID NO: 13, (vii) SEQ ID NO: 15 [ZmKRP8] or a nucleotide sequence encoding the amino acid sequence of SEQ ID NO: 16 [ZmKRP8], provided that the transcribable nucleotide sequence does not entirely correspond to nucleotides 350-405 or 420-698 of SEQ ID NO: 15, and (viii) SEQ ID NO: 17 [ZmKRP9] or a nucleotide sequence encoding the amino acid sequence of SEQ ID NO: 18 [ZmKRP9], provided that the transcribable nucleotide sequence does not entirely correspond to nucleotides 1-183 of SEQ ID NO: 17, wherein the transcribable nucleotide sequences can be present in any order on the nucleic acid construct and can be polycistronic, wherein each transcribable nucleotide sequence comprises at least about 100 (or 125, 150, 175, 200, 225, 250, 275, 300, 325, 350, 375, 400, 425, 450, 500, 750, 1,000, 1,500, 2,000, or more) contiguous nucleotides, and wherein the expression of each transcribable nucleotide sequence optionally induces gene silencing. By "does not entirely correspond" means that at least one, preferably at least about three nucleotides correspond to nucleotides outside of the designated ranges of nucleotides.

With respect to the above nucleic acid constructs, that at least one transcribable nucleotide sequence, the expression of which results in suppression, can be from a noncoding sequence. For example, the noncoding sequence can be an intron, a nucleotide sequence from a promoter region, a nucleotide sequence from a 5' untranslated region, a nucleotide sequence from a 3' untranslated region, or a fragment of any of the foregoing. Examples of such sequences include those of SEQ ID NOS: 44-58.

The above constructs are exemplary and are not intended to be limiting. In the suppression constructs, for example, ZmKRP1 or ZmKRP2 can be inhibited alone or together. In this regard, ZmKRP1 or ZmKRP2 can be inhibited alone or together, in further combination with any one of ZmKRP3, ZmKRP4, ZmKRP5, ZmKRP6, ZmKRP7, ZmKRP8, and ZmKRP9. For the sake of convenience, the abbreviation "ZmKRP" has been deleted from the following lists of combinations. For example, 1, 2 and 3; 1, 2 and 4; 1, 2 and 5; 1, 2 and 6; 1, 2 and 7; 1, 2 and 8; 1, 2 and 9; 1 and 3; 1 and 4; 1 and 5; 1 and 6; 1 and 7; 1 and 8; 1 and 9; 2 and 3; 2 and 4; 2 and 5; 2 and 6; 2 and 7; 2 and 8; 2 and 9; 1, 3 and 4; 1, 3 and 5; 1, 3 and 6; 1, 3 and 7; 1, 3 and 8; 1, 3 and 9; 2, 3 and 4; 2, 3 and 5; 2, 3 and 6; 2, 3 and 7; 2, 3 and 8; 2, 3 and 9; 1, 4 and 5; 1, 4 and 6; 1, 4 and 7; 1, 4 and 8; 1, 4 and 9; 1, 5 and 6; 1, 5 and 7; 1, 5 and 8; 1, 5 and 9; 2, 4 and 5; 2, 4 and 6; 2, 4 and 7; 2, 4 and 8; 2, 4 and 9; 1, 5 and 6; 1, 5 and 7; 1, 5 and 8; 1, 5 and 9; 2, 5 and 6; 2, 5 and 7; 2, 5 and 8; 2, 5 and 9; 1, 6 and 7; 1, 6 and 8; 1, 6 and 9; 2, 6 and 7; 2, 6 and 8; 2, 6 and 9; 1, 7 and 8; 1, 7 and 9; 2, 7 and 8; 2, 7 and 9; 1, 8 and 9; 2, 8 and 9; 1, 3, 4, and 5; 1, 3, 4, and 6; 1, 3, 4, and 7; 1, 3, 4, and 8; 1, 3, 4, and 9; 2, 3, 4, and 5; 2, 3, 4, and 6; 2, 3, 4, and 7; 2, 3, 4, and 8; 2, 3, 4, and 9; 1, 4, 5, and 6; 1, 4, 5, and 7; 1, 4, 5, and 8; 1, 4, 5, and 9; 2, 4, 5, and 7; 2, 4, 5, and 8; 2, 4, 5, and 9; 1, 5, 6, and 7; 1, 5, 6, and 8; 1, 5, 6, and 9; 2, 5, 6, and 7; 2, 5, 6, and 8; 2, 5, 6, and 9; 1, 6, 7, and 8; 1, 6, 7, and 9; 2, 6, 7, and 8; 2, 6, 7, and9; 1, 7, 8, and 9; 2, 7, 8, and 9; 1, 3, 4, 5, and 6; 1, 3, 4, 5, and 7; 1, 3, 4, 5, and 8; 1, 3, 4, 5, and 9; 2, 3, 4, 5, and 6; 2, 3, 4, 5, and 7; 2, 3, 4, 5, and 8; 2, 3, 4, 5, and 9; 1, 3, 4, 5, 6, and 7; 1, 3, 4, 5, 6, and 8; 1, 3, 4, 5, 6, and 9; 2, 3, 4, 5, 6, and 7; 2, 3, 4, 5, 6, and 8; 2, 3, 4, 5, 6, and 9; 1, 3, 4, 5, 6, 7, and 8; 1, 3, 4, 5, 6, 7, and 9; 2, 3, 4, 5, 6, 7, and 8; 2, 3, 4, 5, 6, 7, and 9; 1, 3, 4, 5, 6, 7, 8, and 9; 2, 3, 4, 5, 6, 7, 8, and 9; 1, 2, 3, and 4; 1, 2, 3, and 5; 1, 2, 3, and 6; 1, 2, 3, and 7; 1, 2, 3, and 8; 1, 2, 3, and 9; 1, 2, 4, and 5; 1, 2, 4, and 6; 1, 2, 4, and 7; 1, 2, 4, and 8; 1, 2, 4, and 9; 1, 2, 5, and 6; 1, 2, 5, and 7; 1, 2, 5, and 8; 1, 2, 5, and 9; 1, 2, 6, and 7; 1, 2, 6, and 8; 1, 2, 6, and 9; 1,2,7, and 8; 1, 2, 7, and 9; 1, 2, 8, and 9; 1, 2, 3, 4, and 5; 1, 2, 3, 4, and 6; 1, 2, 3, 4, and 7; 1, 2, 3, 4, and 8; 1, 2, 3, 4, and 9; 1, 2, 4, 5, and 6; 1, 2, 4, 5, and 7; 1, 2, 4, 5, and 8; 1, 2, 4, 5, and 9; 1, 2, 5, 6, and 7; 1, 2, 5, 6, and 8; 1, 2, 5, 6, and 9; 1, 2, 6, 7, and 8; 1, 2, 6, 7, and 9; 1, 2, 7, 8, and 9; 1, 2, 3, 4, 5, and 6; 1, 2, 3, 4, 5, and 7; 1, 2, 3, 4, 5, and 8; 1, 2, 3, 4, 5, and 9; 1, 2, 3, 4, 5, 6, and 7; 1, 2, 3, 4, 5, 6, and 8; 1, 2, 3, 4, 5, 6, and 9; 1, 2, 3, 4, 5, 6, 7, and 8; 1, 2, 3, 4, 5, 6, 7, and 9; or 1, 2, 3, 4, 5, 6, 7, 8, and 9 can be inhibited. Furthermore, the constructs can comprise the nucleotide sequences in any order. The nucleotide sequences can also vary in length.

In the suppression constructs, ZmKRP4 or ZmKRP9 can be inhibited alone or together. In this regard, ZmKRP4 or ZmKRP9 can be inhibited alone or together, in further combination with any one of ZmKRP1, ZmKRP2, ZmKRP3, ZmKRP5, ZmKRP6, ZmKRP7, and ZmKRP8. For example, 4 and 1; 4 and 2; 4 and 3; 4 and 5; 4 and 6; 4 and 7; 4 and 8; 4, 1 and 2; 4, 1 and 3; 4, 1 and 5; 4, 1 and 6; 4, 1 and 7; 4, 1 and 8; 4, 1, 2 and 3; 4, 1, 2, and 5; 4, 1, 2, and 6; 4, 1, 2, and 7; 4, 1, 2, and 8; 4, 1, 2, 3, and 5; 4, 1, 2, 3, and 6; 4, 1, 2, 3, and 7; 4, 1, 2, 3, and 8; 4, 1, 2, 3, 5, and 6; 4, 1, 2, 3, 5, and 7; 4, 1, 2, 3, 5, and 8; 4, 1, 2, 3, 5, 6, and 7; 4, 1, 2, 3, 5, 6, and 8; 4, 1, 2, 3, 5, 6, 7, and 8; 4, 2and 3; 4, 2and 5; 4, 2 and 6; 4, 2 and 7; 4, 2 and 8; 4, 3 and 5; 4, 3 and 6; 4, 3 and 7; 4, 3 and 8; 4, 5 and 6; 4, 5 and 7; 4, 5 and 8; 4, 6 and 7; 4, 6 and 8; 4, 7 and 8; 4, 2, 3, and 5; 4, 2, 3, and 6; 4, 2, 3, and 7; 4, 2, 3, and 8; 4, 3, 5, and 6; 4, 3, 5, and 7; 4, 3, 5, and 8; 4, 3, 6, and 7; 4, 3, 6, and 8; 4, 5, 6, and 7; 4, 5, 6, and 8; 4, 6, 7, and 8; 4, 2, 3, 5, and 6; 4, 2, 3, 5, and 7; 4, 2, 3, 5, and 8; 4, 2, 3, 5, 6, and 7; 4, 2, 3, 5, 6, and 8; 4, 2, 3, 5, 6, 7, and 8; 9 and 1; 9 and 2; 9 and 3; 9 and 5; 9 and 6; 9and 7; 9and 8; 9, 1 and 2; 9, 1 and 3; 9, 1 and 5; 9, 1 and 6; 9, 1 and 7; 9, 1 and 8; 9, 1, 2, and 3; 9, 1, 2, and 5; 9, 1, 2, and 6; 9, 1, 2, and 7; 9, 1, 2, and 8; 9, 1, 2, 3, and 5; 9, 1, 2, 3, and 6; 9, 1, 2, 3, and 7; 9, 1, 2, 3, and 8; 9, 1, 2, 3, 5, and 6; 9, 1, 2, 3, 5, and 7; 9, 1, 2, 3, 5, and 8; 9, 1, 2,3, 5,6, and 7; 9, 1, 2, 3, 5, 6, and 8; 9, 1, 2, 3, 5, 6, 7, and 8; 9, 2 and 3; 9, 2 and 5; 9, 2 and 6; 9, 2 and 7; 9, 2 and 8; 9, 3 and 5; 9, 3 and 6; 9, 3 and 7; 9, 3 and 8; 9, 5 and 6; 9, 5, and 7; 9, 5, and 8; 9, 6 and 7; 9, 6 and 8; 9, 7 and 8; 9, 2, 3, and 5; 9, 2, 3, and 6; 9, 2, 3, and 7; 9, 2, 3, and 8; 9, 3, 5, and 6; 9, 3, 5, and 7; 9, 3, 5, and 8; 9, 3, 6, and 7; 9, 3, 6, and 8; 9, 5, 6, and 7; 9, 5, 6 and 8; 9, 6, 7, and 8; 9, 2, 3, 5, and 6; 9, 2, 3, 5, and 7; 9, 2, 3, 5, and 8; 9, 2, 3, 5, 6, and 7; 9, 2, 3, 5, 6, and 8; 9, 2, 3, 5, 6, 7, and 8; 4, 9 and 1; 4, 9 and 2; 4, 9 and 3; 4, 9 and 5; 4, 9 and 6; 4, 9 and 7; 4, 9 and 8; 4, 9, 1, and 2; 4, 9, 1, and 3; 4, 9, 1, and 5; 4, 9, 1, and 6; 4, 9, 1, and 7; 4, 9, 1, and 8; 4, 9, 1, 2, and 3; 4, 9, 1, 2, and 5; 4, 9, 1, 2, and 6; 4, 9, 1, 2, and 7; 4, 9, 1, 2, and 8; 4, 9, 1, 2, 3, and 5; 4, 9, 1, 2, 3, and 6; 4, 9, 1, 2, 3, and 7; 4, 9, 1, 2, 3, and 8; 4, 9, 1, 2, 3, 5, and 6; 4, 9, 1, 2, 3, 5, and 7; 4, 9, 1, 2, 3, 5, and 8; 4, 9, 1, 2, 3, 5, 6, and 7; 4, 9, 1, 2, 3, 5, 6, and 8; 4, 9, 1, 2, 3, 5, 6, 7, and 8; 4, 9, 2, and 3; 4, 9, 2, and 5; 4, 9, 2, and 6; 4, 9, 2, and 7; 4, 9, 2, and 8; 4, 9, 3, and 5; 4, 9, 3, and 6; 4, 9, 3, and 7; 4, 9, 3, and 8; 4, 9, 5, and 6; 4, 9, 5, and 7; 4, 9, 5, and 8; 4, 9, 6, and 7; 4, 9, 6, and 8; 4, 9, 7, and 8; 4, 9, 2, 3, and 5; 4, 9, 2, 3, and 6; 4, 9, 2 3, and 7; 4, 9, 2, 3, and 8; 4, 9, 3, 5, and 6; 4, 9, 3, 5, and 7; 4, 9, 3, 5, and 8; 4, 9, 3, 6, and 7; 4, 9, 3, 6, and 8; 4, 9, 5, 6, and 7; 4, 9, 5, 6, and 8; 4, 9, 6, 7, and 8; 4, 9, 2, 3, 5, and 6; 4, 9, 2, 3, 5, and 7; 4, 9, 2, 3, 5, and 8; 4, 9, 2, 3, 5, 6, and 7; 4, 9, 2, 3, 5, 6, and 8; or 4, 9, 2, 3, 5, 6, 7, and 8 can be inhibited.

Furthermore, the constructs can comprise the nucleotide sequences in any order. The nucleotide sequences can also vary in length.

Any of the above constructs can further comprise a promoter, which is preferentially or specifically expressed in the germ and/or aleurone of a kernel of maize and the promoter is operably linked to at least one nucleotide sequence. The promoter can be an oleosin promoter, such as L3, a globulin promoter, or a Per1 promoter, for example. In the above suppression constructs, the at least one transcribable nucleotide sequence, the expression of which results in suppression, may be a noncoding sequence. The noncoding sequence can be an intron, a nucleotide sequence from a promoter region, a nucleotide sequence from a 5' untranslated region, a nucleotide sequence from a 3' untranslated region, or a fragment of any of the foregoing. Examples of such sequences include those of SEQ ID NOS: 44-58.

The above constructs can be made in accordance with methods known in the art (see, in general, "Recombinant DNA Part D," *Methods in Enzymology*, Vol. 153, Wu and Grossman, eds., Academic Press (1987) and the references cited herein under "EXAMPLES"). Suitable methods of construction are exemplified in the Examples set forth herein.

Techniques for contacting a plant cell, a plant tissue, a plant organ or a plant with a nucleic acid construct, such as a vector, so that the nucleic acid construct is taken up by a plant cell, alone or as part of a plant tissue, a plant organ, or a plant, and expressed therein are known in the art. Such methods involve plant tissue culture techniques, for example. Herein, "contacting" is intended to mean that the cell, tissue, organ, or plant is brought into contact with the nucleic acid construct or vector in such a manner that the vector enters the cell and is expressed therein.

The plant cell, plant tissue, plant organ, or plant can be contacted with the vector by any suitable means as known in the art. Preferably, a transgenic plant expressing the desired protein is to be produced. Various methods for the introduction of a desired polynucleotide sequence encoding the desired protein into plant cells include, but are not limited to: (1) physical methods such as microinjection (Capecchi, *Cell*, 22(2):479-488 (1980)), electroporation (Fromm et al., *PNAS U.S.A.*, 82(17):5824-5828 (1985); U.S. Pat. No. 5,384,253) and microprojectile mediated delivery (biolistics or gene gun technology) (Christou et al., *Bio/Technology*, 9:957 (1991); Fynan et al., *PNAS U.S.A.* 90(24):11478-11478 (1993)); (2) virus mediated delivery methods (Clapp, *Clin. Perinatol.*, 20(1): 155-168 (1993); Lu et al., *J. Exp. Med.*, 178(6):2089-2096 (1993); Eglitis and Anderson, *Biotechniques*, 6(7):608-614 (1988); and (3) *Agrobacterium*-mediated transformation methods; (Fraley et al., *PNAS U.S.A.*, 80:4803 (1983).

The most commonly used methods for transformation of plant cells are the *Agrobacterium*-mediated DNA transfer process) and the biolistics or microprojectile bombardment mediated process (i.e., the gene gun). *Agrobacterium*-mediated transformation is achieved through the use of a genetically engineered soil bacterium belonging to the genus *Agrobacterium*. Several *Agrobacterium* species mediate the transfer of a specific DNA known as "T-DNA," which can be genetically engineered to carry any desired piece of DNA into many plant species. The major events marking the process of T-DNA mediated pathogenesis are: induction of virulence genes, processing and transfer of T-DNA. This process is the subject of many reviews (Ream, *Ann. Rev. Phytopathol.*, 27:583-618 (1989); Howard and Citovsky, *Bioassays*, 12:103-108 (1990); Kado, *Crit. Rev. Plant Sci.*, 10: 1-32 (1991); Zambryski, *Annual Rev. Plant Physiol. Plant Mol. Biol.*, 43:465-490 (1992); Gelvin, In Transgenic Plants, Kung and Wu, eds., Academic Press, San Diego, pp. 49-87 (1993); Binns and Howitz, In *Bacterial Pathogenesis of Plants and Animals* (Dang, ed.). Berlin: Springer Verlag, pp. 119-138 (1994); Hooykaas and Beijersbergen, *Ann. Rev. Phytopathol.*, 32:157-179 (1994); Lessl and Lanka, *Cell*, 77:321-324 (1994); and Zupan and Zambryski, *Annual Rev. Phytopathol.*, 27:583-618 (1995)).

*Agrobacterium*-mediated genetic transformation of plants involves several steps. The first step, in which the virulent *Agrobacterium* and plant cells are first brought into contact with each other, is generally called "inoculation." The *Agrobacterium*-containing solution is then removed from contact with the explant by draining or aspiration. Following the inoculation, the *Agrobacterium* and plant cells/tissues are permitted to be grown together for a period of several hours to several days or more under conditions suitable for growth and T-DNA transfer. This step is termed "co-culture." Following co-culture and T-DNA delivery, the plant cells are treated with bactericidal or bacteriostatic agents to kill the *Agrobacterium* remaining in contact with the explant and/or in the vessel containing the explant. If this is done in the absence of any selective agents to promote preferential growth of transgenic versus non-transgenic plant cells, then this is typically referred to as the "delay"-step. If done in the presence of selective pressure favoring transgenic plant cells, then it is referred to as a "selection" step. When a "delay" is used, it is typically followed by one or more "selection" steps. Both the "delay" and "selection" steps typically include bactericidal or bacteriostatic agents to kill any remaining *Agrobacterium* cells because the growth of *Agrobacterium* cells is undesirable after the infection (inoculation and co-culture) process.

A number of wild-type and disarmed strains of *Agrobacterium tumefaciens* and *Agrobacterium rhizogenes* harboring Ti or Ri plasmids can be used for gene transfer into plants. The *Agrobacterium* hosts contain disarmed Ti and Ri plasmids that do not contain the oncogenes that cause tumorigenesis or rhizogenesis, respectively, which are used as the vectors and contain the genes of interest that are subsequently introduced into plants. Preferred strains include, but are not limited to, *Agrobacterium tumefaciens* strain C58, a nopaline-type strain that is used to mediate the transfer of DNA into a plant cell, octopine-type strains such as LBA4404 or succinamopine-type strains, e.g., EHA101 or EHA105. The nucleic acid molecule, prepared as a DNA composition in vitro, is introduced into a suitable host such as *E. coli* and mated into the *Agrobacterium*, or directly transformed into competent *Agrobacterium*. These techniques are well-known to those of skill in the art.

The *Agrobacterium* can be prepared either by inoculating a liquid such as Luria Burtani (LB) media directly from a glycerol stock or streaking the *Agrobacterium* onto a solidified media from a glycerol stock, allowing the bacteria to grow under the appropriate selective conditions, generally from about 26° C.-30° C., or about 28° C., and taking a single colony or a small loop of *Agrobacterium* from the plate and inoculating a liquid culture medium containing the selective agents. Those of skill in the art are familiar with procedures for growth and suitable culture conditions for *Agrobacterium* as well as subsequent inoculation procedures. The density of the *Agrobacterium* culture used for inoculation and the ratio of *Agrobacterium* cells to explant can vary from one system to the next, and, therefore, optimization of these parameters for any transformation method is expected.

Typically, an *Agrobacterium* culture is inoculated from a streaked plate or glycerol stock and is grown overnight and the bacterial cells are washed and resuspended in a culture medium suitable for inoculation of the explant.

With respect to microprojectile bombardment (U.S. Pat. Nos. 5,550,318; 5,538,880; 5,610,042; and WO 95/06128; each of which is specifically incorporated herein by reference in its entirety), particles are coated with nucleic acids and delivered into cells by a propelling force. Exemplary particles include those comprised of tungsten, platinum, and preferably, gold. It is contemplated that, in some instances, DNA precipitation onto metal particles would not be necessary for DNA delivery to a recipient cell using microprojectile bombardment. However, it is contemplated that particles can contain DNA, rather than be coated with DNA. Hence, it is proposed that DNA-coated particles can increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and can be used to transform virtually any plant species. Examples of species that have been transformed by microprojectile bombardment include monocot species, such as maize (WO 95/06128), barley, wheat (U.S. Pat. No. 5,563,055, specifically incorporated herein by reference in its entirety), rice, oat, rye, sugarcane, and sorghum; as well as a number of dicots including tobacco, soybean (U.S. Pat. No. 5,322,783, specifically incorporated herein by reference in its entirety), sunflower, peanut, cotton, tomato, and legumes in general (U.S. Pat. No. 5,563,055, specifically incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker include, but are not limited to, GUS, green fluorescent protein (GFP), luciferase (LUX), antibiotic or herbicide tolerance genes. Examples of antibiotic resistance genes include the penicillins, kanamycin (and neomycin, G418, and bleomycin); methotrexate (and trimethoprim); chloramphenicol; kanamycin and tetracycline.

Particularly preferred selectable marker genes for use in the present invention include genes that confer resistance to compounds such as antibiotics, like kanamycin (nptII), hygromycin B (aph IV), and gentamycin (aac3 and aacC4) (Dekeyser et al., *Plant Physiol.*, 90:217-223 (1989)), and herbicides, like glyphosate (Della-Cioppa et al., *Bio/Technology*, 5:579-584 (1987)). Other selection devices also can be implemented including, but not limited to, tolerance to phosphinothricin, bialaphos, and positive-selection mechanisms (Joersbo et al., *Mol. Breed.*, 4:111-117 (1998)) and are considered within the scope of the present invention.

Transformed plant cells, which are derived by any of the above transformation techniques, can be cultured to regenerate a whole plant, which possesses the desired transformed phenotype. Any suitable plant culture medium can be used. Examples of suitable media would include but are not limited to MS-based media (Murashige and Skoog, *Physiol. Plant*, 15:473-497, 1962) or N6-based media (Chu et al., *Scientia Sinica*, 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

In view of the foregoing, the present invention provides a method of suppressing the expression of one or more CDK inhibitor-like genes in a maize cell, a maize tissue, a maize organ, or a maize plant. The method comprises contacting said maize cell, maize tissue, maize organ, or maize plant with a nucleic acid construct as described above.

Thus, the present invention further provides a maize cell, a maize tissue, a maize organ, or a maize plant in which the expression of a CDK inhibitor-like gene has been suppressed in accordance with such a method. Also provided is a seed obtained from such a plant and the oil and meal obtained from such a seed.

The present invention also provides a container of over about 10,000, more preferably about 20,000, and even more preferably about 40,000 seeds where over about 10%, more preferably about 25%, more preferably about 50%, and even more preferably about 75% or more preferably about 90% of the seeds are seeds derived from a plant of the present invention.

The present invention also provides a container of over about 10 kg, more preferably about 25 kg, and even more preferably about 50 kg seeds where over about 10%, more preferably about 25%, more preferably about 50%, and even more preferably about 75% or more preferably about 90% of the seeds are seeds derived from a plant of the present invention.

Any of the plants or parts thereof of the present invention may be processed to produce a feed, meal, protein, or oil preparation. A particularly preferred plant part for this purpose is a seed. In a preferred embodiment the feed, meal, protein, or oil preparation is designed for ruminant animals. Methods to produce feed, meal, protein, and oil preparations are known in the art. See, for example, U.S. Pat. Nos. 4,957,748; 5,100,679; 5,219,596; 5,936,069; 6,005,076; 6,146,669; and 6,156,227. In a preferred embodiment, the protein preparation is a high protein preparation. Such a high protein preparation preferably has a protein content of greater than 5% w/v, more preferably 10% w/v, and even more preferably 15% w/v.

In a further embodiment, meal of the present invention may be blended with other meals. In a preferred embodiment, the meal produced from plants of the present invention or generated by a method of the present invention constitutes greater than about 0.5%, about 1%, about 5%, about 10%, about 25%, about 50%, about 75%, or about 90% by volume or weight of the meal component of any product. In another embodiment, the meal preparation may be blended and can constitute greater than about 10%, about 25%, about 35%, about 50%, or about 75% of the blend by volume.

The present invention further provides a method of up-regulating the expression of one or more CDK inhibitor-like genes in a maize cell, a maize tissue, a maize organ, or a maize plant. The method comprises contacting a maize cell, tissue, organ, or plant with at least one nucleic acid construct comprising at least one nucleotide sequence selected from the group consisting of SEQ ID NO: 1 [ZmKRP1], a nucleotide sequence encoding the amino acid sequence of SEQ ID NO: 2 [ZmKRP1], SEQ ID NO: 3 [ZmKRP2], a nucleotide sequence encoding the amino acid sequence of SEQ ID NO: 4 [ZmKRP2], SEQ ID NO: 7 [ZmKRP4], a nucleotide sequence encoding the amino acid sequence of SEQ ID NO: 8 [ZmKRP4], SEQ ID NO: 9 [ZmKRP5], a nucleotide sequence encoding the amino acid sequence of SEQ ID NO: 10 [ZmKRP5], SEQ ID NO: 11 [ZmKRP6], and a nucleotide sequence encoding the amino acid sequence of SEQ ID NO: 12 [ZmKRP6], wherein, when a cell, tissue, or organ is contacted with the nucleic acid construct, the method further comprises generating a plant from the cell, tissue, or organ, whereupon the expression of one or more CDK inhibitor-like genes is up-regulated in a maize cell, tissue, organ, or plant. The method can comprise contacting the cell, tissue, organ, or plant with more than one nucleic acid construct and each nucleic acid construct comprises a different nucleotide sequence. The nucleic acid can comprise a promoter that is preferentially expressed in the male reproductive tissue of maize, wherein the promoter is operably linked to the at least one nucleotide sequence. An example of such a promoter is the SILKY1 promoter of maize and others as described herein above. Preferential expression in the male reproductive tissue of maize can result in the generation of a male-sterile maize plant.

EXAMPLES

The present invention is described further in the context of the following examples. These examples serve to illustrate further the present invention and are not intended to limit the scope of the invention.

Example 1

This example describes the identification of CDK inhibitors from maize.

Initial tBLASTn searches (Altschul et al., *Nuc. Acid Res.*, 25:3389-3402 (1997)) of Monsanto's proprietary EST database were performed using publicly available sequences of *Arabidopsis* CDK inhibitor-like genes AtKRP1 ("At" indicates *Arabidopsis thaliana*; KRP1 is as defined above; GenBank #AAC49698), AtKRP2 (GenBank #CAB76424), AtKRP3 (GenBank #CAC41617), AtKRP4 (GenBank #CAC41618), AtKRP5 (GenBank #CAC41619), AtKRP6 (GenBank #CAC41620), and AtKRP7 (GenBank #CAC41621). Additionally, the following conserved sequence from the C-terminal region of the above polypeptides was used in a tBLASTn search:

(PTTAEIEDFFSEAEEQQQKQFIEKYN-FDIVNDEPLEGRYEWVKLKP) [SEQ ID NO: 59].

Resulting from the BLAST searches, seven maize sequence clusters were identified as having homology to the above-mentioned *Arabidopsis* CDK inhibitor-like genes. As used herein, "sequence clusters" refer to a group of EST sequences with overlapping regions of homology. Representative clones from each cluster were full-length double-strand sequenced and were used to BLAST search against Monsanto proprietary EST databases. An additional 2 clusters were identified from this second BLAST search and the representative clones were full-length double-strand sequenced. DNA sequence analysis indicated the presence of at least 9 different CDK inhibitor-like clusters in maize. These 9 clusters and their representative clones (named ZmKRP1 through ZmKRP9) are summarized in Table 1.

TABLE 1

Maize CDK inhibitor-like clusters and representative EST clones and ORF SEQ ID NO:

| CLUSTER ID | SELECTED CLONE ID | Description | ORF SEQ ID NO: |
|---|---|---|---|
| ZEAMA-21JUN01-CLUSTER89801_1 | LIB3732-047-Q1-N6-G6 | ZmKRP1 | 1 |
| ZEAMA-04OCT00-CLUSTER67903_1 | LIB3279-047-P1-K1-A7 | ZmKRP2 | 3 |
| ZEAMA-21JUN01-CLUSTER115879_1 | LIB3606-029-Q1-K6-B4 | ZmKRP3 | 5 |
| ZEAMA-21JUN01-CLUSTER31652_2 | LIB4759-013-R1-K1-B5 | ZmKRP4 | 7 |
| ZEAMA-06JUN02-CLUSTER620952_1 | LIB3898-003-Q1-N6-D10 | ZmKRP5 | 9 |
| ZEAMA-21JUN01-CLUSTER301_55 | LIB143-038-Q1-E1-G6 | ZmKRP6 | 11 |
| ZEAMA-21JUN01-CLUSTER301_41 | 700088048H1 | ZmKRP7 | 13 |
| ZEAMA-21JUN01-CLUSTER301_46 | LIB3587-222-Q1-K6-H9 | ZmKRP8 | 15 |
| ZEAMA-08NOV01-CLUSTER33142_4 | LIB4574-012-Q1-K1-H11 | ZmKRP9 | 17 |

Coding regions and deduced amino acid sequences of the representative clones of these 9 clusters are shown in the sequence listing as SEQ ID NOs: 1-18. Full-length open reading frames (ORFs) were identified for ZmKRP1, 2, 4, 5, and 6, while partial ORFs were identified for ZmKRP3, 7, 8, and 9.

Figure 1:
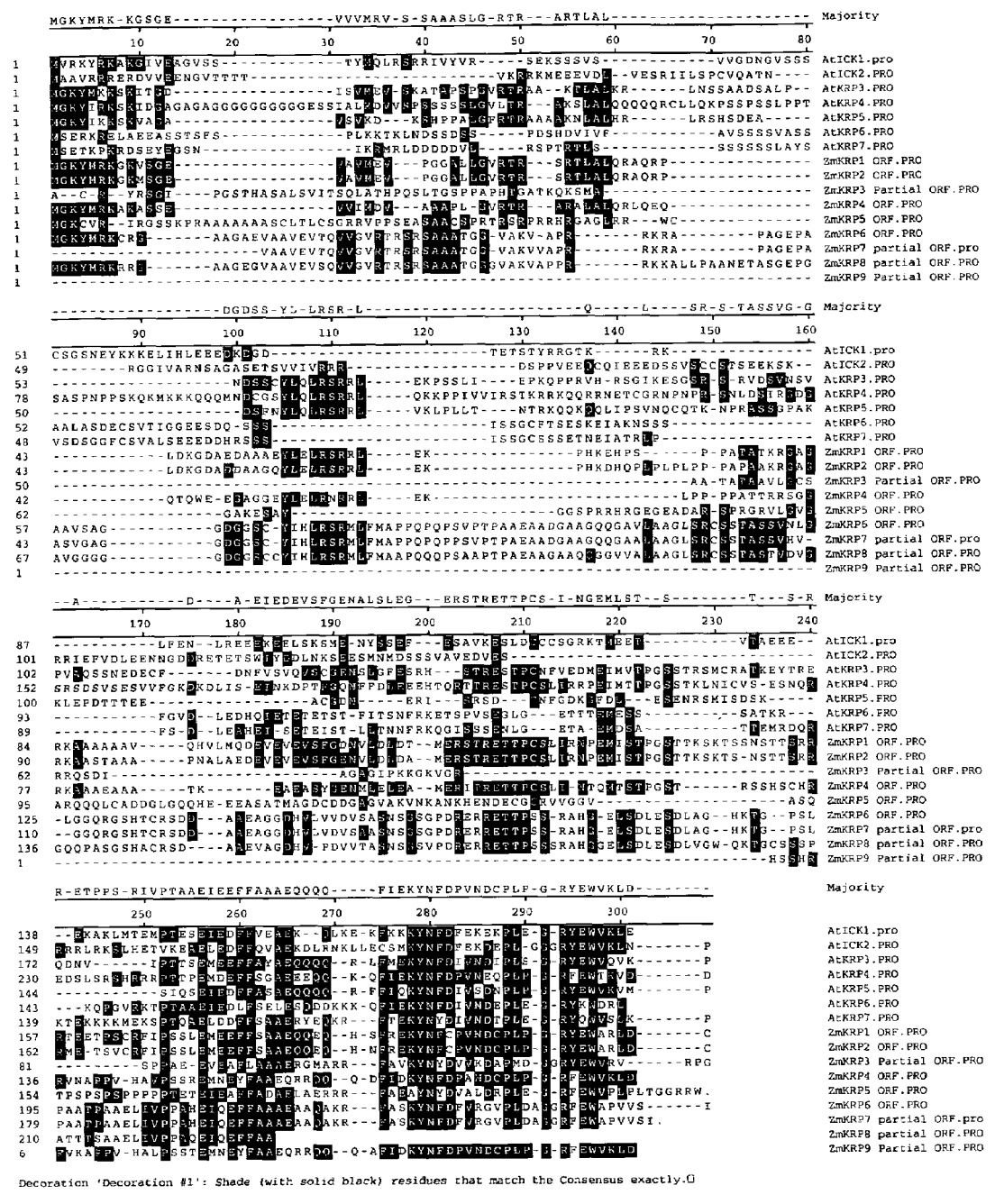

Protein sequence alignments indicated that maize KRPs share small conserved regions with *Arabidopsis* ICK/KRPs, especially at the C-terminal regions (FIG. 1). Additionally, some maize KRPs had high sequence identity to each other. For example, ZmKRP6 and ZmKRP7 were 90% identical, while ZmKRP1 and ZmKRP2 were 84% identical. Other ZmKRP members shared only 16-50% identity.

Sequence alignments and percent identity calculations were performed by the Clustal W Algorithm.

Example 2

This example describes the identification of CDK inhibitors targeted for suppression in corn embryos.

The Monsanto proprietary corn cDNA database was queried using DNA sequences from the maize KRP coding regions identified in Example 1 (SEQ ID NOs: 1, 3, 5, 7, 9, 11, 13, 15, and 17) using the CDK BLASTn protocol. This was done to determine which sequences were represented in cDNA libraries from developing kernel/embryo tissues, as well as various non-kernel tissues. cDNA sequences corresponding to ZmKRP1, ZmKRP2, ZmKRP4, ZmKRP6, ZmKRP7, and ZmKRP9 (SEQ ID NOs: 1, 2, 4, 6, 7, and 9) were identified in kernel or embryo cDNA libraries. cDNA sequences corresponding to ZmKRP3, ZmKRP5, and ZmKRP8 were found only in libraries generated from non-kernel libraries. These results indicated that at least the group of genes represented by the sequences found in the kernel or embryo cDNA libraries needed to be targeted for suppression. However, failure to identify cDNA sequences corresponding to a given gene in kernel libraries does not preclude the possibility of kernel expression, as a sequence may not be represented in a given library. Because all 9 genes may be expressed in the embryo, all were targeted for suppression using a dsRNA suppression construct.

Example 3

This example describes the construction of vectors for the tissue-specific suppression of the ZmKRP genes and the transformation of corn plants with these vectors.

To suppress the 9 maize CDK inhibitor-like genes identified in Example 1, a dsRNA strategy was used. To build the dsRNA construct to suppress all 9 ZmKRP genes (ZmKRP 1-9), 200 base pair fragments (F) were selected from the 3' end region of each gene (F1 to F7, SEQ ID NOs: 19 to 25), except for ZmKRP9, where 183 base pairs were selected (SEQ ID NO: 26) and connected in a polycistronic fashion. Since ZmKRP6 and ZmKRP7 are identical in this 3' 200 base pair region, one fragment was used to target suppression of both genes (F6). To make the final corn expression construct, two intermediate constructs were first generated. The construction of the 2 intermediate dsRNA constructs is shown schematically in FIGS. 4 and 5.

Each intermediate dsRNA construct contained 4 of the 3'-end fragments in both the sense and antisense orientation separated by an intervening intron region. The first intermediate construct contained the F1 through F4 sequences, and the second contained sequences F5 through F8. The two stem-loop structures, with respective promoters and 3' UTRs, were combined in one corn expression vector (FIG. 2) and used for corn transformation using the *Agrobacterium* transformation method described in Example 10.

Figure 4:
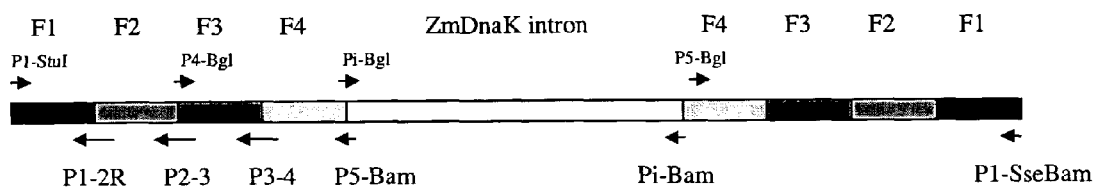
FIG. 4 is a schematic diagram of a dsRNA intermediate construct showing the primer regions and directions (A) and the assembling procedures (B).
Figure 4:
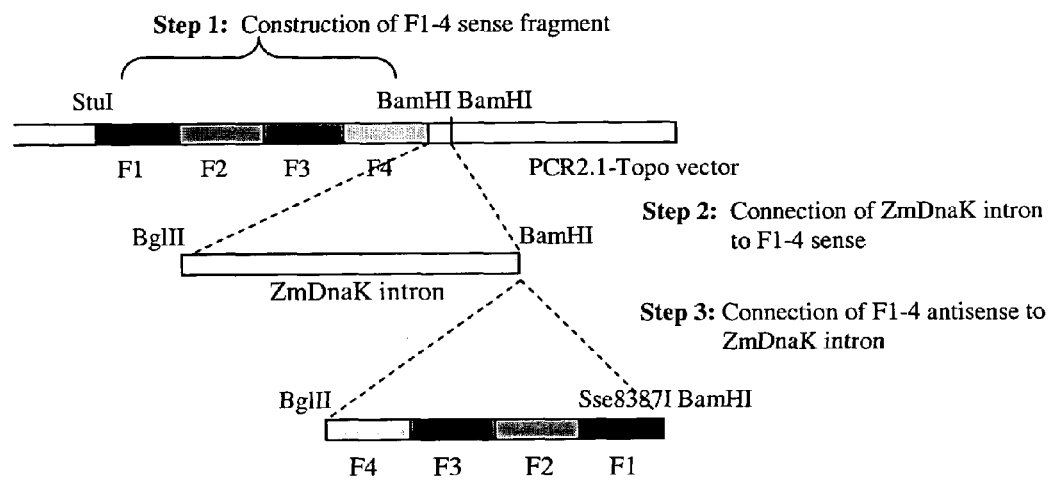
Figure 5:
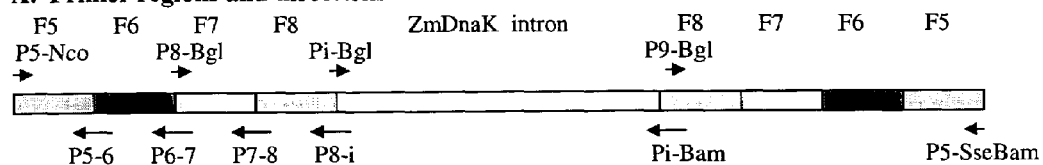
FIG. 5 is a schematic diagram of a dsRNA intermediate construct showing the primer regions and directions (A) and the assembling procedures (B).
Figure 5:
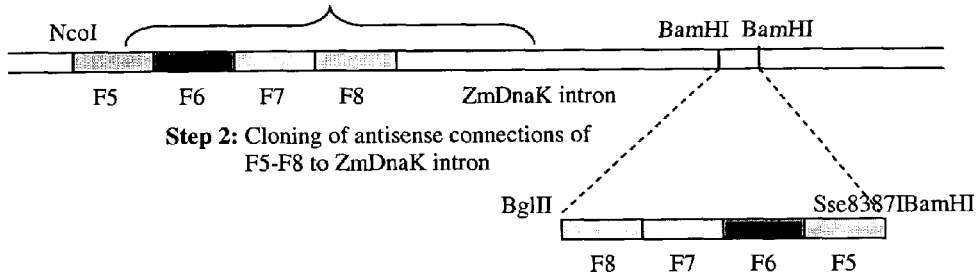

To build the intermediate dsRNA construct containing the F1 to F4 sequences, the sense connections of F1 to F4, antisense connections of F1 to F4, and ZmDnaK (gene encoding for HSP70) intron fragment (SEQ ID NO: 27) (see e.g., U.S. Pat. No. 5,424,412; Rochester et al., *EMBO J.*, 5:451-458 (1986)) were individually generated by PCR and assembled using a BamHI/BglII directional cloning method (FIG. 4). The PCR methods followed standard protocols set forth by the manufacturer (Roche Applied Science, Indianapolis, Ind.), and adding 5% DMSO, unless otherwise noted. The DMSO was added due to the high GC content of corn DNA.

The F1 fragment was PCR amplified from the DNA of the ZmKRP1 EST clone using primers P1-StuI (SEQ ID NO: 28) and P1-2R (SEQ ID NO: 29). The primers are set forth in Table 2 and shown in FIG. 5. The F1 fragment was then purified using standard methodology well-known in the art. The F1-2 fragment was generated using PCR amplification by using the purified F1 PCR product mixed with an equivalent amount of the DNA of the ZmKRP2 EST clone as template, and P1-StuI (SEQ ID NO: 28) and P2-3 (SEQ ID NO: 30) as primers. The PCR product F1-2 was gel-purified using standard methodology. Similarly, F3 and F4 were PCR connected using primers P4-Bgl (SEQ ID NO: 31), P3-4 (SEQ ID NO: 32), and P5-Bam (SEQ ID NO: 33) resulting in a PCR product F3-4. The F1-2 and F3-4 products were subsequently PCR connected using primers P1-StuI, P2-3, and P5-Bam (SEQ ID NO: 33). The resulting PCR product, F1-4, was purified and cloned into a vector using the Topo-TA cloning system (Invitrogen, Carlsbad, Calif.). The resulting clone, F14B3-sense, was full-length double-strand sequenced. The F1-4 fragment was then PCR amplified from the F14B3-sense clone using primers P5-Bgl (SEQ ID NO: 34) and P1-SseBam (SEQ ID NO: 35) to generate the antisense fragment. The resulting PCR product was again cloned using the Topo-TA cloning system to form the F14B3-antisense clone. This clone was confirmed by sequencing using standard methodology.

TABLE 2

Primers used in construction of ZmKRP dsRNA vector

| PCR/CONNECTIONS | PRIMERS | SEQ ID NO |
| --- | --- | --- |
| F1 and F2 | P1-StuI | 28 |
|  | P1-2R | 29 |
|  | P2-3 | 30 |
| F3 and F4 | P4-Bgl | 31 |
|  | P3-4 | 32 |
|  | P5-Bam | 33 |
| F1-2 and F3-4 | P1-StuI | 28 |
|  | P2-3 | 30 |
|  | P5-Bam | 33 |
| F1-4 antisense | P5-Bgl | 34 |
|  | P1-SseBam | 35 |
| ZmDnaK intron | Pi-Bgl | 36 |
|  | Pi-Bam | 37 |
| F5 and F6 | P5-Nco | 38 |
|  | P5-6 | 39 |
|  | P6-7 | 40 |
| F7 and F8 | P8-Bgl | 41 |
|  | P7-8 | 42 |
|  | P8-i | 43 |
| F5-6 and F7-8 | P5-Nco | 38 |
|  | P6-7 | 40 |
|  | P8-i | 43 |
| F5-8 and ZmDnaK intron | P5-Nco | 38 |
|  | P8-i | 43 |
|  | Pi-Bam | 37 |

The ZmDnaK-intron (see e.g., U.S. Pat. No. 5,424,412) was PCR amplified from the plant expression vector pMON70091 which contains a Z27 zein promoter (Lopes et al., *Mol. Gen. Genet.*, 247:603-613 (1995) and ZmDnaK intron using primers Pi-Bgl (SEQ ID NO: 36) and Pi-Bam (SEQ ID NO: 37). The PCR product, DnaK-1, was cloned using the Topo-TA cloning system. This clone was confirmed by full-length double-strand sequencing. The F1-4 sense, ZmDnaK intron, and F1-4 antisense fragments were assembled in a step-wise fashion. Firstly, the ZmDnaK intron was excised from the DnaK-1 construct described above using BglII and BamHI. This intron was then ligated to the BamHI site of F14B3-sense construct, such that the BglII site of ZmDnaK-intron/BamHI-BglII ligated to the BamHI site (introduced by primer P5-Bam) at the 3' end of F1-4. This ligation reaction yielded the construct F14In2. Secondly, the F1-4 fragment was excised from clone F14B3-antisense with BglII and BamHI, and the F1-4/BglII-BamHI fragment was ligated to the BamHI site of F14In2, such that the BglII site of F1-4/BglII-BamHI ligated to the BamHI site (introduced by primer Pi-Bam) at the 3' end of the ZmDnaK intron. This ligation reaction yielded the construct F142c1.

Finally, the whole DNA segment containing the F1-4 sense; ZmDnaK intron; F1-4 antisense fragment was excised from clone F142c1 using StuI and Sse8387I and cloned into pMON80611. pMON80611 is a binary vector for *Agrobacterium* transformation of plants. It contains left and right borders for T-DNA transfer, a plant selectable marker cassette consisting of enhanced 35s promoter::glyphosate resistance marker gene::nos 3' UTR (U.S. Pat. No. 5,627,061) and plant expression cassette sequences which include an oleosin L3 promoter (U.S. Pat. No. 6,433,252) and a maize globulin 3' UTR (see, for example, Belanger and Kriz, *Genet.*, 129:863-872, (1991)) with cloning sites available for expression of a gene of interest. The resulting expression cassette was named WWZHEN03.0024.

The intermediate dsRNA construct containing the F5 to F8 fragments was then generated. The sense connections of F5 to F8, antisense connections of F5 to F8, and ZmDnaK intron (SEQ ID NO: 27) were individually generated by PCR and assembled using either PCR or the BamHI/BglII directional cloning method as described above and shown in FIG. 5. Primers used in those PCR connections were listed in Table 2 and FIG. 5. The assembled segment comprising F5-8 sense; ZmDnaK intron; F5-8 antisense was then cloned to vector pMON80611 to generate the second expression cassette WWZHEN03.0023. To combine WWZHEN03.0023 and WWZHEN03.0024, the 4528 bp AscI-FseI segment from WWZHEN03.0023 that comprising F5-8 sense; ZmDnaK intron; F5-8 antisense was gel purified (Qiagen Inc., Valencia, Calif.) and ligated to WWZHEN03.0024 digested with MluI and FseI to generate the final corn transformation construct pMON71270 (FIG. 2).

Figure 3:
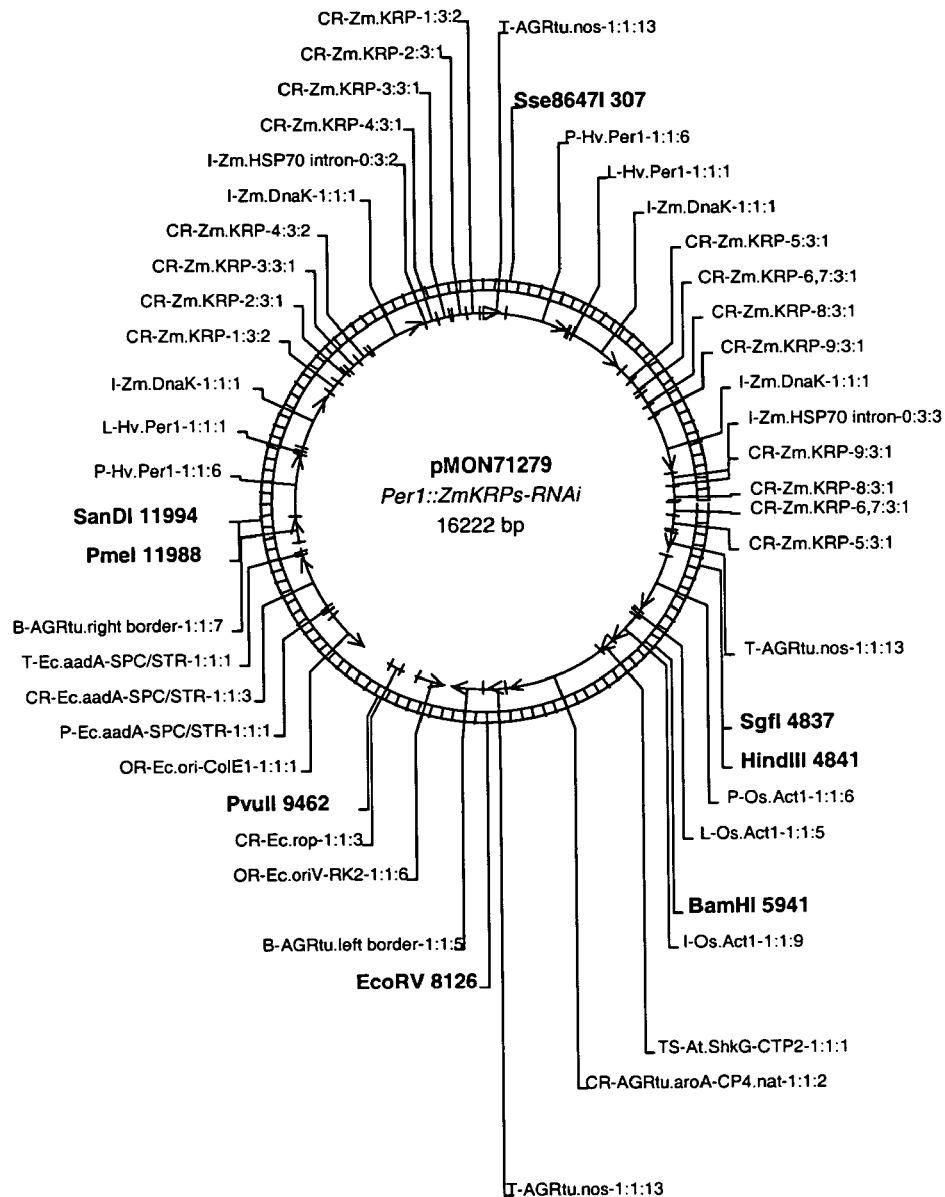
FIG. 3 is the construct map of pMON71279.

A Per1 promoter-driven ZmKRP suppression construct was made from the two intermediate dsRNA contructs WWZHEN03.0023 and WWZHDN03.0024 (above). First, the segment comprising F1-4 sense; ZmDnaK intron; F1-4 antisense was excised from WWZHDN03.0024 by SfiI and Sse8387I digestion, and then cloned to the SfiI and Sse8387I sites of vector pMON68290 which contained Per1 to generate WWZHEN03.0041. Similarly, the segment comprising F5-8 sense; ZmDnaK intron; F5-8 antisense was excised from WWZHEN03.0023 by SfiI and Sse8387I digestion, and then cloned to the SfiI and Sse8387I sites of vector pMON68290 which contained Per1 to generate WWZHEN03.0042. To combine WWZHEN03.0041 and WWZHEN03.0042, the 4481 bp AscI segment from WWZHEN03.0042, comprising F5-8 sense; ZmDnaK intron; F5-8 antisense, was gel purified (Qiagen Inc., Valencia, Calif.) and ligated to WWZHEN03.0041 digested with MluI to generate the final corn transformation construct pMON71279 (FIG. 3).

Example 4

This example sets forth the construction of plant transformation vectors for the suppression of one or more ZmKRP genes in corn.

Additional seed-specific suppression constructs are generated using alternative size fragments, ranging from 50 base pairs to the full-length gene, and either alone or in various combinations. By way of example, a dsRNA construct using a 200 base pair fragment of ZmKRP1 operably linked to the corn L3 (oleosin) promoter is generated. The F1 fragment and the ZmDnaK-intron are generated as described above in Example 3. The two fragments are ligated to generate an intermediate F1; ZmDnaK-intron fragment. An aliquot of isolated and purified F1 fragment is then PCR amplified to generate F1-antisense. The F1-antisense is then ligated to the intermediate F1; ZmDnaK-intron fragment to generate a dsRNA construct F1; ZmDnaK-intron; F1-antisense. The construct is then cloned into a vector downstream of the corn L3 (oleosin) promoter. Alternatively the construct is cloned into a vector downstream of a promoter such as P-Zm.CEP1, P-Zm.CPC214, P-Zm.CPC214tr1, P-Zm.CPC214tr2, P-Os-.CPC214, and P-Hv.PER1 as well as other embryo-preferred promoters known to those skilled in the art. Similar constructs are generated with ZmKRP2, ZmKRP3, ZmKRP4, ZmKRP5, ZmKRP6, ZmKRP7, ZmKRP8, and ZmKRP9. Transgenic corn plants are produced. Transgenic seed is analyzed from these constructs to identify alterations in germ mass, kernel mass, cellular proliferation, whole kernel oil levels, whole kernel protein levels (% dry weight), whole kernel amino acid composition, free amino acid levels, and micronutrient composition, as set forth in the examples that follow. The ZmKRP gene fragments used in dsRNA constructs, which result in alterations in any of the abovementioned properties, are then combined, depending on the desired phenotype of the transformed plant, in a single polycistronic dsRNA construct, which is then transformed into corn using *Agrobacterium* transformation; transgenic plants are generated as described in Example 10.

Example 5

This example describes how the expression of endogenous CDK inhibitor-like genes in a plant can be suppressed by using antisense technology.

The level of ZmKRP1 generated in a cell of a corn plant can be decreased by introducing into the genome a transgene-that expresses an antisense RNA of the ZmKRP1 polypeptide. For example, the ZmKRP1 cDNA, or a fragment thereof at least 100 bp in length, is cloned into the plant expression vector pMON80611 in the antisense orientation, which drives expression under control of the L3 promoter and contains the globulin 3' UTR (Belanger and Kriz, *Genet.*, 129:863-872 (1991)). The resulting vector is transformed into the genome of a corn plant as described in Example 10. Multiple copies of the antisense gene can be introduced into a genome. Other CDK inhibitor-like genes, for instance ZmKRP2, can be made into antisense constructs and expressed separately or in combinations, as described above for ZmKRP 1.

Example 6

This example describes how the expression of endogenous CDK inhibitor-like genes in a plant can be suppressed by using ribozyme technology.

The level of ZmKRP1 mRNA generated in a cell of a corn plant can be decreased by introducing into the genome a transgene that expresses a ribozyme targeted against an mRNA coding for a ZmKRP1 polypeptide. The ribozyme construct is generated by cloning at least 24 bp of ZmKRP1 cDNA with a ribozyme sequence added adjacent to the target AUG of the endogenous gene (Merlo et al., *Plant Cell*, 10(10): 1603-1622 (1998)) into pMON80611, which drives expression from the L3 promoter and contains the globulin 3' UTR (Belanger and Kriz, *Genet.*, 129:863-872 (1991)). The resulting construct is transformed into a corn plant as described in Example 10. Multiple copies of the ribozyme-containing ZmKRP genes can be introduced into a genome as described in Example 10. Ribozyme-containing genes targeted against a combination of other ZmKRP polypeptides (as described herein above) can be introduced into a genome as described above for ZmKRP1, such that multiple ZmKRP genes are simultaneously suppressed.

Example 7

This example describes how the expression of endogenous CDK inhibitor genes in a plant can be suppressed by using homologous recombination technology.

The level of ZmKRP1 generated in a cell of a corn plant can be decreased by a gene replacement method via homologous recombination. In this method, the endogenous ZmKRP1 gene is replaced by a mutagenized ZmKRP1 gene. The mutagenized gene codes for a ZmKRP1 that is less efficient, or completely deficient, in inhibition of CDK than the one encoded by the endogenous, replaced gene. The ZmKRP1-producing gene is mutagenized by one or more nucleotide deletions, insertions, duplications or replacements. The mutagenized gene is fused to a selectable marker gene and transformed into a cell of a corn plant as described in Example 10. Homologous recombination events that may result in gene replacement are selected on the basis of the selectable marker gene (Puchta et al., *Trends Plant Sci.*, 1:340 (1996); Kempin et al., *Nature*, 389:802 (1997)). Gene replacements are confirmed by Southern blot analysis or PCR and DNA sequencing.

In the same manner as described above, other CDK inhibitor genes can be suppressed, independently or in combinations.

Example 8

This example describes how the expression of endogenous CDK inhibitor genes in a plant can be suppressed by using sense suppression technology.

The level of ZmKRP1 polypeptide generated in a cell of a plant is decreased by sense suppression. For example, the cDNA coding for an ZmKRP1 polypeptide is fused to upstream (5') such as Per1, and/or downstream (3') transcriptional or translational regulatory sequences and the chimeric gene is cloned into an appropriate transformation vector that carries a selectable marker gene and the vector is transformed into a cell of a corn plant as described in Example 10. Transformants are selected on the basis of the presence of a marker gene (for instance glyphosate resistance). Transformants are confirmed by Southern blot analysis of the DNA from putative transformants. Most of the transgenic organisms that will be derived from such experimentations will express the transgene without affecting endogenous expression. However, in a few cases, both of the transgene and the endogenous gene will be suppressed. To identify these sense-suppressed plants, RNA or protein extracts from at least 60 transgenic plants will be analyzed for the presence of the ZmKRP mRNA or polypeptide, respectively. Other CDK inhibitor-like genes can be used, alone or in various combinations.

Example 9

This example sets forth one method of generating male sterile maize plants by expressing maize CDK inhibitors in male reproductive tissue.

The corn SILKY1 promoter is operably linked to ZmKRP1, ZmKRP2, ZmKRP4, ZmKRP5, and ZmKRP6 in separate expression constructs containing the nos 3' UTR (Bevan et al., *Nucl. Acid Res.*, 11:369 (1983)) (other possibilities exist) and a glyphosate resistance selectable marker. (See, U.S. Pat. No. 5,627,061). One or more of the resulting expression cassettes is/are transformed into corn using the *Agrobacterium* transformation protocol set forth in Example 10 and transgenic plants are generated.

Male sterility is determined by performing pollen germination assays (Walden, D. B. (1994), In vitro Pollen Germination (pp 723-724), The Maize Handbook, Freeling, M. and Walbot, V. eds, Springer-Verlag, New York, Inc.), if pollen is present. Additionally, pollen viability is assayed by the ability of the transgenic pollen to fertilize ovules of non-transgenic plants and to produce viable seed harboring the transgene. Sterile transgenic plants are maintained by fertilizing the transgenic plants with non-transgenic donor pollen.

Example 10

This example describes the transformation of maize plants with constructs containing maize CDK inhibitor-like sequences.

kanamycin in a 250-mL flask. The flask is placed on a shaker at approximately 150 rpm and 26° C. overnight. The *Agrobacterium* culture is then diluted (1 to 5) in the same liquid medium and put back on the shaker. Several hours later, one day before inoculation, the *Agrobacterium* cells are spun down at 3500 rpm for 15 min. The bacterium cell pellet is re-suspended in induction broth with 200 μM of acetosyringone and 50 mg/L spectinomycin and 25 mg/L kanamycin and the cell density was adjusted to 0.2 at $O.D._{660}$. The bacterium cell culture (50 mL in each 250-mL flask) is then put back on the shaker and grown overnight. On the morning of inoculation day, the bacterium cells are spun down and washed with liquid ½ MS VI medium (Table 3) supplemented with 200 μM of acetosyringone. After one more spinning, the bacterium cell pellet is re-suspended in ½ MS PL medium (Table 3) with 200 μM of acetosyringone (Table 3) and the cell density was adjusted to 1.0 at $O.D_{660}$ for inoculation.

Reagents are commercially available and can be purchased from a number of suppliers (see, for example, Sigma Chemical Co., St. Louis, Mo.).

TABLE 3

Media used [1].

| Component | ½ MS VI | ½ MS PL | Co-culture medium | Induction MS | MSW50 | MS/6BA | MSOD |
|---|---|---|---|---|---|---|---|
| MS salts | 68.5 g/l | 68.5 g/l | 2.2 g/l | 4.4 g/l | 4.4 g/l | 4.4 g/l | 4.4 g/l |
| Sucrose | 20 g/l | 68.6 g/l | 20 g/l | 30 g/l | 30 g/l | 30 g/l | — |
| Maltose | — | — | — | — | — | — | 20 g/l |
| Glucose | 10 g/l | 36 g/l | 10 g/l | — | — | — | 10 g/l |
| l-Proline | 115 mg/l | 115 mg/l | 115 mg/l | 1.36 g/l | 1.38 g/l | 1.36 g/l | — |
| Casamino Acids | — | — | — | 50 mg/l | 500 mg/l | 50 mg/l | — |
| Glycine | 2 mg/l | 2 mg/l | 2 mg/l | — | 2 mg/l | — | — |
| l-Asparagine | — | 100 mg/l | 100 mg/l | — | 100 mg/l | — | 150 mg/l |
| myo-Inositol | 100 mg/l | 0.5 mg/l | 0.5 mg/l | 1.3 mg/l | 0.5 mg/l | 1.3 mg/l | 100 mg/l |
| Nicotinic Acid | 0.5 mg/l | 0.5 mg/l | 0.5 mg/l | 0.25 mg/l | 0.5 mg/l | 0.25 mg/l | 1.3 mg/l |
| Pyridoxine.HCl | 0.5 mg/l | 0.1 mg/l | 0.6 mg/l | 0.25 mg/l | 0.6 mg/l | 0.25 mg/l | 0.25 mg/l |
| Thiamine.HCl | 0.5 mg/l | — | 3 mg/l | 0.5 mg/l | 0.5 mg/l | 0.25 mg/l | 0.25 mg/l |
| Ca Pantothenate | 0.1 mg/l | — | 1.7 mg/l | 2.2 mg/l 1.7 mg/l | — | 0.25 mg/l | 0.25 mg/l |
| 2,4-D | — | | | | | — | 0.25 mg/l |
| Picloram | — | | | | | — | mg/l |
| Silver Nitrate | — | | | | | | — |
| BAP | — | | | | | 3.5 mg/l | — |

[1]. Media ½ MSVI and ½ MSPL were used as liquid. Co-culture medium was solidified with 5.5 mg/l low EEO agarose. All other media were solidified with 7 g/l Phytagar for NPTII selection and with 3 g/l phytagel for glyphosate selection.

The transformation vectors described above are used to transform maize plants using the following procedure. Maize plants are grown in a greenhouse under standard practices. Controlled pollinations are made. *Agrobacterium* ABI containing a vector in glycerol stock is streaked out on solid LB medium supplemented with antibiotics kanamycin (50 mg/L), spectinomycin (50 mg/L), streptomycin (50 mg/L), and chloramphenicol (25 mg/L) and incubated at 28° C. for 2 days. Two days before *Agrobacterium* inoculation of the maize immature embryos, one colony or a small loop of *Agrobacterium* from the *Agrobacterium* plate is picked up and inoculated into 25 mL of liquid LB medium supplemented with 100 mg/L of spectinomycin and 50 mg/L of An elite corn line (LH244) is used for transformation in connection with this invention. Ears containing immature embryos are harvested approximately 10 days after pollination and kept refrigerated at 4° C. until use (up to 5 days post-harvest). The preferred embryo size for this method of transformation is ~1.0-2.0 mm. This size is usually achieved 10 days after pollination inside the green house with the growth conditions of an average temperature of 87° F., day length of 14 hours with supplemental lighting supplied by GE 1000 Watt High Pressure Sodium lamps.

Immature embryos are isolated from surface sterilized ears and directly dropped into the prepared *Agrobacterium* cell suspension in 1.5-mL microcentrifuge tube. The isolation lasts continuously for 15 min. The tube is then set aside for 5 min, which made the inoculation time for individual embryos from 5 to 20 min. After *Agrobacterium* cell suspension is removed using a fine tipped sterile transfer pipette, the immature embryos are transferred onto the co-culture medium (Table 3). The embryos are placed on the medium with the scutellum side facing up. The embryos are cultured in a dark incubator (23° C.) for approximately 24 h.

The embryos are then transferred onto a modified MS medium (MSW50, Table 3) supplemented with 0.1 or 0.25 mM glyphosate and 250 mg/L carbenicillin to inhibit *Agrobacterium* in Petri dishes (100 mm×25 mm). The cultures are incubated in a dark culture room at 27° C. for 2-3 weeks. All the callus pieces are then transferred individually onto the first regeneration medium (MS/6BA, Table 3) supplemented with the same levels of glyphosate. The cultures are grown on this medium and in a culture room with 16-h light/8-h dark photoperiod and 27° C. for 5-7 days. They are then transferred onto the second regeneration medium (MSOD, Table 3) in petri dish (100 mm×25 mm) for approximately 2 weeks. All the callus pieces with regenerating shoots and living tissue are transferred onto the same medium contained in phytatrays for shoots to grow further before being moved to soil. It takes 2-4 weeks. The regeneration media (MS6BA and MSOD) are all supplemented with 250 mg/L carbenicillin and 0.1 or 0.25 mM glyphosate.

These developing plantlets are then transferred to soil, hardened off in a growth chamber at 27° C., 80% humidity, and low light intensity for approximately 1 week, and then transferred to a greenhouse and grown under standard greenhouse conditions.

The greenhouse-grown plants are then analyzed for expression levels as well as oil and protein levels.

Example 11

This example describes expression analysis of transgenic plants.

RNA expression analysis is used to verify misexpression or suppression of CDK inhibitors in transgenic plants. As used in this application, "misexpression" means spatial or temporal expression other than endogenous expression, e.g. overexpression and ectopic expression. RNA is extracted by a standard protocol (Wadsworth et al., *Analytical Biochemistry*, 172(1):279-283 (1988)). To determine the misexpression or suppression of ZmKRP genes in corn embryo tissues, TaqMan analysis is performed using the TaqMan One-Step RT-PCR Master Mix Reagents Kit and Protocol (#4310299 rev. C) (Applied Biosystems, Foster City Calif.). cDNA is synthesized (SMART PCR cDNA Synthesis Kit, #K1052-1, Clonetech Laboratories, Inc.) and standard PCR using gene-specific primers and agarose-gel electrophoresis to visualize PCR products.

Example 12

This example provides the analytical procedures to determine oil and protein content, mass differences, amino acid composition, free amino acid levels, and micronutrient content of transgenic maize plants.

Oil levels (on a mass basis and as a percent of tissue weight) of first generation single corn kernels and dissected germ and endosperm are determined by low-resolution $^1$H nuclear magnetic resonance (NMR) (Tiwari et al., *JAOCS*, 51:104-109 (1974); or Rubel, *JAOCS*, 71:1057-1062 (1994)), whereby NMR relaxation times of single kernel samples are measured, and oil levels are calculated based on regression analysis using a standard curve generated from analysis of corn kernels with varying oil levels as determined gravimetrically following accelerated solvent extraction. One-way analysis of variance and the Student's T-test (JMP, version 4.04, SAS Institute Inc., Cary, N.C., USA) are performed to identify significant differences between transgenic and non-transgenic kernels as determined by transgene-specific PCR.

Oil levels and protein levels in second generation seed are determined by NIT spectroscopy, whereby NIT spectra of pooled seed samples harvested from individual plants are measured, and oil and protein levels are calculated based on regression analysis using a standard curve generated from analysis of corn kernels with varying oil or protein levels, as determined gravimetrically following accelerated solvent extraction or elemental (% N) analysis, respectively. One-way analysis of variance and the Student's T-test are performed to identify significant differences in oil (% kernel weight) and protein (% kernel weight) between seed from marker positive and marker negative plants.

The levels of free amino acids are analyzed from each of the transgenic events using the following procedure. Seeds from each of the transgenic plants are crushed individually into a fine powder and approximately 50 mg of the resulting powder is transferred to a pre-weighed centrifuge tube. The exact sample weight is recorded and 1.0 ml of 5% trichloroacetic acid is added to each sample tube. The samples are mixed at room temperature by vortex and then centrifuged for 15 minutes at 14,000 rpm on an Eppendorf microcentrifuge (Model 5415C, Brinkmann Instrument, Westbury, N.Y.). An aliquot of the supernatant is removed and analyzed by HPLC (Agilent 1100) using the procedure set forth in Agilent Technical Publication "Amino Acid Analysis Using the Zorbax Eclipse-AAA Columns and the Agilent 1100 HPLC," Mar. 17, 2000.

Quantitative determination of total amino acids from corn is performed by the following method. Kernels are ground and approximately 60 mg of the resulting meal is acid-hydrolyzed using 6 N HCl under reflux at 100° C. for 24 hrs. Samples are dried and reconstituted in 0.1 N HCl followed by precolumn derivatization with α-phthalaldehyde (OPA0 for HPLC analysis. The amino acids are separated by a reverse-phase Zorbax Eclipse XDB-C18 HPLC column on an Agilent 1100 HPLC (Agilent, Palo Alto, Calif.). The amino acids are detected by fluorescence. Cysteine, proline, asparagine, glutamine, and tryptophan are not included in this amino acid screen (Henderson et al., "Rapid, Accurate, Sensitive and Reproducible HPLC Analysis of Amino acids, Amino Acid Analysis Using Zorbax Eclipse-AAA Columns and the Agilent 1100 HPLC," Agilent Publication (2000); see, also, "Measurement of Acid-Stable Amino Acids," AACC Method 07-01 (American Association of Cereal Chemists, Approved Methods, 9th edition (LCCC#95-75308)). Total tryptophan is measured in corn kernels using an alkaline hydrolysis method as described (Approved Methods of the American Association of Cereal Chemists—$10^{th}$ edition, AACC ed, (2000) 07-20 Measurement of Tryptophan—Alakline Hydrolysis).

Tocopherol and tocotrienol levels in seeds are assayed by methods well-known in the art. Briefly, 10 mg of seed tissue are added to 1 g of microbeads (Biospec Product Inc, Barlesville, Okla.) in a sterile microfuge tube to which 500 μl 1% pyrogallol (Sigma Chemical Co., St. Louis, Mo.)/ethanol have been added. The mixture is shaken for 3 minutes in a mini Beadbeater (Biospec) on "fast" speed, then filtered through a 0.2 μm filter into an autosampler tube. The filtered extracts are analyzed by HPLC using a Zorbax silica HPLC column (4.6 mm×250 mm) with a fluorescent detection, an excitation at 290 nm, an emission at 336 nm, and bandpass and slits. Solvent composition and running conditions are as listed below with solvent A as hexane and solvent B as methyl-t-butyl ether. The injection volume is 20 μl, the flow rate is 1.5 ml/minute and the run time is 12 minutes at 40° C. The solvent gradient is 90% solvent A, 10% solvent B for 10 minutes; 25% solvent A, 75% solvent B for 11 minutes; and 90% solvent A, 10% solvent B for 12 minutes. Tocopherol standards in 1% pyrogallol/ethanol are run for comparison (α-tocopherol, γ-tocopherol, β-tocopherol, δ-tocopherol, and tocopherol (tocol)). Standard curves for alpha, beta, delta, and gamma tocopherol are calculated using Chemstation software (Hewlett Packard). Tocotrienol standards in 1% pyrogallol/ethanol are run for comparison (α-tocotrienol, γ-tocotrienol, β-tocotrienol, δ-tocotrienol). Standard curves for α-, β-, δ-, and γ-tocotrienol are calculated using Chemstation software (Hewlett Packard).

Carotenoid levels within transgenic corn kernels are determined by a standard protocol (Craft, *Meth. Enzymol.*, 213:185-205 (1992)). Plastiquinols and phylloquinones are determined by standard protocols (Threlfall et al., *Methods in Enzymology*, XVIII, part C, 369-396 (1971); and Ramadan et al., *Eur. Food Res. Technol.*, 214(6):521-527 (2002)).

Results from events containing pMON71270 are shown in Table 4.

TABLE 4 pMON71270 1st Generation Single Kernel Analysis

| Pedigree | Positive GOI | | | Negative GOI | | | | |
|---|---|---|---|---|---|---|---|---|
| | n | Mean | LSD | n | Mean | LSD | Prob > F | Signif | Delta |
| LH244/ZM_S86489 | | | | | | | | | |
| Kernel Oil (%) | 13 | 2.60 | 0.43 | 9 | 3.70 | 0.52 | 0.0001 | 0.001 | −1.10 |
| Germ Weight (g) | 13 | 0.0191 | 0.00326 | 9 | 0.0212 | 0.00 | 0.2529 | | −0.0020 |
| Germ Oil (%) | 13 | 20.81 | 3.69 | 9 | 27.58 | 4.44 | 0.0025 | 0.01 | −6.77 |
| Germ Weight (%) | 13 | 11.27 | 1.25 | 9 | 11.54 | 1.51 | 0.6894 | | −0.27 |
| Kernel Weight (g) | 13 | 0.1889 | 0.0174 | 9 | 0.2030 | 0.0209 | 0.1410 | | −0.0141 |
| Kernel Oil (mg) | 13 | 4.88 | 1.16 | 9 | 7.59 | 1.39 | 0.0003 | 0.001 | −2.71 |
| Germ Oil (mg) | 13 | 3.95 | 0.97 | 9 | 5.74 | 1.16 | 0.0023 | 0.01 | −1.79 |
| ZM_S86363/LH244 | | | | | | | | | |
| Kernel Oil (%) | 13 | 4.03 | 0.41 | 9 | 3.79 | 0.49 | 0.2772 | | 0.24 |
| Germ Weight (g) | 13 | 0.0164 | 0.0026 | 9 | 0.0134 | 0.0031 | 0.9927 | | 0.0030 |
| Germ Oil (%) | 13 | 31.17 | 1.91 | 9 | 30.65 | 2.30 | 0.6169 | | 0.52 |
| Germ Weight (%) | 13 | 12.51 | 1.25 | 9 | 12.09 | 1.51 | 0.5355 | | 0.42 |
| Kernel Weight (g) | 13 | 0.1516 | 0.0223 | 9 | 0.1542 | 0.0268 | 0.8255 | | −0.0026 |
| Kernel Oil (mg) | 13 | 6.10 | 1.16 | 9 | 5.86 | 1.39 | 0.6997 | | 0.24 |
| Germ Oil (mg) | 13 | 5.14 | 1.00 | 9 | 5.11 | 1.20 | 0.9554 | | 0.03 |
| ZM_S86474/LH244 | | | | | | | | | |
| Kernel Oil (%) | 11 | 2.92 | 0.62 | 13 | 2.87 | 0.57 | 0.8689 | | 0.05 |
| Germ Weight (g) | 11 | 0.0131 | 0.0060 | 13 | 0.0151 | 0.0055 | 0.4828 | | −0.0020 |
| Germ Oil (%) | 11 | 27.60 | 4.40 | 13 | 25.70 | 4.05 | 0.3613 | | 1.90 |
| Germ Weight (%) | 11 | 9.24 | 2.99 | 13 | 10.56 | 2.75 | 0.3515 | | −1.32 |
| Kernel Weight (g) | 11 | 0.1554 | 0.0283 | 13 | 0.1581 | 0.0261 | 0.8346 | | −0.0028 |
| Kernel Oil (mg) | 11 | 4.70 | 1.52 | 13 | 4.67 | 1.40 | 0.9671 | | 0.03 |
| Germ Oil (mg) | 11 | 3.61 | 1.35 | 13 | 3.65 | 1.25 | 0.9503 | | −0.04 |
| ZM_S86481/LH244 | | | | | | | | | |
| Kernel Oil (%) | 10 | 3.98 | 0.21 | 13 | 3.69 | 0.19 | 0.0067 | 0.01 | 0.29 |
| Germ Weight (g) | 10 | 0.0188 | 0.0036 | 13 | 0.0174 | 0.0032 | 0.3901 | | 0.0014 |
| Germ Oil (%) | 10 | 31.10 | 4.96 | 13 | 32.71 | 4.35 | 0.4794 | | −1.61 |
| Germ Weight (%) | 10 | 10.83 | 1.79 | 13 | 10.58 | 1.57 | 0.7637 | | 0.25 |
| Kernel Weight (g) | 10 | 0.1916 | 0.0157 | 13 | 0.1850 | 0.0137 | 0.3640 | | 0.0066 |
| Kernel Oil (mg) | 10 | 7.63 | 0.74 | 13 | 6.83 | 0.65 | 0.0254 | 0.05 | 0.80 |
| Germ Oil (mg) | 10 | 5.88 | 1.09 | 13 | 5.53 | 0.96 | 0.4867 | | 0.35 |
| ZM_S86483/LH244 | | | | | | | | | |
| Kernel Oil (%) | 1 | 3.52 | 1.28 | 23 | 4.06 | 0.27 | 0.2410 | | −0.54 |
| Germ Weight (g) | 1 | 0.0104 | 0.0088 | 23 | 0.0137 | 0.0018 | 0.2920 | | −0.0033 |
| Germ Oil (%) | 1 | 21.15 | 8.38 | 23 | 31.42 | 1.75 | 0.0019 | 0.01 | −10.27 |
| Germ Weight (%) | 1 | 11.11 | 3.55 | 23 | 11.94 | 0.74 | 0.5101 | | −0.83 |
| Kernel Weight (g) | 1 | 0.1025 | 0.0719 | 23 | 0.1286 | 0.0150 | 0.3087 | | −0.0261 |
| Kernel Oil (mg) | 1 | 3.61 | 3.02 | 23 | 5.21 | 0.63 | 0.1434 | | −1.60 |
| Germ Oil (mg) | 1 | 2.19 | 2.70 | 23 | 4.30 | 0.56 | 0.0352 | 0.05 | −2.11 |
| ZM_S86484/LH244 | | | | | | | | | |
| Kernel Oil (%) | 13 | 3.85 | 0.23 | 11 | 3.75 | 0.25 | 0.4003 | | 0.10 |
| Germ Weight (g) | 13 | 0.0186 | 0.0022 | 11 | 0.0187 | 0.0024 | 0.9640 | | 0.0000 |
| Germ Oil (%) | 13 | 29.33 | 1.56 | 11 | 29.46 | 1.70 | 0.8678 | | −0.13 |
| Germ Weight (%) | 13 | 11.76 | 0.73 | 11 | 11.64 | 0.80 | 0.7358 | | 0.13 |
| Kernel Weight (g) | 13 | 0.1769 | 0.0134 | 11 | 0.1786 | 0.0146 | 0.8060 | | −0.0017 |

TABLE 4-continued pMON71270 1st Generation Single Kernel Analysis

| Pedigree | Positive GOI | | | Negative GOI | | | Prob > F | Signif | Delta |
|---|---|---|---|---|---|---|---|---|---|
| | n | Mean | LSD | n | Mean | LSD | | | |
| Kernel Oil (mg) | 13 | 6.82 | 0.67 | 11 | 6.70 | 0.73 | 0.7371 | | 0.12 |
| Germ Oil (mg) | 13 | 5.47 | 0.67 | 11 | 5.48 | 0.72 | 0.9811 | | −0.01 |
| ZM__S86486/LH244 | | | | | | | | | |
| Kernel Oil (%) | 11 | 4.15 | 0.26 | 13 | 4.10 | 0.24 | 0.6438 | | 0.06 |
| Germ Weight (g) | 11 | 0.0159 | 0.0024 | 13 | 0.0152 | 0.0022 | 0.5029 | | 0.0007 |
| Germ Oil (%) | 11 | 32.65 | 2.06 | 13 | 32.05 | 1.89 | 0.5357 | | 0.60 |
| Germ Weight (%) | 11 | 10.64 | 1.25 | 13 | 10.37 | 1.15 | 0.6481 | | 0.27 |
| Kernel Weight (g) | 11 | 0.1657 | 0.0142 | 13 | 0.1630 | 0.0130 | 0.6841 | | 0.0027 |
| Kernel Oil (mg) | 11 | 6.87 | 0.50 | 13 | 6.64 | 0.46 | 0.3396 | | 0.23 |
| Germ Oil (mg) | 11 | 5.19 | 0.69 | 13 | 4.83 | 0.64 | 0.2764 | | 0.36 |
| ZM__S86487/LH244 | | | | | | | | | |
| Kernel Oil (%) | 10 | 3.93 | 0.25 | 14 | 3.76 | 0.21 | 0.1476 | | 0.17 |
| Germ Weight (g) | 10 | 0.0188 | 0.00266 | 14 | 0.0167 | 0.0023 | 0.0925 | 0.1 | 0.0021 |
| Germ Oil (%) | 10 | 32.54 | 2.42 | 14 | 32.35 | 2.04 | 0.8614 | | 0.19 |
| Germ Weight (%) | 10 | 10.80 | 1.39 | 14 | 9.72 | 1.18 | 0.0991 | 0.1 | 1.07 |
| Kernel Weight (g) | 10 | 0.1919 | 0.0127 | 14 | 0.1905 | 0.0108 | 0.8070 | | 0.0014 |
| Kernel Oil (mg) | 10 | 7.54 | 0.72 | 14 | 7.16 | 0.61 | 0.2471 | | 0.38 |
| Germ Oil (mg) | 10 | 6.10 | 0.90 | 14 | 5.38 | 0.76 | 0.0884 | 0.1 | 0.72 |
| ZM__S86493/LH244 | | | | | | | | | |
| Kernel Oil (%) | 9 | 3.66 | 0.69 | 15 | 3.94 | 0.53 | 0.3525 | | −0.28 |
| Germ Weight (g) | 9 | 0.0177 | 0.0041 | 15 | 0.0161 | 0.0031 | 0.3593 | | 0.0016 |
| Germ Oil (%) | 9 | 28.30 | 3.07 | 15 | 30.98 | 2.38 | 0.0548 | 0.1 | −2.68 |
| Germ Weight (%) | 9 | 10.61 | 1.99 | 15 | 10.52 | 1.54 | 0.9196 | | 0.09 |
| Kernel Weight (g) | 9 | 0.1813 | 0.0207 | 15 | 0.1699 | 0.0160 | 0.2153 | | 0.0114 |
| Kernel Oil (mg) | 9 | 6.80 | 1.59 | 15 | 6.73 | 1.24 | 0.9196 | | 0.07 |
| Germ Oil (mg) | 9 | 5.21 | 1.29 | 15 | 4.98 | 1.00 | 0.6775 | | 0.23 |
| ZM__S86521/LH244 | | | | | | | | | |
| Kernel Oil (%) | 18 | 3.58 | 0.20 | 5 | 3.83 | 0.38 | 0.0965 | 0.1 | −0.25 |
| Germ Weight (g) | 18 | 0.0134 | 0.0021 | 5 | 0.0155 | 0.0040 | 0.1935 | | −0.0021 |
| Germ Oil (%) | 18 | 30.82 | 1.91 | 5 | 28.40 | 3.63 | 0.0980 | 0.1 | 2.42 |
| Germ Weight (%) | 18 | 11.11 | 1.06 | 5 | 11.45 | 2.00 | 0.6653 | | −0.34 |
| Kernel Weight (g) | 18 | 0.1374 | 0.0163 | 5 | 0.1430 | 0.0309 | 0.6382 | | −0.0057 |
| Kernel Oil (mg) | 18 | 4.93 | 0.66 | 5 | 5.42 | 1.25 | 0.3195 | | −0.49 |
| Germ Oil (mg) | 18 | 4.09 | 0.57 | 5 | 4.40 | 1.08 | 0.4592 | | −0.31 |
| ZM__S86533/LH244 | | | | | | | | | |
| Kernel Oil (%) | 10 | 4.04 | 0.49 | 14 | 4.09 | 0.41 | 0.8145 | | −0.05 |
| Germ Weight (g) | 10 | 0.0196 | 0.0033 | 14 | 0.0183 | 0.0028 | 0.4218 | | 0.0012 |
| Germ Oil (%) | 10 | 29.10 | 2.03 | 14 | 29.79 | 1.71 | 0.4554 | | −0.69 |
| Germ Weight (%) | 10 | 12.56 | 1.44 | 14 | 12.10 | 1.22 | 0.4821 | | 0.46 |
| Kernel Weight (g) | 10 | 0.1732 | 0.0210 | 14 | 0.1684 | 0.0177 | 0.6203 | | 0.0047 |
| Kernel Oil (mg) | 10 | 6.99 | 1.25 | 14 | 6.92 | 1.06 | 0.9001 | | 0.07 |
| Germ Oil (mg) | 10 | 5.69 | 1.05 | 14 | 5.47 | 0.89 | 0.6410 | | 0.22 |
| ZM__S86541/LH244 | | | | | | | | | |
| Kernel Oil (%) | 7 | 3.73 | 0.26 | 17 | 3.80 | 0.17 | 0.5521 | | −0.06 |
| Germ Weight (g) | 7 | 0.0155 | 0.0044 | 17 | 0.0162 | 0.0028 | 0.6980 | | −0.0007 |
| Germ Oil (%) | 7 | 33.46 | 7.10 | 17 | 29.43 | 4.56 | 0.1752 | | 4.03 |
| Germ Weight (%) | 7 | 11.72 | 2.37 | 17 | 11.38 | 1.52 | 0.7209 | | 0.35 |
| Kernel Weight (g) | 7 | 0.1556 | 0.0279 | 17 | 0.1619 | 0.0179 | 0.5802 | | −0.0064 |
| Kernel Oil (mg) | 7 | 5.79 | 1.06 | 17 | 6.15 | 0.68 | 0.4167 | | −0.36 |
| Germ Oil (mg) | 7 | 4.86 | 1.19 | 17 | 4.78 | 0.76 | 0.8680 | | 0.08 |
| ZM__S86544/LH244 | | | | | | | | | |
| Kernel Oil (%) | 13 | 3.89 | 0.21 | 10 | 4.01 | 0.24 | 0.2788 | | −0.12 |
| Germ Weight (g) | 13 | 0.0179 | 0.0028 | 10 | 0.0178 | 0.0032 | 0.9600 | | 0.0001 |
| Germ Oil (%) | 13 | 30.41 | 2.18 | 10 | 31.53 | 2.49 | 0.3305 | | −1.12 |
| Germ Weight (%) | 13 | 11.52 | 1.00 | 10 | 10.90 | 1.14 | 0.2452 | | 0.62 |
| Kernel Weight (g) | 13 | 0.1735 | 0.0225 | 10 | 0.1804 | 0.0256 | 0.5562 | | −0.0069 |
| Kernel Oil (mg) | 13 | 6.75 | 1.01 | 10 | 7.25 | 1.15 | 0.3401 | | −0.51 |
| Germ Oil (mg) | 13 | 5.41 | 0.81 | 10 | 5.56 | 0.93 | 0.7318 | | −0.15 |
| ZM__S86548/LH244 | | | | | | | | | |
| Kernel Oil (%) | 11 | 4.94 | 1.18 | 13 | 4.09 | 1.09 | 0.1344 | | 0.85 |
| Germ Weight (g) | 11 | 0.0170 | 0.0027 | 13 | 0.0172 | 0.0024 | 0.8392 | | −0.0003 |
| Germ Oil (%) | 11 | 34.90 | 2.21 | 13 | 31.24 | 2.03 | 0.0017 | 0.01 | 3.66 |
| Germ Weight (%) | 11 | 12.54 | 2.70 | 13 | 10.70 | 2.48 | 0.1549 | | 1.84 |
| Kernel Weight (g) | 11 | 0.1619 | 0.0261 | 13 | 0.1824 | 0.0240 | 0.1043 | | −0.0204 |

TABLE 4-continued pMON71270 1st Generation Single Kernel Analysis

| | Positive GOI | | | Negative GOI | | | | |
|---|---|---|---|---|---|---|---|---|
| Pedigree | n | Mean | LSD | n | Mean | LSD | Prob > F | Signif | Delta |
| Kernel Oil (mg) | 11 | 7.38 | 0.81 | 13 | 7.46 | 0.74 | 0.8349 | | −0.08 |
| Germ Oil (mg) | 11 | 5.89 | 0.90 | 13 | 5.38 | 0.83 | 0.2321 | | 0.52 |
| ZM_S86551/LH244 | | | | | | | | | |
| Kernel Oil (%) | 9 | 3.76 | 0.25 | 15 | 3.88 | 0.19 | 0.2731 | | −0.12 |
| Germ Weight (g) | 9 | 0.0223 | 0.0031 | 15 | 0.0213 | 0.0024 | 0.4592 | | 0.0010 |
| Germ Oil (%) | 9 | 30.44 | 1.63 | 15 | 31.37 | 1.26 | 0.1969 | | −0.94 |
| Germ Weight (%) | 9 | 11.32 | 1.18 | 15 | 10.80 | 0.91 | 0.3228 | | 0.51 |
| Kernel Weight (g) | 9 | 0.2200 | 0.0180 | 15 | 0.2200 | 0.0139 | 0.9957 | | 0.0000 |
| Kernel Oil (mg) | 9 | 8.26 | 0.86 | 15 | 8.53 | 0.67 | 0.4798 | | −0.27 |
| Germ Oil (mg) | 9 | 6.78 | 1.04 | 15 | 6.71 | 0.80 | 0.8741 | | 0.07 |
| ZM_S86571/LH244 | | | | | | | | | |
| Kernel Oil (%) | 17 | 3.81 | 0.20 | 7 | 3.83 | 0.31 | 0.8670 | | −0.02 |
| Germ Weight (g) | 17 | 0.0211 | 0.0025 | 7 | 0.0216 | 0.0039 | 0.7492 | | −0.0005 |
| Germ Oil (%) | 17 | 29.76 | 2.16 | 7 | 30.25 | 3.36 | 0.7197 | | −0.49 |
| Germ Weight (%) | 17 | 11.00 | 1.00 | 7 | 11.45 | 1.56 | 0.4874 | | −0.45 |
| Kernel Weight (g) | 17 | 0.2141 | 0.0125 | 7 | 0.2114 | 0.0195 | 0.7365 | | 0.0027 |
| Kernel Oil (mg) | 17 | 8.14 | 0.53 | 7 | 8.09 | 0.82 | 0.8807 | | 0.05 |
| Germ Oil (mg) | 17 | 6.25 | 0.80 | 7 | 6.56 | 1.24 | 0.5378 | | −0.31 |
| ZM_S86572/LH244 | | | | | | | | | |
| Kernel Oil (%) | 14 | 3.91 | 0.25 | 10 | 3.78 | 0.29 | 0.3110 | | 0.14 |
| Germ Weight (g) | 14 | 0.0220 | 0.0020 | 10 | 0.0212 | 0.0024 | 0.4270 | | 0.0009 |
| Germ Oil (%) | 14 | 29.65 | 1.95 | 10 | 28.52 | 2.31 | 0.2892 | | 1.12 |
| Germ Weight (%) | 14 | 12.21 | 0.97 | 10 | 11.33 | 1.15 | 0.1032 | | 0.87 |
| Kernel Weight (g) | 14 | 0.2021 | 0.0095 | 10 | 0.2091 | 0.0112 | 0.1793 | | −0.0069 |
| Kernel Oil (mg) | 14 | 7.90 | 0.57 | 10 | 7.89 | 0.68 | 0.9605 | | 0.02 |
| Germ Oil (mg) | 14 | 6.53 | 0.79 | 10 | 6.05 | 0.94 | 0.2713 | | 0.47 |
| ZM_S86578/LH244 | | | | | | | | | |
| Kernel Oil (%) | 16 | 3.76 | 0.27 | 8 | 3.55 | 0.37 | 0.1921 | | 0.21 |
| Germ Weight (g) | 16 | 0.0195 | 0.0013 | 8 | 0.0193 | 0.0019 | 0.7350 | | 0.0003 |
| Germ Oil (%) | 16 | 29.78 | 1.51 | 8 | 27.82 | 2.14 | 0.0395 | 0.05 | 1.96 |
| Germ Weight (%) | 16 | 11.66 | 0.81 | 8 | 10.89 | 1.15 | 0.1246 | | 0.76 |
| Kernel Weight (g) | 16 | 0.1888 | 0.0104 | 8 | 0.1999 | 0.0146 | 0.0851 | 0.1 | −0.0110 |
| Kernel Oil (mg) | 16 | 7.07 | 0.46 | 8 | 7.08 | 0.66 | 0.9640 | | −0.01 |
| Germ Oil (mg) | 16 | 5.80 | 0.36 | 8 | 5.34 | 0.51 | 0.0423 | 0.05 | 0.46 |
| ZM_S87124/LH244 | | | | | | | | | |
| Kernel Oil (%) | 13 | 2.55 | 0.29 | 11 | 3.57 | 0.31 | <.0001 | 0.001 | −1.03 |
| Germ Weight (g) | 13 | 0.0140 | 0.0011 | 11 | 0.0139 | 0.0012 | 0.8423 | | |
| Germ Oil (%) | 13 | 22.77 | 3.42 | 11 | 30.49 | 3.72 | 0.0002 | 0.001 | −7.71 |
| Germ Weight (%) | 13 | 10.64 | 0.88 | 11 | 10.73 | 0.96 | 0.8354 | | −0.09 |
| Kernel Weight (g) | 13 | 0.1478 | 0.0100 | 11 | 0.1441 | 0.0108 | 0.4684 | | 0.0037 |
| Kernel Oil (mg) | 13 | 3.76 | 0.48 | 11 | 5.15 | 0.52 | <.0001 | 0.001 | −1.39 |
| Germ Oil (mg) | 13 | 3.16 | 0.45 | 11 | 4.22 | 0.49 | 0.0001 | 0.001 | −1.07 |

Examples of increased oil and organ size are demonstrated in several events. The milligrams oil per germ was increased in two independent events, ZM_S86578 (p=0.05) and ZM_S86487 (p=0.1). The milligrams of oil per kernel (p=0.05) and kernel oil as a percentage of dry wt (p=0.01) were both increased in event ZM_S86481. Germ oil as a percentage of dry wt was increased in three independent events, ZM_S86521 (p=0.1), ZM_S86548 (p=0.01) and ZM_S86578 (p=0.05). Germ wt (gram dry wt) (p=0.1) and germ wt as a percentage of total kernel wt (p=0.1) were increased in event ZM_S86487.

Results from events containing pMON71279 are shown in Table 5.

TABLE 5 pMON71279 1st Generation Single Kernel Analysis

| | Positive GOI | | | Negative GOI | | | | |
|---|---|---|---|---|---|---|---|---|
| Variable | n | Mean | LSD | n | Mean | LSD | Prob > F | Signif | Delta |
| LH244/ZM_S106956 | | | | | | | | | |
| Kernel Oil (%) | 20 | 3.90 | 0.13 | 4 | 3.75 | 0.28 | 0.1840 | | 0.15 |
| Germ Weight (g) | 20 | 0.0222 | 0.0019 | 4 | 0.0235 | 0.0043 | 0.4242 | | −0.0013 |

TABLE 5-continued pMON71279 1st Generation Single Kernel Analysis

| Variable | Positive GOI | | | Negative GOI | | | Prob > F | Signif | Delta |
|---|---|---|---|---|---|---|---|---|---|
| | n | Mean | LSD | n | Mean | LSD | | | |
| Germ Oil (%) | 20 | 27.80 | 1.13 | 4 | 27.90 | 2.52 | 0.9210 | | −0.09 |
| Germ Weight (%) | 20 | 11.76 | 0.51 | 4 | 11.25 | 1.14 | 0.2463 | | 0.51 |
| Kernel Weight (g) | 20 | 0.1885 | 0.0142 | 4 | 0.2078 | 0.0318 | 0.1197 | | −0.0193 |
| Germ Oil (mg) | 20 | 6.14 | 0.48 | 4 | 6.49 | 1.08 | 0.3952 | | −0.35 |
| Kernel Oil (mg) | 20 | 7.32 | 0.51 | 4 | 7.78 | 1.14 | 0.2972 | | −0.45 |
| LH244/ZM_S106984 | | | | | | | | | |
| Kernel Oil (%) | 14 | 3.91 | 0.17 | 8 | 3.99 | 0.22 | 0.4023 | | −0.08 |
| Germ Weight (g) | 14 | 0.0230 | 0.0021 | 8 | 0.0226 | 0.0028 | 0.7897 | | 0.0003 |
| Germ Oil (%) | 14 | 28.84 | 1.57 | 8 | 29.29 | 2.08 | 0.6159 | | −0.45 |
| Germ Weight (%) | 14 | 11.66 | 0.90 | 8 | 11.31 | 1.19 | 0.4917 | | 0.36 |
| Kernel Weight (g) | 14 | 0.1969 | 0.0114 | 8 | 0.2006 | 0.0151 | 0.5755 | | −0.0037 |
| Germ Oil (mg) | 14 | 6.61 | 0.59 | 8 | 6.61 | 0.79 | 0.9996 | | 0.00 |
| Kernel Oil (mg) | 14 | 7.72 | 0.53 | 8 | 7.99 | 0.71 | 0.3879 | | −0.26 |
| LH244/ZM_S106985 | | | | | | | | | |
| Kernel Oil (%) | 12 | 3.56 | 0.18 | 11 | 3.38 | 0.19 | 0.0619 | | 0.18 |
| Germ Weight (g) | 12 | 0.0211 | 0.0025 | 11 | 0.0214 | 0.0026 | 0.7901 | | −0.0003 |
| Germ Oil (%) | 12 | 25.42 | 1.90 | 11 | 25.14 | 1.98 | 0.7679 | | 0.28 |
| Germ Weight (%) | 12 | 10.80 | 1.06 | 11 | 11.11 | 1.11 | 0.5677 | | −0.30 |
| Kernel Weight (g) | 12 | 0.1959 | 0.0107 | 11 | 0.1924 | 0.0111 | 0.5158 | | 0.0035 |
| Germ Oil (mg) | 12 | 5.36 | 0.58 | 11 | 5.35 | 0.60 | 0.9574 | | 0.02 |
| Kernel Oil (mg) | 12 | 6.98 | 0.53 | 11 | 6.48 | 0.55 | 0.0682 | 0.1 | 0.50 |
| LH244/ZM_S108558 | | | | | | | | | |
| Kernel Oil (%) | 14 | 3.60 | 0.17 | 10 | 3.73 | 0.20 | 0.1630 | | −0.13 |
| Germ Weight (g) | 14 | 0.0229 | 0.0012 | 10 | 0.0229 | 0.0015 | 0.9983 | | 0.0000 |
| Germ Oil (%) | 14 | 26.20 | 1.48 | 10 | 26.71 | 1.75 | 0.5464 | | −0.52 |
| Germ Weight (%) | 14 | 11.90 | 0.66 | 10 | 11.85 | 0.78 | 0.8835 | | 0.05 |
| Kernel Weight (g) | 14 | 0.1930 | 0.0137 | 10 | 0.1946 | 0.0163 | 0.8276 | | −0.0016 |
| Germ Oil (mg) | 14 | 6.02 | 0.47 | 10 | 6.11 | 0.56 | 0.7028 | | −0.10 |
| Kernel Oil (mg) | 14 | 6.92 | 0.48 | 10 | 7.28 | 0.56 | 0.1623 | | −0.36 |
| ZM_S105162/LH244 | | | | | | | | | |
| Kernel Oil (%) | 13 | 3.68 | 0.38 | 11 | 3.74 | 0.42 | 0.7919 | | −0.05 |
| Germ Weight (g) | 13 | 0.0193 | 0.0032 | 11 | 0.0179 | 0.0035 | 0.4090 | | 0.0014 |
| Germ Oil (%) | 13 | 28.77 | 2.42 | 11 | 28.64 | 2.63 | 0.9174 | | 0.13 |
| Germ Weight (%) | 13 | 11.30 | 1.16 | 11 | 10.50 | 1.26 | 0.1872 | | 0.80 |
| Kernel Weight (g) | 13 | 0.1706 | 0.0226 | 11 | 0.1709 | 0.0246 | 0.9820 | | −0.0003 |
| Germ Oil (mg) | 13 | 5.50 | 0.83 | 11 | 5.12 | 0.90 | 0.3753 | | 0.38 |
| Kernel Oil (mg) | 13 | 6.22 | 0.84 | 11 | 6.33 | 0.92 | 0.796 | | −0.11 |
| ZM_S105166/LH244 | | | | | | | | | |
| Kernel Oil (%) | 9 | 3.37 | 0.19 | 15 | 3.40 | 0.15 | 0.6861 | | −0.03 |
| Germ Weight (g) | 9 | 0.0216 | 0.0033 | 15 | 0.0182 | 0.0026 | 0.0288 | 0.05 | 0.0034 |
| Germ Oil (%) | 9 | 26.59 | 2.49 | 15 | 28.04 | 1.93 | 0.1921 | | −1.45 |
| Germ Weight (%) | 9 | 11.17 | 1.03 | 15 | 10.48 | 0.80 | 0.1391 | | 0.68 |
| Kernel Weight (g) | 9 | 0.1933 | 0.0205 | 15 | 0.1721 | 0.0159 | 0.0255 | 0.05 | 0.0212 |
| Germ Oil (mg) | 9 | 5.71 | 0.92 | 15 | 5.09 | 0.71 | 0.1359 | | 0.61 |
| Kernel Oil (mg) | 9 | 6.49 | 0.79 | 15 | 5.88 | 0.61 | 0.0924 | 0.1 | 0.60 |
| ZM_S105183/LH244 | | | | | | | | | |
| Kernel Oil (%) | 18 | 3.30 | 0.19 | 6 | 3.28 | 0.33 | 0.8978 | | 0.02 |
| Germ Weight (g) | 18 | 0.0214 | 0.0011 | 6 | 0.0192 | 0.0018 | 0.0059 | 0.01 | 0.0022 |
| Germ Oil (%) | 18 | 25.30 | 1.53 | 6 | 23.99 | 2.64 | 0.2221 | | 1.31 |
| Germ Weight (%) | 18 | 11.65 | 0.58 | 6 | 10.95 | 1.00 | 0.0886 | 0.1 | 0.70 |
| Kernel Weight (g) | 18 | 0.1842 | 0.0086 | 6 | 0.1767 | 0.0149 | 0.2123 | | 0.0075 |
| Germ Oil (mg) | 18 | 5.41 | 0.33 | 6 | 4.61 | 0.57 | 0.0017 | 0.01 | 0.80 |
| Kernel Oil (mg) | 18 | 6.06 | 0.39 | 6 | 5.77 | 0.67 | 0.2789 | | 0.29 |
| ZM_S105185/LH244 | | | | | | | | | |
| Kernel Oil (%) | 19 | 3.36 | 0.15 | 5 | 3.22 | 0.29 | 0.2233 | | 0.14 |
| Germ Weight (g) | 19 | 0.0201 | 0.0018 | 5 | 0.0188 | 0.0034 | 0.3493 | | 0.0013 |
| Germ Oil (%) | 19 | 25.77 | 1.81 | 5 | 24.79 | 3.52 | 0.4769 | | 0.98 |
| Germ Weight (%) | 19 | 11.55 | 0.80 | 5 | 10.97 | 1.56 | 0.3447 | | 0.58 |
| Kernel Weight (g) | 19 | 0.1743 | 0.0097 | 5 | 0.1714 | 0.0188 | 0.6905 | | 0.0029 |
| Germ Oil (mg) | 19 | 5.12 | 0.28 | 5 | 4.67 | 0.55 | 0.0468 | 0.05 | 0.45 |
| Kernel Oil (mg) | 19 | 5.84 | 0.31 | 5 | 5.54 | 0.60 | 0.2058 | | 0.30 |
| ZM_S105187/LH244 | | | | | | | | | |
| Kernel Oil (%) | 12 | 3.38 | 0.16 | 12 | 3.46 | 0.16 | 0.3052 | | −0.08 |
| Germ Weight (g) | 12 | 0.0196 | 0.0032 | 12 | 0.0192 | 0.0032 | 0.8001 | | 0.0004 |
| Germ Oil (%) | 12 | 26.05 | 2.06 | 12 | 26.58 | 2.06 | 0.6010 | | −0.53 |

TABLE 5-continued pMON71279 1st Generation Single Kernel Analysis

| | Positive GOI | | | Negative GOI | | | | |
|---|---|---|---|---|---|---|---|---|
| Variable | n | Mean | LSD | n | Mean | LSD | Prob > F | Signif | Delta |
| Germ Weight (%) | 12 | 11.47 | 1.32 | 12 | 10.91 | 1.32 | 0.3872 | | 0.56 |
| Kernel Weight (g) | 12 | 0.1695 | 0.0134 | 12 | 0.1748 | 0.0134 | 0.4212 | | −0.0053 |
| Germ Oil (mg) | 12 | 5.03 | 0.66 | 12 | 5.06 | 0.66 | 0.9253 | | −0.03 |
| Kernel Oil (mg) | 12 | 5.73 | 0.56 | 12 | 6.03 | 0.56 | 0.2684 | | −0.31 |
| ZM__S105198/LH244 | | | | | | | | | |
| Kernel Oil (%) | 3 | 3.27 | 0.37 | 21 | 3.34 | 0.14 | 0.6027 | | −0.07 |
| Germ Weight (g) | 3 | 0.0200 | 0.0027 | 21 | 0.0199 | 0.0010 | 0.9150 | | 0.0001 |
| Germ Oil (%) | 3 | 24.09 | 3.68 | 21 | 25.97 | 1.39 | 0.1744 | | −1.88 |
| Germ Weight (%) | 3 | 11.25 | 1.07 | 21 | 10.79 | 0.40 | 0.2510 | | 0.46 |
| Kernel Weight (g) | 3 | 0.1783 | 0.0210 | 21 | 0.1845 | 0.0079 | 0.4210 | | −0.0063 |
| Germ Oil (mg) | 3 | 4.81 | 1.00 | 21 | 5.17 | 0.37 | 0.3244 | | −0.36 |
| Kernel Oil (mg) | 3 | 5.79 | 1.14 | 21 | 6.18 | 0.43 | 0.3587 | | −0.39 |
| ZM__S106940/LH244 | | | | | | | | | |
| Kernel Oil (%) | 18 | 3.77 | 0.17 | 5 | 3.62 | 0.32 | 0.2436 | | 0.15 |
| Germ Weight (g) | 18 | 0.0174 | 0.0025 | 5 | 0.0150 | 0.0047 | 0.1983 | | 0.0024 |
| Germ Oil (%) | 18 | 29.59 | 1.32 | 5 | 29.78 | 2.50 | 0.8476 | | −0.19 |
| Germ Weight (%) | 18 | 11.07 | 0.87 | 5 | 9.88 | 1.65 | 0.0752 | 0.1 | 1.19 |
| Kernel Weight (g) | 18 | 0.1563 | 0.0200 | 5 | 0.1544 | 0.0380 | 0.8979 | | 0.0019 |
| Germ Oil (mg) | 18 | 5.13 | 0.73 | 5 | 4.46 | 1.38 | 0.2195 | | 0.67 |
| Kernel Oil (mg) | 18 | 5.88 | 0.74 | 5 | 5.58 | 1.41 | 0.5874 | | 0.30 |
| ZM__S106960/LH244 | | | | | | | | | |
| Kernel Oil (%) | 12 | 3.88 | 0.20 | 12 | 3.78 | 0.20 | 0.3505 | | 0.09 |
| Germ Weight (g) | 12 | 0.0218 | 0.0019 | 12 | 0.0215 | 0.0019 | 0.7616 | | 0.0003 |
| Germ Oil (%) | 12 | 29.11 | 2.20 | 12 | 28.64 | 2.20 | 0.6596 | | 0.47 |
| Germ Weight (%) | 12 | 11.32 | 0.82 | 12 | 10.86 | 0.82 | 0.2613 | | 0.46 |
| Kernel Weight (g) | 12 | 0.1925 | 0.0091 | 12 | 0.1982 | 0.0091 | 0.2080 | | −0.0057 |
| Germ Oil (mg) | 12 | 6.32 | 0.58 | 12 | 6.15 | 0.58 | 0.5547 | | 0.17 |
| Kernel Oil (mg) | 12 | 7.48 | 0.45 | 12 | 7.49 | 0.45 | 0.9759 | | −0.01 |
| ZM__S106965/LH244 | | | | | | | | | |
| Kernel Oil (%) | 14 | 3.86 | 0.17 | 10 | 3.72 | 0.21 | 0.1510 | | 0.14 |
| Germ Weight (g) | 14 | 0.0217 | 0.0020 | 10 | 0.0219 | 0.0024 | 0.8803 | | −0.0002 |
| Germ Oil (%) | 14 | 29.87 | 1.65 | 10 | 29.17 | 1.95 | 0.4270 | | 0.71 |
| Germ Weight (%) | 14 | 11.39 | 0.69 | 10 | 11.22 | 0.81 | 0.6391 | | 0.17 |
| Kernel Weight (g) | 14 | 0.1912 | 0.0157 | 10 | 0.1948 | 0.0186 | 0.6752 | | −0.0035 |
| Germ Oil (mg) | 14 | 6.49 | 0.63 | 10 | 6.36 | 0.74 | 0.7067 | | 0.13 |
| Kernel Oil (mg) | 14 | 7.39 | 0.75 | 10 | 7.24 | 0.88 | 0.7115 | | 0.15 |
| ZM__S106971/LH244 | | | | | | | | | |
| Kernel Oil (%) | 12 | 3.73 | 0.25 | 11 | 3.88 | 0.26 | 0.2432 | | −0.15 |
| Germ Weight (g) | 12 | 0.0219 | 0.0017 | 11 | 0.0229 | 0.0018 | 0.2563 | | −0.0010 |
| Germ Oil (%) | 12 | 29.02 | 1.49 | 11 | 28.30 | 1.56 | 0.3377 | | 0.72 |
| Germ Weight (%) | 12 | 11.00 | 0.78 | 11 | 11.37 | 0.81 | 0.3351 | | −0.38 |
| Kernel Weight (g) | 12 | 0.1998 | 0.0133 | 11 | 0.2020 | 0.0139 | 0.7431 | | −0.0022 |
| Germ Oil (mg) | 12 | 6.36 | 0.57 | 11 | 6.48 | 0.59 | 0.6736 | | −0.12 |
| Kernel Oil (mg) | 12 | 7.48 | 0.80 | 11 | 7.88 | 0.83 | 0.3201 | | −0.40 |
| ZM__S106973/LH244 | | | | | | | | | |
| Kernel Oil (%) | 8 | 4.11 | 0.46 | 16 | 4.16 | 0.33 | 0.8231 | | −0.04 |
| Germ Weight (g) | 8 | 0.0169 | 0.0055 | 16 | 0.0170 | 0.0039 | 0.972 | | −0.0001 |
| Germ Oil (%) | 8 | 28.48 | 3.52 | 16 | 30.06 | 2.49 | 0.2951 | | −1.57 |
| Germ Weight (%) | 8 | 11.42 | 1.59 | 16 | 10.92 | 1.12 | 0.4593 | | 0.50 |
| Kernel Weight (g) | 8 | 0.1448 | 0.0397 | 16 | 0.1532 | 0.0281 | 0.6167 | | −0.0084 |
| Germ Oil (mg) | 8 | 4.88 | 1.82 | 16 | 5.13 | 1.29 | 0.746 | | −0.25 |
| Kernel Oil (mg) | 8 | 6.03 | 1.94 | 16 | 6.40 | 1.37 | 0.6506 | | −0.37 |
| ZM__S106979/LH244 | | | | | | | | | |
| Kernel Oil (%) | 7 | 3.99 | 0.23 | 17 | 3.98 | 0.15 | 0.9716 | | 0.00 |
| Germ Weight (g) | 7 | 0.0244 | 0.0044 | 17 | 0.0190 | 0.0028 | 0.006 | 0.01 | 0.0054 |
| Germ Oil (%) | 7 | 30.95 | 1.90 | 17 | 31.51 | 1.22 | 0.4717 | | −0.56 |
| Germ Weight (%) | 7 | 11.49 | 1.09 | 17 | 11.19 | 0.70 | 0.511 | | 0.30 |
| Kernel Weight (g) | 7 | 0.2139 | 0.0382 | 17 | 0.1702 | 0.0245 | 0.0098 | 0.01 | 0.0437 |
| Germ Oil (mg) | 7 | 7.52 | 1.32 | 17 | 5.98 | 0.85 | 0.0088 | 0.01 | 1.54 |
| Kernel Oil (mg) | 7 | 8.53 | 1.60 | 17 | 6.78 | 1.02 | 0.013 | 0.05 | 1.75 |
| ZM__S106982/LH244 | | | | | | | | | |
| Kernel Oil (%) | 13 | 3.86 | 0.21 | 11 | 3.96 | 0.23 | 0.3465 | | −0.10 |
| Germ Weight (g) | 13 | 0.0217 | 0.0025 | 11 | 0.0210 | 0.0027 | 0.5821 | | 0.0007 |
| Germ Oil (%) | 13 | 28.08 | 1.66 | 11 | 29.70 | 1.80 | 0.0644 | 0.1 | −1.62 |
| Germ Weight (%) | 13 | 11.75 | 0.93 | 11 | 11.41 | 1.01 | 0.4732 | | 0.34 |

TABLE 5-continued pMON71279 1st Generation Single Kernel Analysis

| Variable | Positive GOI | | | Negative GOI | | | Prob > F | Signif | Delta |
|---|---|---|---|---|---|---|---|---|---|
| | n | Mean | LSD | n | Mean | LSD | | | |
| Kernel Weight (g) | 13 | 0.1841 | 0.0170 | 11 | 0.1849 | 0.0185 | 0.9244 | | −0.0008 |
| Germ Oil (mg) | 13 | 6.09 | 0.76 | 11 | 6.22 | 0.83 | 0.7215 | | −0.14 |
| Kernel Oil (mg) | 13 | 7.08 | 0.61 | 11 | 7.31 | 0.67 | 0.4652 | | −0.23 |
| ZM_S106983/LH244 | | | | | | | | | |
| Kernel Oil (%) | 14 | 3.97 | 0.15 | 8 | 4.03 | 0.20 | 0.5323 | | −0.05 |
| Germ Weight (g) | 14 | 0.0225 | 0.0020 | 8 | 0.0212 | 0.0026 | 0.2314 | | 0.0014 |
| Germ Oil (%) | 14 | 30.32 | 1.12 | 8 | 30.54 | 1.49 | 0.7329 | | −0.22 |
| Germ Weight (%) | 14 | 11.77 | 0.61 | 8 | 11.93 | 0.80 | 0.6405 | | −0.16 |
| Kernel Weight (g) | 14 | 0.1911 | 0.0140 | 8 | 0.1780 | 0.0185 | 0.1093 | 0.1 | 0.0132 |
| Germ Oil (mg) | 14 | 6.83 | 0.64 | 8 | 6.47 | 0.85 | 0.3314 | | 0.36 |
| Kernel Oil (mg) | 14 | 7.61 | 0.61 | 8 | 7.16 | 0.81 | 0.2031 | | 0.45 |

Examples of increased oil and organ size are demonstrated in several events. Germ wt (g dry wt) was increased in three independent events, ZM_S105183 (p=0.01), ZM_S105166 (p=0.05) and ZM_S106973 (p=0.01). The milligrams of oil per germ was increased in three independent events, ZM_S105183 (p=0.01), ZM_S105185 (p=0.05), and ZM_S106979 (p=0.01). Germ wt as a percentage of total kernel wt was increased in two independent events, ZM_S105183 (p=0.1) and ZM_S106940 (p=0.1). The milligrams of oil per kernel was increased in two independent events, ZM_S105166 (p=0.1) and ZM_S106979 (p=0.05). Kernel oil as a percentage of dry wt was increased in event ZM_S106985 (p=0.1). Kernel wt (g dry wt) was increased in two independent events ZM_S105166 (p=0.05) and ZM_S106979 (p=0.01).

Results show that seed harboring the pMON71270, and other constructs described in Examples 3 and 4, have at least one of the following phenotypes: increased germ mass (as a percent of kernel weight), increased whole kernel oil levels (as a percent of kernel weight), improved protein quality (increased lysine, tryptophan, threonine, isoleucine and methionine, for example), free amino acids (up or down) or increased micronutrient content, including tocopherols, tocotrienols, carotenoids, plastiquinols and phylloquinones.

Example 13

This example describes the histological analysis of tissues from transgenic maize plants.

Mature or developing kernels of fresh or frozen corn are sliced sagitally. Tissue slices of 1 mm or thinner are stained for 1 to 2 min in a solution of 0.01% aniline blue C.I. 42755 (Baker, Phillipsburg, N.J.) in 0.1M phosphate buffer, pH 8.0. Samples are rinsed in 0.1 M phosphate buffer, pH 8.0, and examined with either of a standard fluorescent microscope using a narrow violet cube Nikon V-4 (EX 380-420 nm, DM 430 nm, BA 450 nm) or an ultraviolet light source (EX330-380, DM400, BA420). Alternatively, samples can be visualized using a confocal microscope using an Argon-ion laser (emission wavelength 488 nm and 514 nm). Aniline blue stains the cell walls and nuclei of plants (Smith and McCully, Stain Technology, 53(2):79-85 (1978)). Cell size is determined by using an outlining tool in the Nikon EZ C-1 software. Approximately 25 to 50 cells are outlined and the area the cells occupy is recorded and the average area per cell is calculated.

Histological analysis of events containing pMON71270 yielded 3 events that demonstrated a significant increase in cell number as characterized by more cells per unit area in the embryo (1.3×, 1.7×, 2.4×, p=0.05) with no reduction in embryo mass.

Histological analysis of events containing pMON71279 gave 3 events with wild-type cell number per unit area (1.1×, 0.97×, 0.96×, p=0.05), but due to increased embryo mass, yielded an increase in the total number of cells per embryo.

To determine mitotic indices, corn tissues are fixed, stained with a fluorescent probe, cleared and imaged using fluorescent microscopy or confocal scanning laser microscopy (CLSM). Mitotic index is determined by counting the number of cells in an area that are in prometaphase, metaphase or anaphase and reported as a percentage. For example, corn tissue can be fixed in formalin, propinionic acid and ethanol, stained with propidium iodide and cleared with xylene (Running et al., Confocal Microscopy of the Shoot Apex, *Methods in Cell Biology*, 49:217-229 (1995)).

Example 14

This example describes how to measure CDK inhibitor activity.

Protein extracts from transgenic and non-transgenic plant tissues are enriched for CDK using p13Suc1 resin (Oncogene Sciences, Cambridge, Mass.), and histone H1 kinase assays are performed (Wang et al., *Plant J.*, 15:501-510 (1998)). Transgenic plant tissues with increased CDK inhibitor activity have reduced kinase activity, whereas transgenic plant tissues with reduced CDK inhibitor activity have increased kinase activity.

The following references are specifically incorporated herein by reference:

Birren et al., *Genome Analysis: A Laboratory Manual Series, Volume* 1, *Analyzing DNA*, Cold Spring Harbor Laboratory Press, Cold Spring Harbor, N.Y. (1997), Birren et al., *Genome Analysis: A Laboratory Manual Series, Volume* 2, *Detecting Genes*, Cold Spring Harbor Laboratory Press, Cold Spring Harbor, N.Y. (1998), Birren et al., *Genome Analysis: A Laboratory Manual Series, Volume* 3, *Cloning Systems*, Cold Spring Harbor Laboratory Press, Cold Spring Harbor, N.Y. (1999), Birren et al., Genome Analysis: A Laboratory Manual Series, Volume 4, *Mapping Genomes*, Cold Spring Harbor Laboratory Press, Cold Spring Harbor, N.Y. (1999), Harlow et al., *Antibodies: A Laboratory Manual*, Cold Spring Harbor Laboratory Press, Cold Spring Harbor, N.Y. (1988), Harlow et al., *Using Antibodies: A Laboratory Manual*, Cold Spring Harbor Laboratory Press, Cold Spring Harbor, N.Y. (1999), Sambrook et al., *Molecular Cloning: A Laboratory Manual*, 2nd edition, Cold Spring Harbor Laboratory Press, Cold Spring Harbor, N.Y. (1989), Ausubel et al., *Current Protocols in Molecular Biology*, John Wiley & Sons, Inc., NY (1999), and Croy, *Plant Molecular Biology Labfase*, BIOS Scientific Publications, Ltd. (UK) and Blackwell Scientific Publications (UK) (1993).

All references, including publications, patent applications, and patents, cited herein are hereby incorporated by reference to the same extent as if each reference were individually and specifically indicated to be incorporated by reference and were set forth in its entirety herein.

While this invention has been described with an emphasis upon preferred embodiments, it will be apparent to those of ordinary skill in the art that variations in the preferred embodiments can be prepared and used and that the invention can be practiced otherwise than as specifically described herein. The present invention is intended to include such variations and alternative practices. Accordingly, this invention includes all modifications encompassed within the spirit and scope of the invention as defined by the following claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated or purified nucleic acid molecule comprising a nucleotide sequence selected from the group consisting of:
   (i) the nucleotide sequence of SEQ ID NO: 1,
   (ii) a nucleotide sequence encoding the amino acid sequence of SEQ ID NO: 2, and
   (iii) a nucleotide sequence encoding an amino acid sequence that is at least 95% identical to the amino acid sequence of SEQ ID NO:2, and that has CDK inhibitor-like activity.

2. The isolated or purified nucleic acid molecule of claim 1 operably linked to a promoter that is preferentially expressed in the male reproductive tissue of maize.

3. The isolated or purified nucleic acid molecule of claim 2, wherein the promoter is the SILKY1 promoter of maize, the NTM19 promoter of tobacco, the PCA55 promoter of maize, the NPG 1 promoter of tobacco, the AP3 promoter of Arabidopsis, the Bgp1 promoter of Brassica, an anther-prefeffed promoter, a pollen-preferred promoter, or a microspore-preferred promoter.

4. A vector comprising the isolated or purified nucleic acid molecule of any one of claims 1-3.

5. A host plant cell comprising the isolated or purified nucleic acid molecule of any one of claims 1-3, optionally in the form of a vector.

6. A transgenic plant comprising the isolated or purified nucleic acid molecule of claim 1.

7. A seed comprising the isolated or purified nucleic acid molecule of claim 1.

8. Meal obtained from the seed of claim 7, wherein the meal comprises said isolated or purified nucleic acid molecule of claim 1.

9. The plant of claim 6, wherein the plant is a maize plant.

* * * * *

UNITED STATES PATENT AND TRADEMARK OFFICE
CERTIFICATE OF CORRECTION

PATENT NO.        : 7,329,799 B2                                         Page 1 of 1
APPLICATION NO.   : 10/890629
DATED             : February 12, 2008
INVENTOR(S)       : Savidge et al.

It is certified that error appears in the above-identified patent and that said Letters Patent is hereby corrected as shown below:

In claim 3, column 84, line 2, delete "prefeffed" and insert --preferred--.

Signed and Sealed this

Eleventh Day of May, 2010

David J. Kappos
*Director of the United States Patent and Trademark Office*

SEQUENCE LISTING

```
<160> NUMBER OF SEQ ID NOS: 59

<210> SEQ ID NO 1
<211> LENGTH: 642
<212> TYPE: DNA
<213> ORGANISM: Zea mays

<400> SEQUENCE: 1 atgggaagt acatgcgcaa gggcaaggtg tccggggagg tcgccgtcat ggaggtaccc      60
ggcggcgcgc tgctcggcgt ccgcacccgc tcccgcacgc tcgcgctgca gcgcgcgcag     120
aggccgctcg acaagggcga cgcggaggac gccgccgcgg agtacctcga gctcaggagc     180
cggaggctcg agaagccgca caaggagcat ccgtcgccgc ccgcgaccgc gaccaagagg     240
ggcgccggga ggaaggccgc cgccgccgcc gcggtgcagc acgtgctgat gcaggacgag     300
gtcgaggtcg aggtctcgtt cggggacaac gtgcttgact tggacaccat ggaaaggagt     360
accagagaga caacaccgtg cagcctgatt aggaacccag agatgataag caccccagga     420
tccacaacta aaagcaaaac cagcagcaac tcgacgactt cccgccgcag aacggaggaa     480
accccgagct gccggttcat accgagctcg ctcgagatgg aggagttctt ctcggcggcc     540
gagcaacagg agcagcatag cttcagggag aagtacaact tctgtcccgt gaacgactgt     600
cctctccctg gccggtacga atgggcgagg ctagactgct ag                       642

<210> SEQ ID NO 2
<211> LENGTH: 213
```

```
<212> TYPE: PRT
<213> ORGANISM: Zea mays

<400> SEQUENCE: 2

Met Gly Lys Tyr Met Arg Lys Gly Lys Val Ser Gly Glu Val Ala Val
1               5                   10                  15

Met Glu Val Pro Gly Gly Ala Leu Leu Gly Val Arg Thr Arg Ser Arg
            20                  25                  30

Thr Leu Ala Leu Gln Arg Ala Gln Arg Pro Leu Asp Lys Gly Asp Ala
        35                  40                  45

Glu Asp Ala Ala Glu Tyr Leu Glu Leu Arg Ser Arg Arg Leu Glu
50                  55                  60

Lys Pro His Lys Glu His Pro Ser Pro Pro Ala Thr Ala Thr Lys Arg
65              70                  75                  80

Gly Ala Gly Arg Lys Ala Ala Ala Ala Ala Val Gln His Val Leu
                85                  90                  95

Met Gln Asp Glu Val Glu Val Glu Val Ser Phe Gly Asp Asn Val Leu
            100                 105                 110

Asp Leu Asp Thr Met Glu Arg Ser Thr Arg Glu Thr Thr Pro Cys Ser
        115                 120                 125

Leu Ile Arg Asn Pro Glu Met Ile Ser Thr Pro Gly Ser Thr Thr Lys
    130                 135                 140

Ser Lys Thr Ser Ser Asn Ser Thr Thr Ser Arg Arg Arg Thr Glu Glu
145                 150                 155                 160

Thr Pro Ser Cys Arg Phe Ile Pro Ser Ser Leu Glu Met Glu Glu Phe
                165                 170                 175

Phe Ser Ala Ala Glu Gln Gln Glu Gln His Ser Phe Arg Glu Lys Tyr
            180                 185                 190

Asn Phe Cys Pro Val Asn Asp Cys Pro Leu Pro Gly Arg Tyr Glu Trp
        195                 200                 205

Ala Arg Leu Asp Cys
    210

<210> SEQ ID NO 3
<211> LENGTH: 654
<212> TYPE: DNA
<213> ORGANISM: Zea mays

<400> SEQUENCE: 3
atggggaagt acatgcgcaa gggcaagatg tccggggagg tggccgtcat ggaggtcccc      60
ggcggcgcgc tgctgggtgt ccgcacccgc tcccgcacgc tcgcgctgca gagggcgcag     120
aggccgctcg acaaggggga cgcggatgac gccgccggac agtacctcga gctcaggagc     180
cggaggctcg agaagcctca taaggaccat cagccgctgc cgctgccgct gccgccgccc     240
gcccccgcag ccaagagggg cgccgggagg aaggccgcct ccaccgccgc cgcgccaaac     300
gcgctggcgg aggacgaggt cgaggtcgag gtctccttcg gggagaacgt gcttgacttg     360
gacgccatgg aaaggagtac cagagagaca acaccgtgta gtttgatcag gaacccagag     420
atgataagca ccccaggatc cacaactaaa gtaaaacca gcaactcgac gacttcccgt      480
cgcaggatgg aaacctcagt ctgccgtttc ataccgagtt cgctcgagat ggaagagttc     540
ttctcggccg ctgaacaaca ggagcagcat aacttcaggg agaagtataa cttctgtcct     600
gtgaacgact gccctctccc gggtcgatat gagtgggcga ggctagactg ttag           654

<210> SEQ ID NO 4
```

<211> LENGTH: 217
<212> TYPE: PRT
<213> ORGANISM: Zea mays

<400> SEQUENCE: 4

Met Gly Lys Tyr Met Arg Lys Gly Lys Met Ser Gly Glu Val Ala Val
1               5                   10                  15

Met Glu Val Pro Gly Gly Ala Leu Leu Gly Val Arg Thr Arg Ser Arg
            20                  25                  30

Thr Leu Ala Leu Gln Arg Ala Gln Arg Pro Leu Asp Lys Gly Asp Ala
        35                  40                  45

Asp Asp Ala Ala Gly Gln Tyr Leu Glu Leu Arg Ser Arg Arg Leu Glu
    50                  55                  60

Lys Pro His Lys Asp His Gln Pro Leu Pro Leu Pro Leu Pro Pro Pro
65                  70                  75                  80

Ala Pro Ala Ala Lys Arg Gly Ala Gly Arg Lys Ala Ala Ser Thr Ala
                85                  90                  95

Ala Ala Pro Asn Ala Leu Ala Glu Asp Glu Val Glu Val Glu Val Ser
            100                 105                 110

Phe Gly Glu Asn Val Leu Asp Leu Asp Ala Met Glu Arg Ser Thr Arg
        115                 120                 125

Glu Thr Thr Pro Cys Ser Leu Ile Arg Asn Pro Glu Met Ile Ser Thr
    130                 135                 140

Pro Gly Ser Thr Thr Lys Ser Lys Thr Ser Asn Ser Thr Thr Ser Arg
145                 150                 155                 160

Arg Arg Met Glu Thr Ser Val Cys Arg Phe Ile Pro Ser Ser Leu Glu
                165                 170                 175

Met Glu Glu Phe Phe Ser Ala Ala Glu Gln Gln Glu Gln His Asn Phe
            180                 185                 190

Arg Glu Lys Tyr Asn Phe Cys Pro Val Asn Asp Cys Pro Leu Pro Gly
        195                 200                 205

Arg Tyr Glu Trp Ala Arg Leu Asp Cys
    210                 215

<210> SEQ ID NO 5
<211> LENGTH: 342
<212> TYPE: DNA
<213> ORGANISM: Zea mays

<400> SEQUENCE: 5
ttatcagtca tcacctccca actcgcaacg cacccacagt ccctcaccgg ctcaccgccc     60
gcaccgcaca caggcgccac gaagcagaaa agtatggccg ctgccacagc gacggcggcg    120
gtgctgggat gcagcaggcg ccagagcgac attgcgggcg ccggcatacc gaagaaggga    180
aaggtgggga ggtcgccgcc ggcggaggag gtggaggcgt cctcgccgc agcggagcgc     240 ggcatggcgc ggcgcttcgc ggtcaagtac aactatgacg tcgtcaagga cgctcccatg    300
gacggcggcc ggtacgagtg ggtccgagtg cggcccggtt aa                      342

<210> SEQ ID NO 6
<211> LENGTH: 129
<212> TYPE: PRT
<213> ORGANISM: Zea mays

<400> SEQUENCE: 6

Ala Cys Arg Tyr Arg Ser Gly Ile Pro Gly Ser Thr His Ala Ser Ala
1               5                   10                  15

```
Leu Ser Val Ile Thr Ser Gln Leu Ala Thr His Pro Gln Ser Leu Thr
             20                  25                  30

Gly Ser Pro Ala Pro His Thr Gly Ala Thr Lys Gln Lys Ser Met
         35                  40                  45

Ala Ala Ala Thr Ala Thr Ala Ala Val Leu Gly Cys Ser Arg Arg Gln
 50                  55                  60

Ser Asp Ile Ala Gly Ala Gly Ile Pro Lys Lys Gly Lys Val Gly Arg
 65                  70                  75                  80

Ser Pro Pro Ala Glu Glu Val Glu Ala Phe Leu Ala Ala Glu Arg
                 85                  90                  95

Gly Met Ala Arg Arg Phe Ala Val Lys Tyr Asn Tyr Asp Val Val Lys
             100                 105                 110

Asp Ala Pro Met Asp Gly Gly Arg Tyr Glu Trp Val Arg Val Arg Pro
             115                 120                 125

Gly
```

```
<210> SEQ ID NO 7
<211> LENGTH: 573
<212> TYPE: DNA
<213> ORGANISM: Zea mays

<400> SEQUENCE: 7
atgggcaagt acatgcgcaa ggccaaggct tccagcgagg ttgtcatcat ggatgtcgcc      60
gccgctccgc tcggagtccg cacccgagcg cgcgccctcg cgctgcagcg tctgcaggag     120
caacagacgc agtgggaaga aggtgctggc ggcgagtacc tggagctaag gaaccggagg     180
ctcgagaagc tgccgccgcc gccggcgacc actaggaggt cgggcgggag gaaagcggca     240
gccgaggccg ccgcaactaa ggaggctgag gcgtcgtacg gggagaacat gctcgagttg     300
gaggccatgg agaggattac cagggagacg acgccttgca gcttgattaa cacccagatg     360
actagcactc ctgggtccac gagatccagc cactcttgcc accgcagggt gaacgctcct     420
ccggtgcacg ccgtcccaag ttctagggag atgaatgagt acttcgctgc cgaacagcga     480
cggcaacagc aggatttcat tgacaagtac aacttcgatc ctgcaaacga ctgccctctc     540
ccaggcaggt ttgagtgggt gaagctagac tga                                  573
```

```
<210> SEQ ID NO 8
<211> LENGTH: 190
<212> TYPE: PRT
<213> ORGANISM: Zea mays

<400> SEQUENCE: 8

Met Gly Lys Tyr Met Arg Lys Ala Lys Ala Ser Ser Glu Val Val Ile
 1               5                  10                  15

Met Asp Val Ala Ala Ala Pro Leu Gly Val Arg Thr Arg Ala Arg Ala
             20                  25                  30

Leu Ala Leu Gln Arg Leu Gln Glu Gln Gln Thr Gln Trp Glu Glu Gly
         35                  40                  45

Ala Gly Gly Glu Tyr Leu Glu Leu Arg Asn Arg Leu Glu Lys Leu
 50                  55                  60

Pro Pro Pro Pro Ala Thr Thr Arg Arg Ser Gly Gly Arg Lys Ala Ala
 65                  70                  75                  80

Ala Glu Ala Ala Ala Thr Lys Glu Ala Glu Ala Ser Tyr Gly Glu Asn
                 85                  90                  95

Met Leu Glu Leu Glu Ala Met Glu Arg Ile Thr Arg Glu Thr Thr Pro
             100                 105                 110
```

Cys Ser Leu Ile Asn Thr Gln Met Thr Ser Thr Pro Gly Ser Thr Arg
            115                 120                 125

Ser Ser His Ser Cys His Arg Arg Val Asn Ala Pro Pro Val His Ala
    130                 135                 140

Val Pro Ser Ser Arg Glu Met Asn Glu Tyr Phe Ala Ala Glu Gln Arg
145                 150                 155                 160

Arg Gln Gln Gln Asp Phe Ile Asp Lys Tyr Asn Phe Asp Pro Ala Asn
                165                 170                 175

Asp Cys Pro Leu Pro Gly Arg Phe Glu Trp Val Lys Leu Asp
            180                 185                 190

<210> SEQ ID NO 9
<211> LENGTH: 651
<212> TYPE: DNA
<213> ORGANISM: Zea mays

<400> SEQUENCE: 9
atgggcaagt gcgtgaggat ccgcggcagc agcaagccgc gcgccgccgc cgccgcggcg    60
gcgtcgtgcc tcacgctgtg cagcgggcgc cgcgtgccgc cgtcggaggc gtcggcggcg   120
tgcagcccga ggacgagaag caggccgcgg cgccaccgcg gggcaggcct ccggcggtgg   180
tgcggcgcca aggagagcgc gtacggcgga agccccggc gccacagggg cgagggcgag    240
gccgacgcgc ggagccccg tggccgggtg ctcggtgtcg gtgcccgcca gcagcagctc   300
tgcgccgacg acgggctcgg ccagcagcac gaggaggagg cgtctgcgac gatggccggc   360
gactgcgacg acggcgcggg cgtggcgaaa gtgaataagg cgaataaaca cgagaacgac   420
gagtgcggct gccgcgtcgt cggcggcgtc gccagccaga cgccgtcgcc gtcgccgtcg   480
ccgccaccgc cgccgacgga aaccgagata gaggccttct tcgcggacgc ggagctggcc   540
gagcgccggc gattcgcaga ggcgtacaat tacgacgtcg ccctcgaccg cccgctggag   600
gggcgcttcg agtgggtgcc gctgccgctg acgggggtc ggaggtggta a             651

<210> SEQ ID NO 10
<211> LENGTH: 216
<212> TYPE: PRT
<213> ORGANISM: Zea mays

<400> SEQUENCE: 10

Met Gly Lys Cys Val Arg Ile Arg Gly Ser Ser Lys Pro Arg Ala Ala
1               5                   10                  15

Ala Ala Ala Ala Ser Cys Leu Thr Leu Cys Ser Gly Arg Arg Val
            20                  25                  30

Pro Pro Ser Glu Ala Ser Ala Ala Cys Ser Pro Arg Thr Arg Ser Arg
            35                  40                  45

Pro Arg Arg His Arg Gly Ala Gly Leu Arg Arg Trp Cys Gly Ala Lys
    50                  55                  60

Glu Ser Ala Tyr Gly Gly Ser Pro Arg Arg His Arg Gly Glu Gly Glu
65                  70                  75                  80

Ala Asp Ala Arg Ser Pro Arg Gly Arg Val Leu Gly Val Gly Ala Arg
                85                  90                  95

Gln Gln Gln Leu Cys Ala Asp Asp Gly Leu Gly Gln Gln His Glu Glu
            100                 105                 110

Glu Ala Ser Ala Thr Met Ala Gly Asp Cys Asp Asp Gly Ala Gly Val
            115                 120                 125

Ala Lys Val Asn Lys Ala Asn Lys His Glu Asn Asp Glu Cys Gly Cys

```
                130               135               140
Arg Val Val Gly Gly Val Ala Ser Gln Thr Pro Ser Pro Ser Pro Ser
145               150                   155                   160

Pro Pro Pro Pro Pro Thr Glu Thr Glu Ile Glu Ala Phe Phe Ala Asp
                165                   170                   175

Ala Glu Leu Ala Glu Arg Arg Arg Phe Ala Glu Ala Tyr Asn Tyr Asp
            180                   185                   190

Val Ala Leu Asp Arg Pro Leu Glu Gly Arg Phe Glu Trp Val Pro Leu
                195                   200                   205

Pro Leu Thr Gly Gly Arg Arg Trp
    210                   215

<210> SEQ ID NO 11
<211> LENGTH: 765
<212> TYPE: DNA
<213> ORGANISM: Zea mays

<400> SEQUENCE: 11
atggggaagt acatgcgcaa gtgcaggggc gccgcaggcg cggaggtcgc cgccgtcgag      60
gttacgcagg tcgtcggcgt ccggacgagg tccaggtccg cggcggcgac cggcggtgtc    120
gcgaaggtcg ccccgaggag gaagagggcg ccggcggggg arcctgctgc cgccgtgagc    180
gctggtgggg acggcggaag ctgctacatc cacctgcgta ccgcatgct gttcatggca     240 ccgcctcagc cgcagccgtc ggttccgacc ccggcggcgg aggctgctga tggcgctgca    300
ggacagcagg gcgcggtgct cgcggccggg ctctcgcgct gctccagcac ggcgtcgtcg    360
gtgaacttgg ggttgggggg tcagcgcggg agccacacct gccgctccga cgacgctgca    420
gaggctggcg gggatcacgt cctggtggtg atgtctcgg cgagcaactc cgggagcggc     480
ccagaccgcg agaggagaga cgacgccca tcgagccggg cgcacggcga gctcagcgat     540
ctggagtcgg atctgcgggg gcacaagact ggccgtcgc taccggcggc aacgccggct    600
gcggagctga tcgtgccgcc agcacacgag atccaggagt tcttcgccgc cgccgaggcg    660
gcccaggcca agcgctttgc ttccaagtac aacttcgact tcgtccgcgg cgtgcccctc    720
gacgccggcg gccggttcga gtgggcgccg gtggtcagca tctga                    765

<210> SEQ ID NO 12
<211> LENGTH: 254
<212> TYPE: PRT
<213> ORGANISM: Zea mays

<400> SEQUENCE: 12

Met Gly Lys Tyr Met Arg Lys Cys Arg Gly Ala Ala Gly Ala Glu Val
1               5                   10                  15

Ala Ala Val Glu Val Thr Gln Val Val Gly Val Arg Thr Arg Ser Arg
            20                  25                  30

Ser Ala Ala Thr Gly Gly Val Lys Val Ala Pro Arg Arg Lys
        35                  40                  45

Arg Ala Pro Ala Gly Glu Pro Ala Ala Val Ser Ala Gly Asp
    50                  55                  60

Gly Gly Ser Cys Tyr Ile His Leu Arg Ser Arg Met Leu Phe Met Ala
65                  70                  75                  80

Pro Pro Gln Pro Gln Pro Ser Val Pro Thr Pro Ala Ala Glu Ala Ala
                85                  90                  95

Asp Gly Ala Ala Gly Gln Gln Gly Ala Val Leu Ala Ala Gly Leu Ser
            100                 105                 110
```

```
Arg Cys Ser Ser Thr Ala Ser Ser Val Asn Leu Gly Leu Gly Gly Gln
            115                 120                 125

Arg Gly Ser His Thr Cys Arg Ser Asp Asp Ala Ala Glu Ala Gly Gly
        130                 135                 140

Asp His Val Leu Val Val Asp Val Ser Ala Ser Asn Ser Gly Ser Gly
145                 150                 155                 160

Pro Asp Arg Glu Arg Glu Thr Thr Pro Ser Ser Arg Ala His Gly
                165                 170                 175

Glu Leu Ser Asp Leu Glu Ser Asp Leu Ala Gly His Lys Thr Gly Pro
            180                 185                 190

Ser Leu Pro Ala Ala Thr Pro Ala Ala Glu Leu Ile Val Pro Pro Ala
        195                 200                 205

His Glu Ile Gln Glu Phe Phe Ala Ala Glu Ala Gln Ala Lys
    210                 215                 220

Arg Phe Ala Ser Lys Tyr Asn Phe Asp Phe Val Arg Gly Val Pro Leu
225                 230                 235                 240

Asp Ala Gly Gly Arg Phe Glu Trp Ala Pro Val Val Ser Ile
                245                 250
```

<210> SEQ ID NO 13
<211> LENGTH: 717
<212> TYPE: DNA
<213> ORGANISM: Zea mays

<400> SEQUENCE: 13

```
gtcgccgccg tcgaggttac gcaggtcgtc ggcgtccgca cgaggtccag gtccgcggcg      60
gcgaccggcg gtgtcgcgaa ggtcgtcgcc ccgaggagga agagggcgcc ggcgggggag     120
cctgctgcct ccgtgggcgc tggtggggac ggcggaagct gctacatcca cctgcgtagc     180
cgcatgctgt tcatggcacc gcctcagccg cagccgccgt cggttccgac cccggcggag     240
gctgctgatg gcgctgcagg acagcagggc gcggcgctcg cggccgggct ctcgcgttgc     300
tccagcacgg cgtcgtcggt gcacgtgggg ggtcagcgcg ggagccacac ctgccgctcc     360
gacgacgctg cagaggctgg cggggatcac gtcctggtgg atgtctcggc ggcgagcaac     420
tccgggagcg gcccagaccg cgagaggcga gagacgacgc catcgagccg gcgcacggc      480
gagctcagcg atctggagtc ggatctggcg gggcacaaga ctggcccgtc gctaccggcg     540
gcaacgccgg ctgcggagct gatcgtgccg ccagcacacg agatccagga gttcttcgcc     600
gccgccgagg cggcccaggc caagcgcttt gcttccaagt acaacttcga cttcgtccgt     660
ggcgtgcccc tcgacgccgg cggccggttc gagtgggcgc cggtggtcag catctga       717
```

<210> SEQ ID NO 14
<211> LENGTH: 238
<212> TYPE: PRT
<213> ORGANISM: Zea mays

<400> SEQUENCE: 14

```
Val Ala Ala Val Glu Val Thr Gln Val Val Gly Val Arg Thr Arg Ser
1               5                   10                  15

Arg Ser Ala Ala Ala Thr Gly Gly Val Ala Lys Val Val Ala Pro Arg
            20                  25                  30

Arg Lys Arg Ala Pro Ala Gly Glu Pro Ala Ala Ser Val Gly Ala Gly
        35                  40                  45

Gly Asp Gly Gly Ser Cys Tyr Ile His Leu Arg Ser Arg Met Leu Phe
    50                  55                  60
```

Met Ala Pro Pro Gln Pro Gln Pro Pro Ser Val Pro Thr Pro Ala Glu
 65                  70                  75                  80

Ala Ala Asp Gly Ala Ala Gly Gln Gln Gly Ala Ala Leu Ala Ala Gly
                 85                  90                  95

Leu Ser Arg Cys Ser Ser Thr Ala Ser Ser Val His Val Gly Gly Gln
            100                 105                 110

Arg Gly Ser His Thr Cys Arg Ser Asp Ala Ala Glu Ala Gly Gly
            115                 120                 125

Asp His Val Leu Val Asp Val Ser Ala Ala Ser Asn Ser Gly Ser Gly
            130                 135                 140

Pro Asp Arg Glu Arg Glu Thr Thr Pro Ser Ser Arg Ala His Gly
145                 150                 155                 160

Glu Leu Ser Asp Leu Glu Ser Asp Leu Ala Gly His Lys Thr Gly Pro
                165                 170                 175

Ser Leu Pro Ala Ala Thr Pro Ala Ala Glu Leu Ile Val Pro Pro Ala
            180                 185                 190

His Glu Ile Gln Glu Phe Phe Ala Ala Glu Ala Ala Gln Ala Lys
            195                 200                 205

Arg Phe Ala Ser Lys Tyr Asn Phe Asp Phe Val Arg Gly Val Pro Leu
210                 215                 220

Asp Ala Gly Gly Arg Phe Glu Trp Ala Pro Val Val Ser Ile
225                 230                 235

<210> SEQ ID NO 15
<211> LENGTH: 699
<212> TYPE: DNA
<213> ORGANISM: Zea mays

<400> SEQUENCE: 15

```
atggggaagt acatgcgcaa gcgcaggggg gccgcgggcg aggggdtggc cgcagtcgag    60
gtctcgcagg tcgtcggcgt ccggacgagg tccaggtccg cggcggcgac cggcggcggt   120
gtcgcgaagg tcgctccgcc gaggaggaag aaggcgctgc tgcccgccgc gaacgagacg   180
gcgtcggggg agcctggtgc cgtgggcggt ggtggtgggg acggcggaag ctgctgctac   240
atccacctgc ggagccgcat gctgttcatg gcagcacctc agcagcaacc gtcggcggct   300
ccgacgcccg cggaggctgc tggtgcggca cagcagggcg gggtggtggc gctcgcggct   360
ggcctctcgc gttgctccag cacggcgtcg acggtggacg tcggggggcca gcagcccgcg   420
agcgggagcc acgcctgccg ctccgacgct gcggaggttg ccgggatca cgtcccggat   480
gtcgtcaccg cgagcaactc ggggagcgtc ccggaccgcg agaggagaga gacgacgcca   540
tcgtcgagcc gggcgcacgg cggcgagctc agcgatctgg agtcggatct ggtggggtgg   600
cagaagactg gctgctcgtc gtcgccggcg acaacaacgt cggctgcgga gctgatcgtg   660
ccgccagcac aggagatcca ggaattcttc gcggccgct                           699
```

<210> SEQ ID NO 16
<211> LENGTH: 232
<212> TYPE: PRT
<213> ORGANISM: Zea mays

<400> SEQUENCE: 16

Met Gly Lys Tyr Met Arg Lys Arg Arg Gly Ala Ala Gly Glu Gly Val
  1               5                  10                  15

Ala Ala Val Glu Val Ser Gln Val Val Gly Val Arg Thr Arg Ser Arg
                 20                  25                  30

-continued

Ser Ala Ala Thr Gly Gly Val Ala Lys Val Ala Pro Pro Arg
    35              40              45

Arg Lys Lys Ala Leu Leu Pro Ala Ala Asn Glu Thr Ala Ser Gly Glu
50                  55                  60

Pro Gly Ala Val Gly Gly Gly Gly Asp Gly Ser Cys Cys Tyr
65              70              75              80

Ile His Leu Arg Ser Arg Met Leu Phe Met Ala Ala Pro Gln Gln Gln
                85                  90                  95

Pro Ser Ala Ala Pro Thr Pro Ala Glu Ala Gly Ala Ala Gln Gln
            100                 105                 110

Gly Gly Val Val Ala Leu Ala Ala Gly Leu Ser Arg Cys Ser Ser Thr
        115                 120                 125

Ala Ser Thr Val Asp Val Gly Gln Gln Pro Ala Ser Gly Ser His
    130                 135                 140

Ala Cys Arg Ser Asp Ala Ala Glu Val Ala Gly Asp His Val Pro Asp
145                 150                 155                 160

Val Val Thr Ala Ser Asn Ser Gly Ser Val Pro Asp Arg Glu Arg Arg
                165                 170                 175

Glu Thr Thr Pro Ser Ser Ser Arg Ala His Gly Gly Glu Leu Ser Asp
            180                 185                 190

Leu Glu Ser Asp Leu Val Gly Trp Gln Lys Thr Gly Cys Ser Ser Ser
        195                 200                 205

Pro Ala Thr Thr Thr Ser Ala Ala Glu Leu Ile Val Pro Pro Ala Gln
    210                 215                 220

Glu Ile Gln Glu Phe Phe Ala Ala
225                 230

<210> SEQ ID NO 17
<211> LENGTH: 183
<212> TYPE: DNA
<213> ORGANISM: Zea mays

<400> SEQUENCE: 17
cactcttccc accgcagggt gaaagctcct cctgtgcacg ccctcccaag ttcaacggag    60
atgaacgagt acttcgctgc tgaacagcga cgccaacaac aggctttcat tgacaagtac   120
aactttgatc ctgtaaatga ctgccctctc ccaggcaggt ttgaatgggt gaagctagac   180
tga                                                                 183

<210> SEQ ID NO 18
<211> LENGTH: 60
<212> TYPE: PRT
<213> ORGANISM: Zea mays

<400> SEQUENCE: 18

His Ser Ser His Arg Arg Val Lys Ala Pro Pro Val His Ala Leu Pro
1               5                   10                  15

Ser Ser Thr Glu Met Asn Glu Tyr Phe Ala Ala Glu Gln Arg Arg Gln
            20                  25                  30

Gln Gln Ala Phe Ile Asp Lys Tyr Asn Phe Asp Pro Val Asn Asp Cys
        35                  40                  45

Pro Leu Pro Gly Arg Phe Glu Trp Val Lys Leu Asp
    50                  55                  60

<210> SEQ ID NO 19
<211> LENGTH: 200

<212> TYPE: DNA
<213> ORGANISM: Artificial
<220> FEATURE:
<223> OTHER INFORMATION: Primer

<400> SEQUENCE: 19
gcagcaactc gacgacttcc cgccgcagaa cggaggaaac ccgagctgc cggttcatac      60 cgagctcgct cgagatggag gagttcttct cggcggccga gcaacaggag cagcatagct    120
tcagggagaa gtacaacttc tgtcccgtga acgactgtcc tctccctggc cggtacgaat    180
gggcgaggct agactgctag                                                200

<210> SEQ ID NO 20
<211> LENGTH: 200
<212> TYPE: DNA
<213> ORGANISM: Artificial
<220> FEATURE:
<223> OTHER INFORMATION: Primer

<400> SEQUENCE: 20
aactaaaagt aaaaccagca actcgacgac ttcccgtcgc aggatggaaa cctcagtctg     60
ccgtttcata ccgagttcgc tcgagatgga agagttcttc tcggccgctg aacaacagga   120
gcagcataac ttcagggaga agtataactt ctgtcctgtg aacgactgcc ctctcccggg    180
tcgatatgag tgggcgaggc                                                200

<210> SEQ ID NO 21
<211> LENGTH: 200
<212> TYPE: DNA
<213> ORGANISM: Artificial
<220> FEATURE:
<223> OTHER INFORMATION: Primer

<400> SEQUENCE: 21
agagcgacat tgcgggcgcc ggcataccga agaagggaaa ggtggggagg tcgccgccgg     60
cggaggaggt ggaggcgttc ctcgccgcag cggagcgcgg catggcgcgg cgcttcgcgg    120
tcaagtacaa ctatgacgtc gtcaaggacg ctcccatgga cggcggccgg tacgagtggg    180
tccgagtgcg gcccggttaa                                                200

<210> SEQ ID NO 22
<211> LENGTH: 200
<212> TYPE: DNA
<213> ORGANISM: Artificial
<220> FEATURE:
<223> OTHER INFORMATION: Primer

<400> SEQUENCE: 22
ggtccacgag atccagccac tcttgccacc gcagggtgaa cgctcctccg gtgcacgccg     60
tcccaagttc tagggagatg aatgagtact tcgctgccga acagcgacgg caacagcagg    120
atttcattga caagtacaac ttcgatcctg caaacgactg ccctctccca ggcaggtttg    180
agtgggtgaa gctagactga                                                200

<210> SEQ ID NO 23
<211> LENGTH: 200
<212> TYPE: DNA
<213> ORGANISM: Artificial
<220> FEATURE:
<223> OTHER INFORMATION: Primer

<400> SEQUENCE: 23

```
ccagccagac gccgtcgccg tcgccgtcgc cgccaccgcc gccgacggaa accgagatag    60
aggccttctt cgcggacgcg gagctggccg agcgccggcg attcgcagag gcgtacaatt   120
acgacgtcgc cctcgaccgc ccgctggagg ggcgcttcga gtgggtgccg ctgccgctga   180 cgggggggtcg gaggtggtaa                                              200

<210> SEQ ID NO 24
<211> LENGTH: 200
<212> TYPE: DNA
<213> ORGANISM: Artificial
<220> FEATURE:
<223> OTHER INFORMATION: Primer

<400> SEQUENCE: 24
ccatcgagcc gggcgcacgg cgagctcagc gatctggagt cggatctggc ggggcacaag    60
actggcccgt cgctaccggc ggcaacgccg gctgcggagc tgatcgtgcc gccagcacac   120
gagatccagg agttcttcgc cgccgccgag gcggcccagg ccaagcgctt tgcttccaag   180
tacaacttcg acttcgtccg                                               200

<210> SEQ ID NO 25
<211> LENGTH: 200
<212> TYPE: DNA
<213> ORGANISM: Artificial
<220> FEATURE:
<223> OTHER INFORMATION: Primer

<400> SEQUENCE: 25
tcggggagcg tcccggaccg cgagaggaga gagacgacgc catcgtcgag ccgggcgcac    60
ggcggcgagc tcagcgatct ggagtcggat ctggtggggt ggcagaagac tggctgctcg   120
tcgtcgccgg cgacaacaac gtcggctgcg gagctgatcg tgccgccagc acaggagatc   180
caggaattct tcgcggccgc                                               200

<210> SEQ ID NO 26
<211> LENGTH: 183
<212> TYPE: DNA
<213> ORGANISM: Artificial
<220> FEATURE:
<223> OTHER INFORMATION: Primer

<400> SEQUENCE: 26
cactcttccc accgcagggt gaaagctcct cctgtgcacg ccctcccaag ttcaacggag    60
atgaacgagt acttcgctgc tgaacagcga cgccaacaac aggctttcat tgacaagtac   120
aactttgatc ctgtaaatga ctgccctctc ccaggcaggt ttgaatgggt gaagctagac   180
tga                                                                 183

<210> SEQ ID NO 27
<211> LENGTH: 804
<212> TYPE: DNA
<213> ORGANISM: Zea mays

<400> SEQUENCE: 27
accgtcttcg gtacgcgctc actccgccct ctgcctttgt tactgccacg tttctctgaa    60
tgctctcttg tgtggtgatt gctgagagtg gtttagctgg atctagaatt acactctgaa   120
atcgtgttct gcctgtgctg attacttgcc gtcctttgta gcagcaaaat atagggacat   180
ggtagtacga aacgaagata gaacctacac agcaatacga gaaatgtgta atttggtgct   240
tagcggtatt tatttaagca catgttggtg ttatagggca cttggattca gaagtttgct   300
```

```
gttaatttag gcacaggctt catactacat gggtcaatag tatagggatt catattatag    360
gcgatactat aataatttgt tcgtctgcag agcttattat ttgccaaaat tagatattcc    420
tattctgttt ttgtttgtgt gctgttaaat tgttaacgcc tgaaggaata aatataaatg    480
acgaaatttt gatgtttatc tctgctcctt tattgtgacc ataagtcaag atcagatgca    540
cttgttttaa atattgttgt ctgaagaaat aagtactgac agtattttga tgcattgatc    600
tgcttgtttg ttgtaacaaa atttaaaaat aaagagtttc cttttgttg ctctccttac    660 ctcctgatgg tatctagtat ctaccaactg acactatatt gcttctcttt acatacgtat    720
cttgctcgat gccttctccc tagtgttgac cagtgttact cacatagtct ttgctcattt    780
cattgtaatg cagataccaa gcgg                                          804
```

```
<210> SEQ ID NO 28
<211> LENGTH: 44
<212> TYPE: DNA
<213> ORGANISM: Artificial
<220> FEATURE:
<223> OTHER INFORMATION: Primer

<400> SEQUENCE: 28
gcaaggcctg cagcaactcg acgacttccc gccgcagaac ggag                    44

<210> SEQ ID NO 29
<211> LENGTH: 50
<212> TYPE: DNA
<213> ORGANISM: Artificial
<220> FEATURE:
<223> OTHER INFORMATION: Primer

<400> SEQUENCE: 29
cgtcgagttg ctggttttac ttttagttct agcagtctag cctcgcccat              50

<210> SEQ ID NO 30
<211> LENGTH: 45
<212> TYPE: DNA
<213> ORGANISM: Artificial
<220> FEATURE:
<223> OTHER INFORMATION: Primer

<400> SEQUENCE: 30
atgccggcgc ccgcaatgtc gctctgcctc gcccactcat atcga                   45

<210> SEQ ID NO 31
<211> LENGTH: 34
<212> TYPE: DNA
<213> ORGANISM: Artificial
<220> FEATURE:
<223> OTHER INFORMATION: Primer

<400> SEQUENCE: 31
gctagatcta gagcgacatt gcgggcgccg gcat                               34

<210> SEQ ID NO 32
<211> LENGTH: 38
<212> TYPE: DNA
<213> ORGANISM: Artificial
<220> FEATURE:
<223> OTHER INFORMATION: Primer

<400> SEQUENCE: 32
ggctggatct cgtggacctt aaccgggccg cactcgga                           38
```

<210> SEQ ID NO 33
<211> LENGTH: 29
<212> TYPE: DNA
<213> ORGANISM: Artificial
<220> FEATURE:
<223> OTHER INFORMATION: Primer

<400> SEQUENCE: 33
gctggatcct cagtctagct tcacccact                                    29

<210> SEQ ID NO 34
<211> LENGTH: 29
<212> TYPE: DNA
<213> ORGANISM: Artificial
<220> FEATURE:
<223> OTHER INFORMATION: Primer

<400> SEQUENCE: 34
gctagatctt cagtctagct tcacccact                                    29

<210> SEQ ID NO 35
<211> LENGTH: 35
<212> TYPE: DNA
<213> ORGANISM: Artificial
<220> FEATURE:
<223> OTHER INFORMATION: Primer

<400> SEQUENCE: 35
gctggatcct gcagggcctc gcccactcat atcga                             35

<210> SEQ ID NO 36
<211> LENGTH: 33
<212> TYPE: DNA
<213> ORGANISM: Artificial
<220> FEATURE:
<223> OTHER INFORMATION: Primer

<400> SEQUENCE: 36
gctagatcta ccgtcttcgg tacgcgctca ctc                               33

<210> SEQ ID NO 37
<211> LENGTH: 29
<212> TYPE: DNA
<213> ORGANISM: Artificial
<220> FEATURE:
<223> OTHER INFORMATION: Primer

<400> SEQUENCE: 37
gctggatccc cgcttggtat ctgcattac                                    29

<210> SEQ ID NO 38
<211> LENGTH: 30
<212> TYPE: DNA
<213> ORGANISM: Artificial
<220> FEATURE:
<223> OTHER INFORMATION: Primer

<400> SEQUENCE: 38
gcaccatggc cagccagacg ccgtcgccgt                                   30

<210> SEQ ID NO 39
<211> LENGTH: 44
<212> TYPE: DNA
<213> ORGANISM: Artificial
<220> FEATURE:
<223> OTHER INFORMATION: Primer

```
<400> SEQUENCE: 39
cgccgtgcgc ccggctcgat ggttaccacc tccgaccccc cgtc                    44

<210> SEQ ID NO 40
<211> LENGTH: 43
<212> TYPE: DNA
<213> ORGANISM: Artificial
<220> FEATURE:
<223> OTHER INFORMATION: Primer

<400> SEQUENCE: 40
cgcggtccgg gacgctcccc gacggacgaa gtcgaagttg tac                     43

<210> SEQ ID NO 41
<211> LENGTH: 31
<212> TYPE: DNA
<213> ORGANISM: Artificial
<220> FEATURE:
<223> OTHER INFORMATION: Primer

<400> SEQUENCE: 41
gctagatctt cggggagcgt cccggaccgc g                                  31

<210> SEQ ID NO 42
<211> LENGTH: 43
<212> TYPE: DNA
<213> ORGANISM: Artificial
<220> FEATURE:
<223> OTHER INFORMATION: Primer

<400> SEQUENCE: 42
caccctgcgg tgggaagagt ggcggccgcg aagaattcct gga                     43

<210> SEQ ID NO 43
<211> LENGTH: 41
<212> TYPE: DNA
<213> ORGANISM: Artificial
<220> FEATURE:
<223> OTHER INFORMATION: Primer

<400> SEQUENCE: 43
gagcgcgtac cgaagacggt tcagtctagc ttcacccatt c                       41

<210> SEQ ID NO 44
<211> LENGTH: 105
<212> TYPE: DNA
<213> ORGANISM: Zea mays

<400> SEQUENCE: 44
caggattccc cttgcgactg caccacgccc cacccaaacc cacctaccgc ctccgctccc   60
ctctccagcg agtcggggc acggacggga ccagacgacc aggcc                    105

<210> SEQ ID NO 45
<211> LENGTH: 363
<212> TYPE: DNA
<213> ORGANISM: Zea mays

<400> SEQUENCE: 45
attccccacc cagcacaaga gcaccattga tctgattgat atgtgtctac cacaccacaa   60
tgtgactagc tccgccgccg ccgccgtgga ccgtggagga ggcgcaacca actgtggatc  120
tcgatcgcat tagctttgtt gtctgttgta aaaattagag tagttagctt tgtagccgga  180
```

```
tgaatgatct tgtgtaacca acaggcgtgg ttcacccctg gtcacacaac ctcactgtaa      240
cctgttaact gctcaagctg ctgtaaccga accaatctca tgtacgtagg cctagcgcag      300
tcttctcatc tgttcgtagc tctcgaaatt gattgaatgg aattagagtt aaaatttgca      360
tgg                                                                    363

<210> SEQ ID NO 46
<211> LENGTH: 115
<212> TYPE: DNA
<213> ORGANISM: Zea mays

<400> SEQUENCE: 46
cccacaccca cctacctacc tacctaccac caacgcctcg gctcccctct ccagcgagcc      60
gcgaccgcgc ggcaggggaa gcttagcacg gacgggacca gctgacgacc aggcc          115

<210> SEQ ID NO 47
<211> LENGTH: 340
<212> TYPE: DNA
<213> ORGANISM: Zea mays

<400> SEQUENCE: 47
attcctccaa gcacaagagc accatttatc tgatgtgtct accacatgac tagcgccgcc      60
gccgccgccg aggaggcgta atcaactgga tcgcattagc tttcttgcct gttgtaaaaa     120
ttagagtagt tagcctgtag ttgaatggtc ctgtgtaacg aaacaggcgt ggttctgagt     180
tacaccccga tccccaacct cactgtaacc gtttgactgc tcgctcaagc tgtagccgaa     240
ccatccatct caagtagcgt aggcctagcg tattcatctg ttcctagttc tagttcttga     300
atggattaat cgaatgagat cattgttaga atctgcatgg                           340

<210> SEQ ID NO 48
<211> LENGTH: 196
<212> TYPE: DNA
<213> ORGANISM: Zea mays

<400> SEQUENCE: 48
ctgccagatc caatccaaga ggtcgcctcg tgtcctctcc tgtctgtctc tacttctctt      60
gtaaaagtcg cttactaccc gtgtaacgct tcgcttagct gtaactaaat tatgctcacg     120
agatgggatt aatcatgtga aggcccaacc ttgtacgtta gtggtgtgcg gttaacgtgt     180
ccttccttag tccaga                                                    196

<210> SEQ ID NO 49
<211> LENGTH: 217
<212> TYPE: DNA
<213> ORGANISM: Zea mays

<400> SEQUENCE: 49
gcgcgtaata cgactcacta tagggcgaat tgggtaccct cgaggccggc cgggtctccc      60
tcgttatttc cgggctccct cctgtgtaca ccactcccgc ccgcccacc attttatccc     120 cgcctctcct ggcctctgcc gccccgtcgc acagaatcgc ttggtgcacc ctgcgagggc     180
ctcctcgaaa ccctagcttg cccagcccct ccgggcc                              217

<210> SEQ ID NO 50
<211> LENGTH: 338
<212> TYPE: DNA
<213> ORGANISM: Zea mays

<400> SEQUENCE: 50
```

```
tggattcaga gggacgagag agcagcaggc atggaatgga actcacccccc cgctccctcc      60 acaccaccccc agcgttgtgg cagaggcgca taccgtcgtg ttagcttcgt ttctgctgta     120
aaaaaaaccc ttagtgtttt atttagcatg tagccttaac tggtcgtgtg ttacagtaca     180
gaactgatgc tgagttacaa caccctgatc tgatccctca actccaatgt aaccccttaac    240 agctcattct gtaaggaacc tgtcaccctg ttacctgttg ctgaactaat gaagtagagc     300
tagataatga cgttttatcg tagttattat taataact                              338

<210> SEQ ID NO 51
<211> LENGTH: 120
<212> TYPE: DNA
<213> ORGANISM: Zea mays

<400> SEQUENCE: 51
tggtacgcct gcaggtaccg gtccggaatt cccgggtcga cccacgcgtc cggccacggc      60
accgcaccac acgcagagcg gcagaggcac accagcagcc caaccggccg cgcgtgatcg     120

<210> SEQ ID NO 52
<211> LENGTH: 201
<212> TYPE: DNA
<213> ORGANISM: Zea mays

<400> SEQUENCE: 52
acccgtcaca gtccgttcgt taacctcaag gtcaagcagc tagcaatgct ctcctccgac      60 cacccctcagc tggcaaaactt caaactggag tcatcactca tcagtagtgc tgattattat   120
cctcccctga tgtcgtacgt tattttttttg tagactgtca ctcatccatc actaccccctt   180 aattagctttt attattagcg t                                               201

<210> SEQ ID NO 53
<211> LENGTH: 191
<212> TYPE: DNA
<213> ORGANISM: Zea mays

<400> SEQUENCE: 53
tgcaggtacc ggtccggaat tcccgggtcg acccacgcgt ccggtctgtg tgtttgtgat      60
agaatccaaa gacgcaagcg gctgcaggca gcagcgccgc gcaggcgttg tggcctgtgg     120
gagaggaaaa agagaaagag gaaccggcca agacaagcaa gcgagaggcc agggccgcgg     180
cgttgcgtca g                                                          191

<210> SEQ ID NO 54
<211> LENGTH: 333
<212> TYPE: DNA
<213> ORGANISM: Zea mays

<400> SEQUENCE: 54
agcgagcgtg cgtccggtgc aaggtgaagc tagaaagaga aagatgcccc ccaacaaaca      60
taacggagaa gagaaaaacc aaacaattaa gcagctttat agcctaagct aaccaccacc     120
attcatctcg tccaaatgcc ttgcttttct ctggagctag caggagcgcg tagttattta     180
gtactacttt acttattcag aggttatctt gaccccgata gatcaatccg cttactgtgt     240
aatttgtctc atgcatctct tagatggagt ttaatcgtct taatttactg tacagcagct     300
tgctggcttg caaagaaaga tctggtttgt ctc                                  333

<210> SEQ ID NO 55
```

<211> LENGTH: 191
<212> TYPE: DNA
<213> ORGANISM: Zea mays

<400> SEQUENCE: 55

```
tgcaggtacc ggtccggaat tcccgggtcg acccacgcgt ccggtctgtg tgtttgtgat    60
agaatccaaa gacgcaagcg gctgcaggca gcagcgccgc gcaggcgttg tggcctgtgg   120
gagaggaaaa agagaaagag gaaccggcca agacaagcaa gcgagaggcc agggccgcgg   180
cgttgcgtca g                                                       191
```

<210> SEQ ID NO 56
<211> LENGTH: 333
<212> TYPE: DNA
<213> ORGANISM: Zea mays

<400> SEQUENCE: 56

```
agcgagcgtg cgtccggtgc aaggtgaagc tagaaagaga aaagatgccc ccaacaaaca    60
taacggagaa gagaaaaacc aaacaattaa gcagctttat agcctaagct aaccaccacc   120
attcatctcg tccaaatgcc ttgcttttct ctggagctag caggagcgcg tagttattta   180
gtactacttt acttattcag aggttatctt gaccccgata gatcaatccg cttactgtgt   240
aatttgtctc atgcatctct tagatggagt ttaatcgtct taatttactg tacagcagct   300
tgctggcttg caaagaaaga tctggtttgt ctc                                333
```

<210> SEQ ID NO 57
<211> LENGTH: 182
<212> TYPE: DNA
<213> ORGANISM: Zea mays

<400> SEQUENCE: 57

```
ggtaccggtc cggaattccc gggtcgaccc acgcgtccga gaatccaaag cgcaagcggc    60
tgcagcctgc aggcagcgcc gcgcaggcgt gggagtggcc gagtgggagt gggagtgaaa   120
agaggaacc ggccaagaga agcaagcgag aagaaggcag tgctgcggcg gcgttccgta   180
ag                                                                 182
```

<210> SEQ ID NO 58
<211> LENGTH: 300
<212> TYPE: DNA
<213> ORGANISM: Zea mays

<400> SEQUENCE: 58

```
tagattcaga ggacatgaga gcagcagcat ggaactcacc tccgctccct ccaccgccgc    60
agcgtcgtgg cagaggcgca taccatcgtg ttagctttgt ttctgttgta aaaacttagc   120
gttagcttgt agccttaatt gtcgcgtgtc acagtacaga actgatgctg agttacagca   180
ccctgatatg atctggtccc tcaactccaa tgtaacccttt aacagctcat tctgtaagga   240
acctatcatc ctgttaccag ttgccgaatt aatgaagtag agctagataa tgatgttctg   300
```

<210> SEQ ID NO 59
<211> LENGTH: 46
<212> TYPE: PRT
<213> ORGANISM: Artificial
<220> FEATURE:
<223> OTHER INFORMATION: consensus

<400> SEQUENCE: 59

Pro Thr Thr Ala Glu Ile Glu Asp Phe Phe Ser Glu Ala Glu Glu Gln

```
                                              -continued
1                   5                    10                    15
Gln Gln Lys Gln Phe Ile Glu Lys Tyr Asn Phe Asp Ile Val Asn Asp
            20                    25                    30

Glu Pro Leu Glu Gly Arg Tyr Glu Trp Val Lys Leu Lys Pro
        35                    40                    45
```